(12) United States Patent
Weusthuis et al.

(10) Patent No.: US 8,900,834 B2
(45) Date of Patent: Dec. 2, 2014

(54) **PROCESS FOR POLYLACTIC ACID PRODUCTION USING *MONASCUS***

(75) Inventors: Alexander Ruud Weusthuis, GD Heelsum (NL); Emil Johan Harald Wolbert, LP Wageningen (NL); Jan Springer, AL Wageningen (NL); John Van Der Oost, HZ Renkum (NL); Gerrit Eggink, SC Ede (NL)

(73) Assignee: Total Research & Technology Feluy S.A., Feluy (BE)

( * ) Notice: Subject to any disclaimer, the term of this patent is extended or adjusted under 35 U.S.C. 154(b) by 0 days.

(21) Appl. No.: 13/882,467

(22) PCT Filed: Oct. 28, 2011

(86) PCT No.: PCT/EP2011/068969
§ 371 (c)(1),
(2), (4) Date: Apr. 29, 2013

(87) PCT Pub. No.: WO2012/055997
PCT Pub. Date: May 3, 2012

(65) Prior Publication Data
US 2013/0224813 A1    Aug. 29, 2013

Related U.S. Application Data

(60) Provisional application No. 61/407,747, filed on Oct. 28, 2010.

(30) Foreign Application Priority Data

Oct. 28, 2010 (EP) .................................. 10290583

(51) Int. Cl.
*C12P 7/62* (2006.01)
*C12P 7/56* (2006.01)
*C12P 7/40* (2006.01)
*C12N 9/58* (2006.01)
*C12R 1/645* (2006.01)
*C12N 9/04* (2006.01)
*C12P 7/46* (2006.01)

(52) U.S. Cl.
CPC . *C12P 7/40* (2013.01); *C12R 1/645* (2013.01); *C12N 9/0006* (2013.01); *C12P 7/46* (2013.01); *C12P 7/56* (2013.01); *C12P 7/625* (2013.01); *C12Y 101/01027* (2013.01)
USPC ............................ 435/135; 354/139; 354/223

(58) Field of Classification Search
None
See application file for complete search history.

(56) References Cited

U.S. PATENT DOCUMENTS

| 5,332,839 A | * | 7/1994 | Benecke et al. | ............... 549/274 |
| 6,320,077 B1 | * | 11/2001 | Eyal et al. | ..................... 562/589 |
| 2011/0155557 A1 | * | 6/2011 | Coszach et al. | ................. 203/33 |

FOREIGN PATENT DOCUMENTS

| EP | 1 325 959 | | 7/2003 | |
| WO | WO 2007032792 | * | 3/2007 | ............... C12N 1/18 |

OTHER PUBLICATIONS

Gao et al. "Separation of 1,3-propanediol from glycerol-based fermentations of Klebsiella by alcohol precipitation and dilution crystallization" 2007 Front Chem Eng China 1: 202-207.*
Williams et al. "A highly active zinc catalyst for the controlled polymerization of lactide" 2003 J Am Chem Soc 125: 11350-11359.*
Panagou et al. "Use of gradient plates to study combined effects of temperature, pH, and NaCl concentration on growth of Monascus ruber van rieghem an ascomycetes fungus isolated from green table olives" 2005, Applied and Environmental Microbiology 71: 392-399.*
Yang et al. "Agrobactrium tumefaciens-mediated transformation of Monascus ruber" 2008 J. Microbiol. Biotechnol 18: 754-758.*
Tseng et al. "Growth, pigment production and protease activity of Monascus purpureus as affected by salt, sodium nitrite, polyphosphate and various sugars" Journal of Applied Microbiology 2000, 88, 31-37.*
Yanchun, et al. "Characteristic Analysis of Transformants in T-DNA Mutation Library of Monascus ruber"; *World Journal of Microbiology and Biotechnology*, vol. 25, No. 6, (2009), pp. 989-995.
Yan-Chun, et al.; "The Targeted-deletion Technology in the Monascus ruber Mediated via Agrobacterium tumefaciens"; (2009), pp. 1-1Retrieved from http://en.cnki.com.cn/Article_en/CJFDTOTAL-WSWT200902023.htm.
Madhavan, et al. "An Overview of the Recent Developments in Polylactide (PLA) Research"; Bioresource Technology, vol. 101, No. 22, (2010), pp. 8493-8501.
International Search Report for PCT/EP2011/068969 mailed Feb. 10, 2012.

* cited by examiner

Primary Examiner — Suzanne M Noakes
Assistant Examiner — Gerard Lacourciere
(74) Attorney, Agent, or Firm — Hunton & Williams LLP

(57) ABSTRACT

A process for producing polylactic acid (PLA) comprising the steps: fermenting in a fermentation vessel a micro-organism of the genus *Monascus* in a medium at a pH less than or equal to 5 under conditions which produce lactic acid into the medium, converting the lactic acid produced into lactide, and polymerizing the lactide to form PLA.

23 Claims, 28 Drawing Sheets

Codon optimized Bt-L-LDH gene (Seq ID 1.)

ATGGCAACCCTGAAGGACCAGCTTATCCAAAACCTGCTCAAGG
AAGAACACGTCCCCAAAACAAGATTACTATCGTCGGAGTCGG
TGCCGTTGGAATGGCCTGCGCTATCTCCATTCTGATGAAGGAC
CTCGCAGATGAGGTGGCGCTCGTCGACGTTATGGAGGATAAGC
TCAA

A
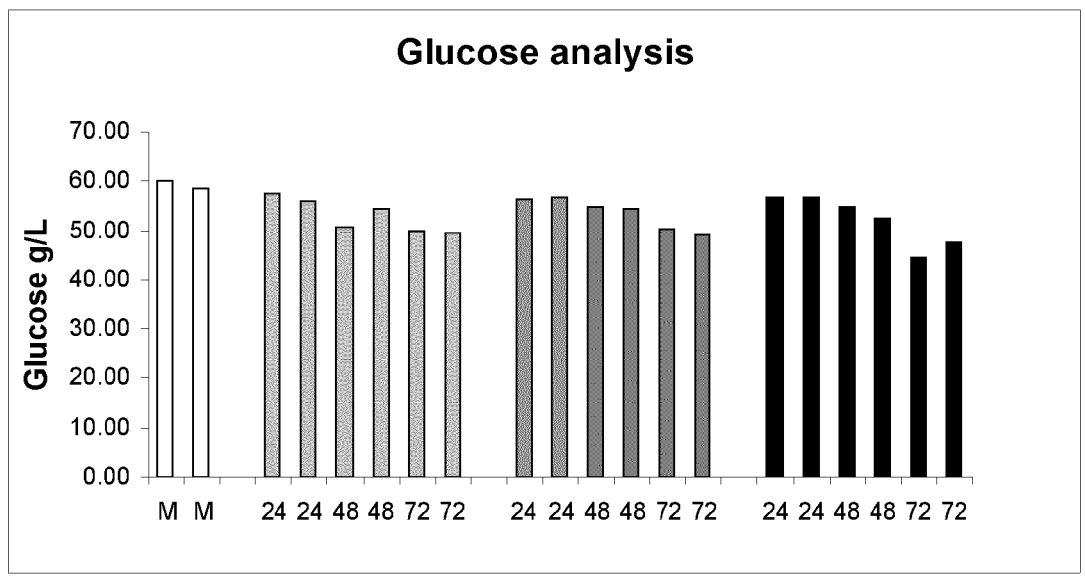
B
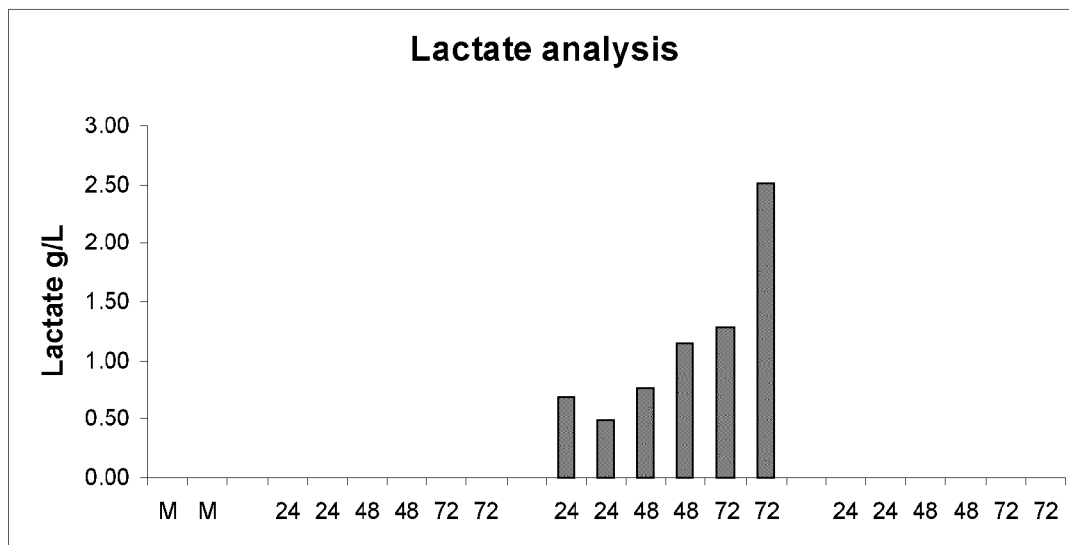
Figure 8

Monascus ruber PDC1 open reading frame (Seq ID NO:3)

TGGGTGGGYAAYTGYAATGARCTGAATGCTGGTTACKCCGCCG
ATGGCTACGCTCGTATCAAGGGTATCTCTGCCCTGATCACCACT
TTCGGTGTCGGTGAGCTCTCTGCCGCCAACGCCATCGCCGGTT
CCTACTCGGARCGGGTGCCCGTTGTCCACATTGTCGGTGAGCC
CAGCACGGCATCCCAGAACAACCGCCAGCTTCTGCACCACACC
CTCGGAAACGGTGACTTCGATGTCTTCGAGAAGATCTTCGCCA
AGATCTCTACTTCCGTCGTTAAGATTAGAGACCCCGCCAATGC
CGCCACCATGATCGACCACGTTCTCCGGGAATGTGTTATCCAG
AGCCGCCCCGTCTACATCGGTCTGCCCTCTGATATGGTTACCA
AGAAGGTTGAGGGAGCCCGCCTGAAGACCCCCATCGACCTGTC
CCTCCCCGAGAACCCCAAGGAGAAGGAGGACTACGTCGTCAG
CGTCGTTCTCAAGTATCTGCACGCTGCCAAGAACCCTGTCATC
CTCGTCGATGCCGGTGTCAACCGCCACAATGCCCAGGCTGAGG
TGCACGAGCTGATCAAGAAGTCTGGAATCCCCACCTTCATCAC
CCCCATGGGCAAGGGCGGTGTTGACGAAACCCTCCCCAACTAC
GGCGGTGTCTACGCCGGTACCGGTTCCAACAGGGGCGTCCGCG
AGCGTGTCGAGGAATCTGACCTCATCCTGAACATCGGACCTCT
CCAGTCCGACTTCAACACCACCGGCTTCTCCTACCGCACCAGC
CAGCTCAACACCATCGAGTTCGACCGCGACAGCGTCCAGGTCC
GCTACTCCTACTACCCCGACATCCAGCTTAAGGGAGTTCTCCA
GAACCTCATCGCCACCATGGGCGAACTCAACATCGAGCCTGGC
CCGACCCCCTCCAACGCCCTCCCCGCCAACGGCGTTGACCACG
AAACTGCAGAGATCACCCACGAATGGCTCTGGCCCATGGTCGG
CAACTGGCTCCGCGAAGGTGATGTTGTCCTCACTGAAACCGGT
ACCGCCAACTTCGGTATCTGGGAAACCCGCTTCCCCAAGAACG
TTCAGGCCATCTCCCAGGTCCTCTGGGGTTCCATCGGTTACTCC
GTCGGTGCCTGCTTGGGTGCTGCTCTCGCCGCTCGGGAACTTG
GCGACAACCGTGTCCTACTCTTCGTCGGTGATGGTAGCTTYCA
GATGACCGCCCAGGAGATCAGCACTATGATCCGTCAGGGATTG
AAGCCTATTGTCTTCGTCATCTGCAACAACGGCTACACMATCG
ARMGCTACATCCACGG

Figure 16

Monascus ruber PDC2 open reading frame (SEQ ID NO: 4)

CTGAACGCCGSCTACGCCGCCGACGGATAYGCTCGTGTCAATG
GAATCGCTGCCTTGGTTACTACTTTCGGTGTAGGAGAGCTGTC
AGCAGTGAACGCCATTGCGGGAGCCTACTCAGAGTATGTACCC
ATCGTTCACATTGTTGGCCAACCAAATACAAGGTCACAGAGAG
ATGGAATGCTGTTGCATCATACGTTGGGCAACGGCGACTTTGA
TGTCTTTACCAAGATGAGTGCTTCCATTTCGTGCGCTGTTGCAA
AGTTGAACGACCCCATGAAGCTGCAACGCTCATCGACCACGC
CATTCGGGAATGCTGGATTCGCAGCAGACCGGTGTACATCACC
CTCCCTACAGACATCGTCACGAAGAAAGTCGAAGGTGAAAGG
CTGAAGACCCCAATTGACCTGACAATGCCAGAGAATGAAGCA
GAAAGGGAAGATTACGTGGTGGATGTTGTTTGAAATACCTGC
AAGCCGCGAAAAACCCAGTCATTCTAGTTGACGCATGCGCAAT
CCGTCACAGGGTCCTGGACGAGGTACATGACCTTGTTAAGGCT
TCTGGCTTGCCAACCTTTGTGACCCCAATGGGCAAAGGAGCAG
TGGACGAGACTCATCCAAATTATGGTGGTGTGTATGCTGGAGA
TGGGTCTAATACCGGCGTCCGTGAAGTTGTTGAAGCTTCCGAC
CTTATTCTGAGCATTGGCGCCATTAAATCCGATTTCAATACTGC
CGGCTTCACATACCGCATCGGCCAACTTAACACGATCGACTTC
CATAGTACCTTCGTGCGAGTGAGGTATTCGGAGTACCCGAACA
CAAACATGAAGGGTGTTCTAAGGAAGATCATCCAGAAAATGG
GCCCCCTCAGCAAGACGCCTATTCCAAAGACTATCAACAAGGT
TCCAGAACATATCAAAGCTTCTGGTGACACGCGGATTACTCAT
GCTTGGTTGTGGCCGACAGTCGGACAGTGGCTGCAGCCGGAGG
ATGTTGTCGTCACTGAGACTGGAACTGCAAACTTTGGAATCTG
GGAAACCAGGTTCCCACACGGTGTCACGGCTATAAGCCAAGTC
CTCTGGGGAAGCATTGGGTACACGGTTGGAGCATGTCAAGGCG
CCGCACTAGCTGCAAAGGAGATAGGCAACCGTCGCACTGTACT
TTTTGTTGGCGATGGCAGTTTCCAGCTTACCGCGCAGGAAGTG
AGCACCATGCTCAGAAATAAGCTGAACCCGATCATTTTTGTGA
TCTGTAACGAAGGGTAYACRATCGAGCGCTACATCCATGGC

Figure 17

Monascus rubber gene encoding PDC4 (SEQ ID No: 5)

ATGACCACTGTCGGAAGCTACCTCGCAGAAAGGCTCTCCCAAATTGGCATCGAGCGC
CACTTCGTCGTCCCAGGCGACTACAACCTCATCCTCCTCGACAAACTCCAACAACAC
CCCAAACTCGACGAAATCAACTGCACAAATGAACTAAACTGCTCCATGGCCGCAGAA
GGCTACGCCCGCGCAAAAGGCGTAGCCGCCTGCGTCGTGACGTTCAGCGTCGGCGCA
TTCTCCGCATTCAACGGCATCGGCAGCGCATACGGTGAGAATCTCCCTGTCATCCTC
ATCTCCGGTTCCCCTAATACCAACGATCTTGGCTCGTCGCATTTGCTGCATCATACG
ATCGGTACGCATAATTTTGACTACCAGCTTGAGATGGCGAAAAATATCACCTGCTGT
GCTGTTGCGATTCGTCGTGCCTCGGATGCGCCGCGGTTGATCGACGAGGCTATTCGC
ACCGCACTTCGGGCGCGGAAACCAGCGTATATTGAGATTCCTACGAACCTCTCGGGC
CAGCCGTGTTCCCTGCCCGGACCGGCGTCGGGGATTCTCAAGCCGGATACGAGTGAT
ATTGATACTCTTGCGGAAGCGCTGAAGGCAGCCAACGACTTCCTCTCTACCCGGAAC
AAGGTGTCCTTACTGGTTGGCCCTAAGGTTCGCGCAGCAGGCGCTGAACATGCCGTG
ATCCATCTTGCTCAAGCCCTGGGATGCGCGGTGGCCGTGCTACCCAGTGCCAAATCG
TTCTTCCCGGAGACTCATCCGCAGTTCGTGGGTGTATACTGGGGCGAAGTGAGCACG
AAGGGCGCGAATGCTATCGTCGACTGGTCCGATACCCTTATTTGCGTGGGGACGGTT
TACACCGACTACAGCACCGTTGGATGGACGGGGCTACCCGAAGCAGCCAGTCTGACC
ATTGACCTGGACCATGTCAGTTTCCTGGATCCGATTACAACCAGATCCATATGCTG
GAGTTCGTGGCAGGACTGGCGAAGCTGGTGAAGAAGAACCCCCTGACACTCGTCGAA
TATAACCGTCTGCAACCAGACCCTCTCGTTCACACGCCATCTCCGCCGGATCAACGA
CTGAGCCGGCGAGAAATGCAGTACCAGATCAGCCAGTTCCTGACGCGCAACACGACG
GTCGTTGTGGACACGGGCGACTCGTGGTTCAACGGGATGCAGATGGACCTTCCGGAC
GGAGTGAGATTTGAGGTTGAGATGCAATGGGGACACATCGGATGGTCCGTTCCAGCA
GCACTGGGTCTGGCCGCCGCAAACCCCGAGCGACAGATAGTCGTCATGGTAGGCGAT
GGGTCGTTCCAGATGACGGGCCACGAGGTGTCAAATATGACTCGATTAGGGCTACCG
ATTATCATCTTCCTGATCAACAATGACGGGTACACAATCGAAGTCGAGATCCACGAT
GGCATCTACAACAACATCAAGAACTGGGATTACGGCGCGTTCGTCGAGTCGTTCAATGCCAAGGAG
GGACATGGGAAGGGGTATCGTGTTACCACGGCGGGGGAAATGCACAGGGCCATTGAGGCGGCGAAGAAG
AATAAACAGGGGCCAACACTAATCGAGTGTGATATTGATCGCGATGATTGCAGTAAGGAGTTGATCAGT
TGGGGGCATTATGTGGCTGCTGCGAATGGCAAGCCTCCTGTTGCCAGGTGA

Figure 24

Monascus ruber CYB2 open reading frame (SEQ ID NO: 2)

AAGTATGCGGGGCAGGATGCCACAAAGGCCTATTCTGAAGTTC
ACACTCCGAGCCTTATCAAATGGAATTTATCCCCAGACAAGCT
CAAGGGCACTCTCGGCCAATCCACTATTGACGATGAATGGATG
AAACCACCGCCAAATGAGAGCGACAAAGTTGTTTTAGAGAAC
GAGAAACCGCCGCTGCATATGCTGATAAACTCGCACGATTTCG
AAGTCGTAGCTTCCAAGACTGCAAGTAAGAAGACCTGGGCCTT
CTATTCCAGCGCTGCAACGGACCTCATCACCCGTGATGCCAAT
AAGTCATGCTTTGACCGGATATGGTTCCGACCCCGGGTACTGA
GGAATGTGCGTACCGTCAAAACGCGCACGAAGATCCTCGGGGT
TGACAGCAGTCTCCCACTTTCGTGAGTCCAGCAGCTATGGCT
AAGCTCATTCACCCAGATGGTGAGTGTGCCATAGCAAGGGCAT
GTGCAAATAAGGGTATCATTCAAGGTGTACgttcattgcagattcgaacactt
cccgttctagttgcaaccttcttaacatcaatgtcggatagGTGTCGAATAACTCATCAT
TCCCAATCGAAGAGCTCCGGGAGGCGGCACCGTCTGGAAATTT
TATTTTCCAGTTATATGTGAATCGGGATCGAGAGAAATCTGCG
GAACTACTCCGCAGGTGCTCAGCTAACCCGAACATCAAGGCCA
TCTTCGTGACCGTTGACGCAGCCTGGCCCGGTAAACGTGAGGC
AGACGAACGAGTCAAAGCGGATGAGAGCCTGACAGTCCCCAT
GTCCCCATCGACAACACGCAACGACAAAAGGGGGGCGGGCT
CGGGCGCGTTATGGCTGGGTTCATCGACCCGGGGCTCACCTGG
GAAGATCTGGCCTGGGTGCGACAACATACCCATCTCCCCGTTT
GTCTGAAGGGAATTATGTCCGCAGACGATGCCATTCTAGCCAT
GAAATTGGGACTAGATGGCATCCTGCTCTGCAACCACGGCGGC
CG

Figure 26

Replacement drawing sheet 1

Gene Mona00569 encoding cytochrome dependent L-LDH (SEQ ID No: 6)

| | | | |
|---|---|---|---|
| ATGTCTCAAC | CTAAGCTTAC | CGGCGCTGAT | ATCGCCAAAC |
| ACAATTCCAA | GGACTCGTGC | TGGGTCATTG | TCCACGGGAA |
| AGCATACGAT | GTCACGGACT | TCCTGCCAGG | TATTGATTGA |
| CCCCCCTGTC | CGGGAATTCC | GAGATGCTGC | CTGCGTTCAT |
| TGAATACTGA | TTTGCATGAA | TTTGATCAAT | TATAGAACAT |
| CCCGGTGGCC | AGAAGATTAT | CCTGAAGTAT | GCCGGCAGAG |
| ATGCCACGGA | AGAATTCGAG | CCCATCCACC | CCCCGGATAC |
| CCTGGACAAG | TACCTCGACA | AGTCAAAGCA | CTTGGGCGAG |
| GTCGACATGG | CCACTGTCGC | ACACGACGAG | AAGGCTGTCG |
| ATCCCGAGGA | GACGGCTCGC | CAGGAAAGAA | TCAAGCTCAT |
| GCCATCGTTG | CAATCCTGCT | ACAATCTGAT | GGACTTTGAA |
| TCCGTGGCGC | AGCAGGTCAT | GAAGAAGACT | GCGTGGGCAT |
| ACTACTCAAG | TGGTGCTGAT | GATGAAATCG | TATGACCATA |
| TCTGGATTTC | TCGTTCCCTT | TGCAGCACAT | ACTGACTTGC |
| GTCTGTTCAC | AGACCCTGCG | AGAAAACCAC | ACTGCCTTCC |
| ATAAGATCTG | GTTCCGGCCG | CGAGTCCTAG | TCGACGTGGA |
| ACATGTCGAC | TACTCTACGA | CCATGCTGGG | AACCAAGGTC |
| TCCGCTCCCT | TCTATGTGAC | GGCCACAGCC | CTGGGCAAAC |
| TGGGACACCC | CGAGGGTGAG | GTCGTTCTCA | CCCGTTCCTC |
| CTACCGTCAC | AACGTCATCC | AGATGATTCC | CACGCTCGCC |
| TCGTGCTCCT | TTGACGAGAT | TATTGACGCC | CGCCAAGGCG |
| ATCAGGTCCA | GTGGCTGCAG | CTCTACGTCA | ACAAGAACCG |
| CGATATCACC | AAGCGCATTG | TGCAACATGC | CGAAGCCCGC |

Figure 27 A

Replacement drawing sheet 2

| | | | |
|---|---|---|---|
| GGCTGCAAGG | GCCTCTTCAT | CACCGTCGAC | GCCCCGCAAT |
| TAGGTCGTCG | AGAGAAAGAC | ATGCGCTCCA | AGTTCTCCGA |
| CGAGGGCTCC | AACGTCCAGA | AAGAAGAGGG | TGAGGAGAAC |
| GTCGACCGCT | CTCAGGGTGC | CGCCCGTGCT | ATCTCCTCGT |
| TCATCGACCC | CGCCCTCTCC | TGGAAGGATA | TCCCCTGGTT |
| CCAATCCATC | ACGAAGATGC | CCATCGTCCT | GAAGGGTGTG |
| CAGTGCGTCG | AAGACGTTTT | CCGTGCTATC | GAAGCCGGAG |
| TCCAGGGTGT | TGTGCTGTCC | AATCACGGTG | GCCGTCAGCT |
| CGAGTTCGCA | CCATCGGCTG | TCGAGCTTCT | GGCCGAGGTT |
| ATGCCTGCGC | TGCGCCAGCG | CGGCTTGGAG | AACAGCATCG |
| AGGTGTACAT | CGACGGTGGC | ATCCGCAGAG | GCACTGATAT |
| CGTCAAGGCG | CTCTGCCTTG | GCGCCCAGGG | CGTGGGGATT |
| GGTCGTCCTT | TCCTGTACGC | CATGTCGGCG | TACGGCCAGG |
| CCGGTGTCGA | CAAGGCCATG | CAGCTTCTCA | AGGATGAGAT |
| GGAGATGAAC | ATGAGACTCA | TCGGAGCCAC | TAAGGTCTCC |
| GAGCTGAGCC | CCAGCCTCGT | CGATACCCGC | GGTCTTCTTG |
| GTGGTCACCA | CGCTCCTGTT | CCGTCCGACA | CGCTGGGCAT |
| GAAGGCGTAC | GATGCGCTCC | AGGCTCCGCG | GTTCAACGAA |
| AAGTCGAAGT | TGTAG | | |

Figure 27 B

PROCESS FOR POLYLACTIC ACID PRODUCTION USING *MONASCUS*

CROSS-REFERENCE TO RELATED APPLICATIONS

This application is the U.S. National Phase of International Application No. PCT/EP2011/068969 filed on Oct. 28, 2011, which claims priority to European Patent Application No. 10290583.3, filed Oct. 28, 2010, and U.S. Provisional Patent Application No. 61/407,747, filed Oct. 28, 2010, the contents of each are hereby incorporated by reference in their entireties.

TECHNICAL FIELD

The present invention relates to a process for the production of polylactic acid from lactic acid produced by microorganisms in fermentation.

BACKGROUND

Polylactic acid (PLA) is a thermoplastic, biodegradable aliphatic polyester that is manufactured from renewable sources by microbial fermentation, and has wide range of applications. Like most thermoplastic materials, it can be processed into a fibre or film. PLA has a wide range of applications, such as woven shirts, microwavable trays, and hot-fill applications. PLA is currently used in a number of biomedical applications, such as sutures, stents, dialysis media and drug delivery devices. In view of its biodegradability, it may also be used in the preparation of bioplastic, useful for producing loose-fill packaging, compost bags, food packaging, and disposable tableware. In the form of fibers and non-woven textiles, PLA also has many potential applications, for example as upholstery, disposable garments, awnings, feminine hygiene products, and diapers.

Bacterial fermentation is currently used to produce lactic acid from corn starch or cane sugar. However, lactic acid cannot be directly polymerised to a useful product, owing to the generation of water which degrades the forming polymer. Instead, it is dimerised to lactide. PLA of high molecular weight is produced from the lactide by ring-opening polymerization using most commonly a catalyst (e.g. tin). This mechanism does not generate additional water, and hence, a wide range of molecular weights is accessible. Typically PLA has a molecular weight number average (Mn) between 75 000 and 100 000 Dalton.

A number of microbes are capable of producing lactic acid by aerobic and anaerobic fermentation processes. *Lactobacillus* species are currently used extensively in industry for starch-based lactic acid production. The majority of these species lack the ability to ferment pentose sugars such as xylose and arabinose. Although *Lactobacillus pentosus, Lactobacillus brevis* and *Lactococcus lactis* are able to ferment pentoses to lactic acid, pentoses are metabolized using the phosphoketolase pathway which is inefficient for lactic acid production. Indeed, in the phosphoketolase pathway, xylulose 5-phosphate is cleaved to glyceraldehyde 3-phosphate and acetyl-phosphate. With this pathway, the maximum theoretical yield of lactic acid is limited to one per pentose (0.6 g lactic acid per g xylose) due to the loss of two carbons to acetic acid.

In most platform host organisms such as *E. coli*, production of lactic acid at high titers is either inefficient or toxic. The production of lactic acid at neutral pH typically results in the production of Ca-lactate, which has to be converted into lactic acid by the addition of sulphuric acid, resulting in the formation of $CaSO_4$ (gypsum) as by product. To produce lactic acid directly, the fermentation must be executed at low pH (preferably at least one unit lower than the pKa value of lactic acid, 3.85). Lactic acid however is toxic to microorganisms, as in its protonated form it acts as an uncoupler that destroys the membrane potential. Thus, while quite some micro-organisms may be tolerant to low pH only a limited number of organisms are suitable for organic acid production in that they are tolerant to organic acids at reduced pH.

An important drawback to microbial fermentation is the cost. As several microorganisms are unable to synthesize some of the amino acids or proteins they need for growing and for metabolizing sugars efficiently, they often must be fed a somewhat complex package of nutrients, increasing the direct expense to operate the fermentation. In addition, the increased complexity of the broth makes it more difficult to recover the fermentation product in reasonably pure form, so increased operating and capital costs are incurred to recover the product. Also, the use of corn as the feedstock competes directly with the food and feed.

Accordingly, there remains a need for improved methods for PLA production which utilise micro-organisms tolerant of high levels of lactic acid in a minimal fermentation broth.

SUMMARY OF THE INVENTION

The present invention provides methods for the production of PLA using improved micro-organisms that produce lactic acid. In particular, processes for producing polylactic acid (PLA) are provided comprising the steps:

fermenting in a fermentation vessel a micro-organism of the genus *Monascus* in a medium at a pH less than or equal to 5 under conditions which produce lactic acid into the medium, converting the lactic acid produced into lactide, and polymerizing the lactide to form PLA.

According to particular embodiments, the lactic acid is recovered from the fermentation medium prior to conversion into lactide by phase extraction. Accordingly, the recovery by phase extraction may comprise the steps:

(A) extracting free lactic acid from said medium clarified of debris by contacting said medium with an extracting solvent, to form:

(i) a lactic acid-containing extract and (ii) a lactic acid-depleted aqueous solution; and (B) separating said lactic acid-containing extract (i) from said aqueous solution (ii), thereby obtaining recovered lactic acid.

The extracting solvent for extraction may comprise one or more of 1-butanol, 2-ethyl hexanol, 1-octanol, methyl isobutyl ketone, cyclohexanone, disobutyl ketone, isopropyl ether, ethyl acetate, isobutyl acetate, ethyl lactate, butyl lactate, octyl lactate, N,N-dibutyl lactamide, and hexanoic acid. According to a preferred aspect of the invention, the extracting solvent comprises a tertiary alkyl amine, an oxygenated solvent that increases the partition coefficient, and a kerosene fraction that modifies the viscosity of the solvent mixture. The extracting solvent preferably comprises a tertiary alkylamine tricaprylyl amine (e.g. Henkel's Alamine 336). The extracting solvent may further comprise octanol or methyl isobutyl ketone, and kerosene (for example IsoPar K). According to one aspect of the invention, the extracting solvent contains 60 to 80 wt % tertiary alkylamine, such as Alamine 336, 5 to 20% methyl isobutyl ketone, and 10 to 30% kerosene (for example IsoPar K).

The phase extraction may be followed by an optional stripping step. Accordingly, the recovery may further comprise the steps:

(C) stripping the extracted lactic acid from said separated extract (i) using a stripping solvent to form as immiscible phases:
  iii) the stripping solution containing lactic acid, and
  iv) lactic acid-depleted extracting solvent,
(D) separating the stripping solution containing lactic acid (iii) from said lactic acid-depleted extracting solvent (iv), thereby obtaining recovered lactic acid. The stripping solvent is an aqueous solvent, polar organic solvent, or mixtures of these solvent.

According to another embodiment of the invention, lactic acid is recovered from the fermentation medium using an alcohol precipitation to precipitate contaminants. Accordingly, in one embodiment of the invention lactic acid is recovered from the fermentation medium prior to conversion into lactide, which recovery comprises the steps:
  precipitating contaminants in the medium, optionally clarified of debris, by use of an alcohol, and
  removing the precipitate to obtain a clarified alcohol solution containing lactic acid, thereby obtaining recovered lactic acid. The alcohol may be a $C_1$ to $C_4$ straight chain or branched alcohol.

The lactide in the process of the invention is typically converted from lactic acid directly or via polycondensation of lactic acid to form lactic acid oligomers. According to particular embodiments, the recovered lactic acid is converted into lactide by heating the recovered lactic acid to oligomerise the lactic acid, and heating the lactic acid oligomer so formed to produce a vapour of lactide. The recovered lactic acid may be in a hydrophobic solvent, preferably Alamine 336. The step of heating the lactic acid oligomer to produce a vapour of lactide may be performed in the presence of a catalyst, preferably a tin catalyst, preferably tin (II) octanoate. According to other particular embodiments, the lactic acid is in an aqueous solution, and is converted into lactide by heating the aqueous solution of recovered lactic acid to form a vapour, and passing the vapour so formed through a reactor maintained at elevated temperature, in which a catalyst is optionally disposed. The catalyst may be alumina. According to other particular embodiments, the lactic acid is in an aqueous solution, and is converted into lactide by the removal of water from the aqueous solution.

According to particular embodiments, the lactide is polymerised into PLA by a ring opening in the presence of a metal catalyst. The metal catalyst may have a general formula (I):

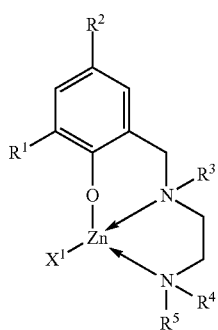

wherein
$R^1$ and $R^2$ are each independently $C_{1-10}$alkyl,
$R^3$, $R^4$ and $R^5$ are each independently $C_{1-10}$alkyl, or $R^3$ and $R^4$ are covalently bound to each other and are each a methylene and
$R^5$ is $C_{1-10}$alkyl,
$X^1$ is selected from $C_{1-10}$alkyl, —$OR^6$, or —$N(SiR^7{}_3)_2$, $R^6$ is $C_{1-10}$alkyl, and $R^7$ is $C_{1-6}$alkyl.

The invention uses micro-organisms which are highly tolerant to high concentrations of lactic acid at low pH and thus suitable for use in lactic acid production by genetic engineering. In further particular embodiments the invention uses recombinant fungi, more particularly of a species within the *Monascus* genus wherein certain exogenous and/or endogenous genes are over-expressed and/or suppressed so that the recombinant strains produce increased levels of lactic acid when cultivated in a fermentable medium. Accordingly, the recombinant *Monascus* strains of the present invention can be used for enhanced production of lactic acid at low pH thereby providing an increased supply of lactic acid for use in PLA manufacture.

The present invention thus uses micro-organisms for PLA production, more particularly of the genus *Monascus*, which are tolerant to high concentrations of lactic acid at low pH. In particular embodiments they are tolerant to increased concentrations of lactic acid at a pH which is less than 1.5 units above the pKa value of the lactic acid (3.85). More particularly the micro-organisms of the invention are tolerant to lactic acid at a pH of less than 5, more particularly less than 4, even more particularly less than 3, most particularly less than 2.8. In further particular embodiments, they are capable of growing in medium containing lactic acid at 50 g/L, most particularly 100 g/L, and in particular embodiments grow in medium containing lactic acid of up to 150 to 175 g/L, at low pH, more particularly at a pH of less than 5, more particularly less than 4, even more particularly less than 3, most particularly less than 2.8. In particular embodiments of the invention, the species within the *Monascus* genus is *Monascus ruber*. This high acid tolerance makes them particularly suitable for use in the industrial production of lactic acid, even under anaerobic or quasi anaerobic conditions.

These micro-organisms may be modified by genetic engineering to further enhance lactic acid production. In particular embodiments, the micro-organisms of the invention are capable of growing on hexose and pentose sugars and convert these sugars in lactic acid. In more particular embodiments the micro-organisms of the invention grow on glucose and xylose at a concentration at least 50 g/L, more particularly at concentrations of at least 70 g/L, at least 100 g/L, at least 200 g/L or more. In certain specific embodiments, the invention uses genetically modified or recombinant *Monascus* strains that are capable of producing increased levels of lactic acid, more particularly L-lactic acid at low pH. More particularly, L-lactic acid is produced at a high yield from hexose and/or pentose sugars.

In particular embodiments, the micro-organism comprises a heterologous or exogenous LDH gene. Accordingly, in particular embodiments, the invention uses genetically modified or recombinant *Monascus* strains comprising a heterologous or exogenous LDH gene. In further specific embodiments, the genetically modified or recombinant *Monascus* strains used according to the present invention comprise a heterologous or exogenous LDH gene that encodes a functional protein that is at least 80% identical to a protein encoded by SEQ ID NO:1.

The invention further envisages that the yield of lactic acid can be further enhanced by inactivating endogenous *Monascus* genes encoding proteins involved in an endogenous metabolic pathway which produces a metabolite other than lactic acid and/or wherein the endogenous metabolic pathway consumes the lactic acid. In particular embodiments, the production of the metabolite other than lactic acid of interest is reduced. According to further particular embodiments, the micro-organisms used according to the invention comprise at least one engineered gene deletion and/or inactivation of an endogenous pathway in which lactic acid is consumed or a gene encoding a product involved in an endogenous pathway which produces a metabolite other than lactic acid.

In particular embodiments, the micro-organisms of the strain Monascus used according to the invention are recombinant micro-organisms which comprise a recombinant gene encoding Lactic acid dehydrogenase (LDH) and/or at least one engineered gene deletion and/or inactivation of an endogenous lactic acid consumption pathway or a gene encoding an enzyme involved in an endogenous pathway which produces a metabolite other than lactic acid.

The genetically modified or recombinant Monascus strains used according to the present invention further contain at least one engineered gene or inactivation.

In more particular embodiments, the at least one engineered gene deletion or inactivation is in a gene encoding an enzyme selected from the group consisting of pyruvate decarboxylase (pdc), fumarate reductase, alcohol dehydrogenase (adh), acetaldehyde dehydrogenase, phosphoenolpyruvate carboxylase (ppc), D-lactate dehydrogenase (d-ldh), L-lactate dehydrogenase (l-ldh), lactate 2-monooxygenase, and any combination of said genes. In more particular embodiments, the at least one engineered gene deletion and/or inactivation is in an endogenous gene encoding lactate dehydrogenase.

In further embodiments the at least one engineered gene deletion and/or inactivation is in an endogenous gene encoding pyruvate decarboxylase (pdc). More particularly, the gene is an endogenous PDC1, PDC2 and/or PDC4 gene as described herein. In further particular embodiments, the one or more endogenous decarboxylase coding sequences that are inactivated and/or deleted are sequences corresponding to one or more of SEQ ID NO: 3, SEQ ID NO: 4 and/or SEQ ID NO: 5.

In particular embodiments, the at least one engineered gene deletion or inactivation is in an endogenous gene encoding a cytochrome-dependent lactate dehydrogenase, such as a cytochrome B2-dependent L-lactate dehydrogenase. More particularly, the engineered gene deletion or inactivation is an inactivation of a gene comprising SEQ ID NO:2 and/or in a gene comprising SEQ ID NO:6.

In particular embodiments, the micro-organisms used according to the invention are capable of producing the lactic acid at a yield of at least 0.5 g/L from hexose or pentose sugars or combinations of hexose and pentose sugars. More particularly, the yield is at least 2 g/L, most particularly at least 5 g/L. In particular embodiments the conversion yield of consumed sugar to lactic acid is at least 50%.

Particular embodiments of the invention use genetically modified or recombinant Monascus strains according to the present invention, which are capable of producing lactic acid, from hexose and/or pentose sugars at a yield of at least 2 g/L. In particular embodiments, ethanol is formed as a by-product. In particular embodiments, the lactic acid is L-lactic acid.

In certain embodiments, the methods of producing (compositions comprising) lactic acid of the present invention result in a yield of lactic acid that is at least 2 g/L. In further particular embodiments, the titer of lactic acid is between 50-100 g/L and the productivity is at least 1 g/L/hr, more particularly between 2-3 g/L/hr.

BRIEF DESCRIPTION OF THE FIGURES

The present invention is illustrated by the following Figures which are to be considered as illustrative only and do not in any way limit the scope of the invention.

FIG. 4 illustrates the sequence of the codon optimized Bt-L-LDH gene.

FIG. 8a illustrates glucose concentration in the media as determined by HPLC for transformants LF5-T1 and LF5-T2 and untransformed M. ruber control LF5 according to particular embodiments of the invention. FIG. 8b Lactic acid concentrations in transformants LF5-T1 and LF5-T2 and untransformed M. ruber control LF5 according to particular embodiments of the invention.

FIG. 16 illustrates the sequence of the Monascus ruber PDC1 open reading frame.

FIG. 17 illustrates the sequence of the Monascus ruber PDC2 open reading frame.

FIG. 24 illustrates the sequence of the *Monascus* ruber PDC4 open reading frame (SEQ ID No: 5).

FIG. 26 illustrates the sequence of the *Monascus ruber* CYB2 open reading frame. (SEQ ID NO:2); a putative intron in the genomic sequence is indicated by small letters.

FIG. 27 illustrates the sequence of the *Monascus ruber* Mona00569 gene encoding cytochrome dependent L-LDH (SEQ ID No: 6).

DETAILED DESCRIPTION OF THE INVENTION

Figure 1:
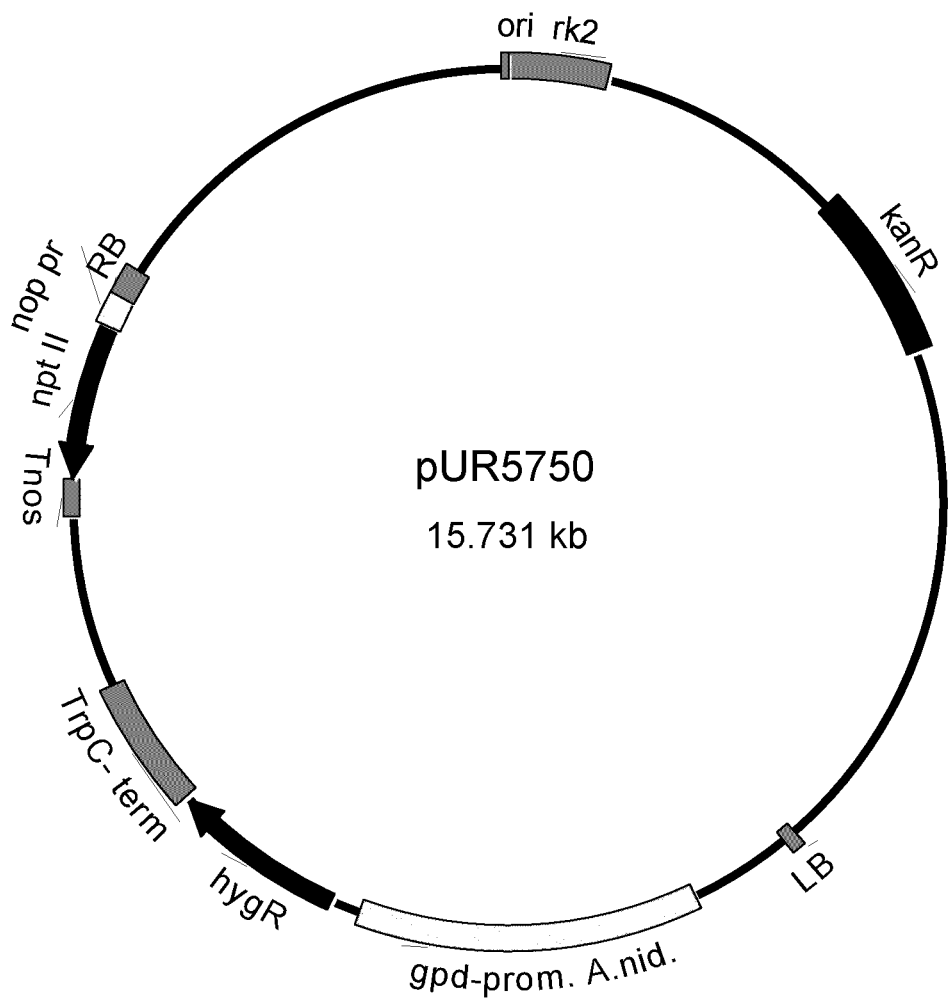
FIG. 1 illustrates an example of a transformation vector which can be used for the transformation of Monascus strains according to particular embodiments of the invention.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

Before the present process of the invention is described, it is to be understood that this invention is not limited to particular processes or products described, as such processes or products may, of course, vary. It is also to be understood that the terminology used herein is not intended to be limiting, since the scope of the present invention will be limited only by the appended claims.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

When describing the present invention, the terms used are to be construed in accordance with the following definitions, unless a context dictates otherwise.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. Where reference is made to embodiments as comprising certain elements or steps, this implies that embodiments are also envisaged which consist essentially of the recited elements or steps.

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

As used herein, the term "homology" denotes structural similarity between two macromolecules, particularly between two polypeptides or polynucleotides, from same or different taxons, wherein said similarity is due to shared ancestry. Hence, the term "homologues" denotes so-related macromolecules having said structural similarity.

All documents cited in the present specification are hereby incorporated by reference in their entirety.

As used herein, sequence identity between two polypeptides can be determined by optimally aligning (optimal alignment of two protein sequences is the alignment that maximises the sum of pair-scores less any penalty for introduced gaps; and may be preferably conducted by computerised implementations of algorithms, such as "Clustal" W using the alignment method of Wilbur and Lipman, 1983 (Proc. Natl. Acad. Sci. USA, 80: 726-730). Alternative methods include "Gap" using the algorithm of Needleman and Wunsch 1970 (J Mol Biol 48: 443-453), or "Bestfit", using the algorithm of Smith and Waterman 1981 (J Mol Biol 147: 195-197), as available in, e.g., the GCG™ v. 11.1.2 package from Accelrys) the amino acid sequences of the polypeptides and scoring, on one hand, the number of positions in the alignment at which the polypeptides contain the same amino acid residue and, on the other hand, the number of positions in the alignment at which the two polypeptides differ in their sequence. The two polypeptides differ in their sequence at a given position in the alignment when the polypeptides contain different amino acid residues at that position (amino acid substitution), or when one of the polypeptides contains an amino acid residue at that position while the other one does not or vice versa (amino acid insertion or deletion). Sequence identity is calculated as the proportion (percentage) of positions in the alignment at which the polypeptides contain the same amino acid residue versus the total number of positions in the alignment. In particular embodiment the algorithm for performing sequence alignments and determination of sequence identity is one based on the Basic Local Alignment Search Tool (BLAST) originally described by Altschul et al. 1990 (J Mol Biol 215: 403-10), more particularly the "Blast 2 sequences" algorithm described by Tatusova and Madden 1999 (FEMS Microbiol Lett 174: 247-250), such as using defaults settings thereof.

As used herein, "sequence similarity" between two polypeptides can be determined by optimally aligning (see above) the amino acid sequences of the polypeptides and scoring, on one hand, the number of positions in the alignment at which the polypeptides contain the same or similar (i.e., conservatively substituted) amino acid residue and, on the other hand, the number of positions in the alignment at which the two polypeptides otherwise differ in their sequence. The two polypeptides otherwise differ in their sequence at a given position in the alignment when the polypeptides contain non-conservative amino acid residues at that position, or when one of the polypeptides contains an amino acid residue at that position while the other one does not or vice versa (amino acid insertion or deletion). Sequence similarity is calculated as the proportion (percentage) of positions in the alignment at which the polypeptides contain the same or similar amino acid residue versus the total number of positions in the alignment.

The term "lactic acid" in this application refers to 2-hydroxypropionic acid in either the free acid or salt form. The salt form of lactic acid is referred to as "lactate" regardless of the neutralizing agent, i.e. calcium carbonate or ammonium hydroxide. As referred to herein, lactic acid can refer to either stereoisomeric form of lactic acid (L-lactic acid or D-lactic acid). The term lactate can refer to either stereoisomeric form of lactate (L-lactate or D-lactate). When referring to lactic acid production this includes the production of either a single stereoisomer of lactic acid or lactate or a mixture of both stereoisomers of lactic acid or lactate. In the particular embodiments where the recombinant fungi of the present invention exclusively produce a single stereoisomer of lactic acid or lactate, the lactic acid or lactate stereoisomer that is produced is said to be "chirally pure". The phrase "chirally pure" indicates that there is no detectable contamination of one stereoisomeric form of lactic acid or lactate with the other stereoisomeric form (the chiral purity of the specified stereoisomer is at least, greater than (or greater than or equal to) 99.9%).

The organisms used according to the present invention have been found to be highly tolerant to lactic acids at low pH.

As used herein the terms "tolerance to high lactic acid concentration" refers to the ability of the micro organisms to grow in a medium comprising at least 50 g/L lactic acid, or at least 75 g/L but potentially up to more than 100 g/L, or even more than 150 g/L, such as 175 g/L or 200 g/L. In particular embodiments, the term "high lactic acid concentration", may refer to a saturated solution of the lactic acid.

As used herein the term "low pH", refers to a pH of between 2.0 and 5.0, such as less than 4.0, more particularly less than 3.0, more particularly a pH of 2.8 or less.

It will be understood to the skilled person that when referring to a tolerance to an lactic acid at a low pH, of particular relevance is the ability to tolerate an lactic acid at a pH which corresponds to or is lower than the pKa value of the lactic acid, more particularly at a pH which is between 1.5 unit higher and 1.5 unit lower than the pKa value of the lactic acid. Where the lactic acid has two pKa values (due to the presence of two acid groups), the relevant pKa is the lowest pKa value.

"Lactate dehydrogenase activity" as used herein refers to the ability of the protein to catalyze the reaction of pyruvate to lactate. Lactate dehydrogenase enzymes include (but are not limited to) the enzymes categorized by the Enzyme Commission numbers EC1.1.1.27 and EC1.1.1.28.

The terms "recombinant" or "genetically modified" as used herein with reference to host organisms, microorganisms or cells, encompass such host organisms, microorganisms or cells into which a nucleic acid molecule has been introduced or which has been in another way genetically modified, as well as the recombinant progeny of such host organisms, microorganism or cells. This includes both organisms in which endogenous gene sequences are introduced at a position other than their natural position in the genome and organisms in which endogenous gene sequences have been modified or deleted.

The term "recombinant" as used herein with reference to a nucleotide sequence present in a host organisms, microorganism or cell refers to a nucleotide sequence which is not naturally present in said organisms, microorganism or cell. This includes nucleotide sequences which are foreign to said organisms, microorganism or cell and nucleotide sequences which are introduced at a position other than their natural position in the genome and endogenous gene sequences have been modified.

The term "transformation" encompasses the introduction or transfer of a foreign nucleic acid such as a recombinant nucleic acid into a host organism, microorganism or cell. The so-introduced nucleic acid or the resulting deletion of endogenous nucleic acid is preferably maintained throughout the further growth and cell division of said host organism, microorganism or cell. Any conventional gene transfer or genetic modification methods may be used to achieve transformation, such as without limitation electroporation, electropermeation, chemical transformation, lipofection, virus- or bacteriophage-mediated transfection, etc.

The term "gene" as generally used herein refers to a sequence which contains a coding sequence a promoter and any other regulatory regions required for expression in a host cell.

As used herein, the term "promoter" refers to an untranslated sequence located within 50 bp upstream the transcription start site and which controls the start of transcription of the structural gene. Generally it is located within about 1 to 1000 bp, preferably 1-500 bp, especially 1-100 bp upstream (i.e., 5') to the translation start codon of a structural gene. Similarly, the term "terminator" refers to an untranslated sequence located downstream (i.e., 3') to the translation stop codon of a structural gene (generally within about 1 to 1000 bp, more typically 1-500 base pairs and especially 1-100 base pairs) and which controls the end of transcription of the structural gene. A promoter or terminator is "operatively linked" to a structural gene if its position in the genome relative to that of the structural gene is such that the promoter or terminator, as the case may be, performs its transcriptional control function.

As used herein, the term "heterologous" or "exogenous" refers to the fact that the gene or coding sequence under consideration is not native or endogenous to the host.

The term "native" or "endogenous" is used herein with respect to genetic materials (e.g., a gene, promoter or terminator) that are found (apart from individual-to-individual mutations which do not affect function) within the genome of wild-type cells of the host strain.

By "encoding" is meant that a nucleic acid sequence or part(s) thereof corresponds, by virtue of the genetic code of an organism in question, to a particular amino acid sequence, e.g., the amino acid sequence of a desired polypeptide or protein. By means of example, nucleic acids "encoding" a particular polypeptide or protein may encompass genomic, hnRNA, pre-mRNA, mRNA, cDNA, recombinant or synthetic nucleic acids.

Preferably, a nucleic acid encoding a particular polypeptide or protein may comprise an open reading frame (ORF) encoding said polypeptide or protein. An "open reading frame" or "ORF" refers to a succession of coding nucleotide triplets (codons) starting with a translation initiation codon and closing with a translation termination codon known per se, and not containing any internal in-frame translation termination codon, and potentially capable of encoding a polypeptide. Hence, the term may be synonymous with "coding sequence" as used in the art.

The present invention relates to a method of preparing polylactic acid (PLA) from a fermentation process using micro-organisms. More in particular, the method describes the preparation lactide from lactic acid produced by the micro-organism, and preparation of PLA from the lactide.

The micro-organisms of the order of *Monascus* are used according to the present invention, have an excellent tolerance to high lactic acid concentrations at low pH. More particularly, they are tolerant to lactic acids at a pH of 5 or less.

The tolerance to lactic acid of the micro-organisms used according to the present invention makes them particularly suitable for use in the industrial production of lactic acid. While in some industrial settings, lactic acid of interest may be extracted during production such that extremely high concentrations are not maintained, the tolerance of the strain to the lactic acid will nevertheless be advantageous. More particularly, it is of interest to be able to allow fermentation of the strain in a medium whose pH drops during the course of fermentation, preferable to a value below the pKa of lactic acid of 3.85.

The micro-organisms of the present invention have an exceptional tolerance to lactic acid at a pH of less than 3.

It has moreover been found that the organisms used according to the present invention can be engineered to ensure production of lactic acid. More particularly they can be engineered to ferment simple sugars to a lactic acid at high yield. The fact that in particular embodiments these organisms can be cultivated under anaerobic or quasi-anaerobic conditions, provides an additional advantage in the context of industrial production methods.

The micro-organisms used according to the invention are of a species within the *Monascus* genus. It has surprisingly been found that *Monascus* strains can be identified which are tolerant to high lactic acid concentrations at low pH. Typically the micro-organisms represent a strain of a species that is chosen from the group comprising *Monascus albidulus, Monascus argentinensis, Monascus aurantiacus, Monascus barkeri, Monascus bisporus, Monascus eremophilus, Monascus floridanus, Monascus fuliginosus, Monascus fumeus, Monascus kaoliang, Monascus lunisporas, Monascus mucoroides, Monascus olei, Monascus pallens, Monascus paxii, Monascus pilosus, Monascus pubigerus, Monascus purpureus, Monascus ruber, Monascus rubropunctatus, Monascus rutilus, Monascus sanguineus, Monascus serorubescens* and *Monascus vitreus*. In particular embodiments of the present invention, the micro-organisms of the present invention are strains of the species *Monascus ruber*.

Exemplary strains used according to the present invention, referred to herein also as LF4, LF5 and LF6, have been deposited at the Centraalbureau voor Schimmelcultures (CBS) in Utrecht, The Netherlands and have been attributed the accession numbers CBS 127564, CBS 127565 and CBS 127566, respectively.

In particular embodiments, the invention uses micro-organisms of the order of *Monascus* as described above, which have been genetically engineered to improve lactic acid yield from simple sugars such as hexose or pentose sugars or combinations of hexose and pentose sugars. This can be achieved in different ways, which are not mutually exclusive.

In particular embodiments, the genetic engineering techniques envisaged in the context of the present invention aim at the increase lactic acid production by expression of an (exogenous) gene encoding an enzyme involved in the production of lactic acid.

Lactate dehydrogenase (LDH) catalyzes the last step in the conversion of sugars to lactic acid, whereby pyruvate is converted to lactate. Increased expression and/or activity of LDH genes thus ensures an increase in lactic acid yield. Accordingly, in particular embodiments, the invention provides genetically modified or recombinant *Monascus* strains comprising at least one functional lactate dehydrogenase gene integrated into its genome. In particular embodiments, the LDH gene comprises a heterologous or exogenous LDH coding sequence.

The introduction of an exogenous LDH gene enables the modified *Monascus* strain to produce increased quantities of the L- and/or D-lactic acid stereoisomer. According to certain particular embodiments of the present invention, the genetically modified or recombinant micro-organisms used of the order of *Monascus* comprise (or exclusively contain) one or more exogenous L-LDH genes (and not an exogenous D-LDH gene), so that the organisms produces an optically or chirally pure L-lactic acid. Alternatively, production of chirally pure D-lactic acid can be envisaged by introduction of an exogenous D-LDH gene. In specific embodiments of the present invention the genetically modified or recombinant organisms of the present invention of the order of *Monascus* contain one or more exogenous L-LDH coding sequence and one or more exogenous D-LDH coding sequences, so that the recombinant strain produces a racemic mixture of L- and D-lactic acid.

The exogenous LDH gene used in the context of the present invention, is a gene that encodes for a lactate dehydrogenase enzyme or an active fragment thereof, i.e. a protein having lactate dehydrogenase activity.

In particular embodiments, the exogenous LDH gene or coding sequence is a gene or coding sequence derived from another organism that has been genetically modified (e.g. codons altered) for improved expression in *Monascus*.

In the context of the present invention, suitable LDH genes include those obtained from bacterial, fungal, yeast or mammalian sources. Examples of specific L-LDH genes are those obtained from *Lactobacillus helveticus, L. casei, Bacillus megaterium, Pediococcus acidilactici, Rhizopus oryzae* and mammal sources such as bovine or swine. In particular *Bos taurus*. Examples of specific D-LDH genes are those obtained from *L. helveticus, L. johnsonii, L. bulgaricus, L. delbrueckii, L. plantarum, L. pentosus* and *P. acidilactici*. Functional coding sequences that have an identity score of at least 70% relative to the coding sequences in these genes at the amino acid level and encode functional proteins are suitable. The native genes obtained from any of these sources may be subjected to mutagenesis if necessary to provide a coding sequence starting with the usual eukaryotic starting codon (ATG), or for other purposes. In particular embodiments, the L-LDH gene is that obtained from *L. helveticus* or one that has a sequence identity therewith of at least 80%, 85%, 90% or 95%. According to other specific embodiments, the L-LDH gene that is obtained from *B. megaterium* or one at least 80%, 85%, 90% or 95% compared with such gene. According to further certain particular embodiments, the L-LDH gene is that obtained from *Bos taurus* or one that has an identities score of at least 80%, 85%, 90% or 95% compared with such gene. In particular embodiments, the D-LDH gene is that obtained from *L. helveticus* or one that has an identity score of at least 80%, 85%, 90% more particularly at least 95% compared with such gene.

Particularly suitable LDH coding sequences include those that encode for an enzyme with an amino acid sequence that has an identity score of at least 80%, 85% or 95%, compared with the sequence identified as SEQ. ID. NO. 1. Particularly suitable LDH genes also include those that encode a functional enzyme having a protein sequence that has an identities score of at least, 80%, 85% or 95% compared to the protein sequence encoded by SEQ ID NO:1; in particular embodiments suitable LDH genes include those that encode a functional enzyme and having a sequence that with an identities score of at least, 80%, 85% or 95% compared to the sequence of SEQ ID NO:1 or identical to SEQ ID NO:1. The genetically modified or recombinant *Monascus* strains of the present invention may contain a single exogenous gene encoding an enzyme involved in the production of the lactic acid of interest or multiple exogenous genes. Thus, for instance, the recombinant strain may comprise a single exogenous LDH gene or multiple exogenous LDH genes, such as from 1 to 10 exogenous LDH genes, especially from 1 to 5 exogenous LDH genes. When the transformed strain contains multiple exogenous LDH genes, the individual genes may be copies of the same gene, or include copies of two or more different LDH genes. Multiple copies of the exogenous LDH gene may be integrated at a single locus (so they are adjacent to each other), or at several loci within the genome of the host strain.

The recombinant coding sequence encoding the enzyme of interest is placed under the transcriptional control of one or more promoters and one or more terminators, both of which are functional in the modified fungal cell. Promoters and terminator sequences may be native to the *Monascus* host strain or exogenous to the cell. Useful promoter and terminator sequences include those that are highly identical (i.e. have an identities score of 90% or more, especially 95% or more, most preferably 99% or more) in their functional portions compared to the functional portions of promoter and terminator sequences, respectively, that are native to the host strain, particularly when the insertion of the exogenous gene is targeted at a specific site in the strain's genome.

In particular embodiments the promoter has an identity score at least 90%, 95% or 99% relative to a promoter that is native to a fungal gene. More particularly the promoter has an identity score of at least 90%, 95% or 99% compared to a promoter for a gene that is native to the *Monascus* host strain. In particular embodiments, the terminator has an identity score of at least 90%, 95% or 99% compared to a terminator for a gene that is native to a fungus. The terminator may have an identity score of at least 90%, 95% or 99% with a terminator for a gene that is native to the *Monascus* host strain. The use of native (to the host strain) promoters and terminators, together with their respective upstream and downstream flanking regions, can permit the targeted integration of the recombinant gene into specific loci of the host strain's genome, and for simultaneous integration the recombinant gene and deletion of another native gene. It is possible for the different exogenous coding sequences such as the LDH coding sequences to be placed under the control of different types of promoters and/or terminators.

The recombinant gene may be integrated randomly into the host strain's genome or inserted at one or more targeted locations. Examples of targeted locations include the loci of a gene that is desirably deleted or disrupted.

The present inventors further envisage increasing lactic acid production in the micro-organisms of the order of *Monascus* according to the invention, by limiting the production of metabolites endogenous to the host and/or reducing endogenous consumption of the lactic acid of interest. Indeed, this not only prevents the waste of material and energy by the host, but pushes the host to fully rely on the production pathway of the enzyme of interest created by introduction of the recombinant gene.

In fungi such as *Monascus*, lactic acid is consumed in the presence of oxygen. This is ensured by the cytochrome dependent lactate dehydrogenase. Accordingly, additionally or alternatively, according to particular embodiments of the present invention, the micro-organisms are modified to reduce endogenous consumption of lactic acid. More particularly, this is ensured by reducing expression of the endogenous LDH gene. This increases lactic acid yield under aerobic conditions.

Thus, according to a particular embodiment, the micro-organisms used in the present invention have one or more inactivated endogenous cytochrome-dependent LDH gene. The present inventors have identified and characterized the endogenous LDH gene from *Monascus ruber*. In particular embodiments, the endogenous LDH comprises the coding sequence of SEQ ID NO: 2 or the coding sequence of SEQ ID NO: 6. As detailed herein below nucleotide sequences derived from the coding, non-coding, and/or regulatory sequences of the endogenous LDH gene of *Monascus ruber* can be used to prevent or reduce expression of LDH in *Monascus*. In further particular embodiments, the genetic engineering techniques used in the context of the present invention are aimed at reducing the endogenous production of metabolites other than the lactic acid of interest. More particularly, recombinant micro-organisms are provided which are characterized in that enzymatic activities involved in the production of metabolites other than lactic acid such as ethanol have been inactivated or suppressed.

In this context it is meant by "inactivate" that all or part of the coding region of the gene is eliminated (deletion), or the gene or its promoter and/or terminator region is modified (such as by deletion, insertion, or mutation) so that the gene no longer produces an active enzyme, or produces an enzyme with severely reduced activity. Inactivation further includes silencing such as by antisense, triple helix, and ribozyme approaches, all known to the skilled person.

According to particular embodiments, the genetically modified or recombinant *Monascus* strains used according to the present invention comprise at least one engineered gene deletion and/or inactivation, more particularly in an endogenous gene encoding an enzyme involved in the ethanol production pathway. In these embodiments, the at least one engineered gene deletion or inactivation can for example be in an endogenous gene encoding an enzyme that is involved in ethanol production pathway or in the production of other metabolites than lactic acid in the host strain, such as a gene encoding an enzyme selected from the group consisting of pyruvate decarboxylase (pdc), fumarate reductase, alcohol dehydrogenase (adh), acetylaldehyde dehydrogenase, phosphoenolpyruvate carboxylase (ppc), D-lactate dehydrogenase (d-ldh), L-lactate dehydrogenase (l-ldh), lactate 2-monooxygenase and any combination of said genes. In more particular embodiments, the at least one engineered gene deletion and/or inactivation can be in an endogenous gene encoding pyruvate decarboxylase (pdc). Pyruvate decarboxylase catalyses the first step in the alcohol pathway. Accordingly micro-organisms having a substantially reduced pyruvate decarboxylase (PDC) activity are particularly envisaged. The term "reduced pyruvate decarboxylase activity" means either a decreased concentration of enzyme in the cell (as a result of at least one genetic modification affecting expression) and/or reduced or no specific catalytic activity of the enzyme (as a result of at least one genetic modification affecting activity).

In particular embodiments, the invention uses micro-organisms of the order of *Monascus* wherein the pyruvate decarboxylase activities approach zero or are reduced compared to the normal pyruvate decarboxylase activities in wild type strains. Accordingly, in particular embodiments the pyruvate decarboxylase activities in the strains of the present invention are for instance at least 60% lower, preferably at least 80% lower and even more preferably at least 90% lower than the pyruvate decarboxylase activity detectable in of wild type strains.

In particular embodiments, the invention provides microorganisms comprising one or more inactivated endogenous pyruvate decarboxylase genes. The present inventors have identified and characterized endogenous pyruvate decarboxylase genes from *Monascus ruber*. In particular embodiments, the endogenous pdc gene comprises the coding sequence of SEQ ID NO: 3 or SEQ ID NO: 4 or SEQ ID NO:5. In particular embodiments, the invention provides *Monascus ruber* strains in which all three pdc genes are inactivated or deleted. As detailed herein below nucleotide sequences derived from the coding, non-coding, and/or regulatory sequences of one or more of the endogenous pdc genes of *Monascus ruber* can be used to prevent or reduce expression of pdc in *Monascus*.

According to particular embodiments of the present invention, strains are provided, which are characterized by the feature that the ethanol production by said strain approaches zero or is at least reduced compared to the background ethanol production in the wild-type strain. Accordingly, in particular embodiments, the ethanol production in the strains of the present invention is for instance at least 60% lower, preferably at least 80% lower and even more preferably at least 90% lower than the ethanol production in the corresponding wild-type strain.

According to particular embodiments of the invention, strains of *Monascus* are provided, which are further modified to improve consumption of C5 sugars such as xylose. This can be achieved by methods known in the art, more particularly by introduction of genes encoding enzymes capable of converting glucose to xylose and/or reducing xylose to xylulose. In particular embodiments one or more endogenous or exogenous genes encoding xylose isomerase and/or xylose reductase are used. In further particular embodiments, exogenous xylose isomerase and/or xylose reductase genes are used. Examples of suitable xylose isomerase genes are known in the art and include but are not limited to xylose isomerase from *Piromyces* sp. and the reductase gene from *P. stipitis*. Thus in particular embodiments, the invention further provides *Monascus* strains which have been transformed with one or more genes involved in the metabolism of C5 sugars, more particularly xylose isomerase and/or xylose reductase. Genetic modification of the host strains is accomplished in one or more steps via the design and construction of appropriate vectors and transformation of the host strain with those vectors. Electroporation and/or chemical (such as calcium chloride- or lithium acetate-based) transformation methods or *Agrobacterium tumefaciens*-mediated transformation methods as known in the art can be used. The vectors can either be cut with particular restriction enzymes or used as circular DNA. The vector used for genetic modification of the host strains may be any vector so long as it can integrate in the genome of the host strain. Vectors of the present invention can be operable as cloning vectors or expression vectors in the selected host strain. Numerous vectors are known to practitioners skilled in the art, and selection of an appropriate vector is a matter of choice. The vectors may, for example, be the pUR5750 transformation vector, the pCGHT3 transformation vector . . . etc.

In general, a vector is prepared that contains the coding sequence of interest and associated promoter and terminator sequences. The vector may contain restriction sites of various types for linearization or fragmentation. Vectors may further contain a backbone portion (such as for propagation in *E. coli*) many of which are conveniently obtained from commercially available yeast or bacterial vectors. The vector preferably contains one or more selection marker gene cassettes. A "selection marker gene" is one that encodes a protein needed for the survival and/or growth of the transformed cell in a selective culture medium. Typical selection marker genes encode proteins that (a) confer resistance to antibiotics or other toxins such as zeocin (sh ble gene from *Streptoalloteichus hindustanus*), genetecin, melibiase (MEL5), hygromycin (aminoglycoside antibiotic resistance gene from *E. coli*), ampicillin, tetracycline, or kanamycin (kanamycin resistance gene of Tn903), (b) complement auxotrophic deficiencies of the cell. Two prominent examples of auxotrophic deficiencies are the amino acid leucine deficiency (e.g. LEU2 gene) or uracil deficiency (e.g. URA3 gene). Cells that are orotidine-5'-phosphate decarboxylase negative (ura3−) cannot grow on media lacking uracil. Thus a functional UBA3 gene can be used as a marker on a cell having a uracil deficiency, and successful transformants can be selected on a medium lacking uracil. Only cells transformed with the functional URA3 gene are able to synthesize uracil and grow on such medium. If the wild-type strain does not have a uracil deficiency (as is the case with *I. orientalis*, for example.), an auxotrophic mutant having the deficiency must be made in order to use URA3 as a selection marker for the strain. Methods for accomplishing this are well known in the art.

Preferred selection makers include the zeocin resistance gene, G418 resistance gene, hygromycin resistance gene. The selection marker cassette typically further includes a promoter and terminator sequence, operatively linked to the selection marker gene, and which are operable in the host *Monascus* strain.

Successful transformants can be selected for in known manner, by taking advantage of the attributes contributed by the marker gene, or by other characteristics (such as ability to produce lactic acid, inability to produce ethanol, or ability to grow on specific substrates) contributed by the inserted genes. Screening can be performed by PCR or Southern analysis to confirm that the desired insertions and deletions have taken place, to confirm copy number and to identify the point of integration of genes into the host strain's genome. Activity of the enzyme encoded by the inserted gene and/or lack of activity of enzyme encoded by the deleted gene can be confirmed using known assay methods.

The deletions or inactivations envisaged herein can be accomplished by genetic engineering methods, forced evolution or mutagenesis and/or selection or screening. Indeed, the present state of the art provides a wide variety of techniques that can be used for the inactivation, deletion or replacement of genes. Such molecular techniques include but are not limited to:

(i) gene inactivation techniques based on natural gene silencing methods including antisense RNA, ribozymes and triplex DNA formation, (ii) techniques for single gene mutation such as gene inactivation by single crossing over with non-replicative plasmid and gene inactivation with a non replicative plasmid or a linerized DNA fragment capable of double-crossover chromosomal integration (Finchham, 1989, Microbiological Reviews, 53: 148-170; Archer et al., 2006, Basic Biotechnology: 95-126), and (iii) techniques for multiple unmarked mutations in the same strain, such as but not limited to:

(a) deletion and replacement of the target gene by an antibiotic resistance gene by a double crossover integration through homologous recombination of an integrative plasmid, giving segregationally highly stable mutants;

(b) removing of the antibiotic resistance gene with the Flp recombinase system from *Saccharomyces cerevisiae* allowing the repeated use of the method for construction of multiple, unmarked mutations in the same strain and (c) generating a strain deleted for the upp gene, encoding uracil phosphoribosyl transferase, thus allowing the use of 5-fluorouracyl as a counter selectable marker and a positive selection of the double crossover integrants.

In particular embodiments the deletion or disruption of the endogenous gene is performed according to the method described by Oliveira et al (2008) (Appl Microbiol Biotechnol 80, 917-924).

In particular non-limiting embodiments of the present invention, the deletion or disruption of the endogenous gene, may include the introduction of one or more functional structural genes, notably a gene encoding an enzyme involved in the production of the lactic acid, such as an LDH gene as described above, inserted between the 5' and 3' flanking portions of one of the endogenous genes of the host strain. The functional gene preferably includes functional promoter and terminator sequences operatively linked to the structural gene. This approach allows for the simultaneous deletion of the endogenous gene and insertion of the functional exogenous or heterologous gene. The vector may include a selection marker gene instead of or in addition to the structural gene. Again, the selection marker gene is positioned on the vector between the 5' and 3' flanking portions of the endogenous gene(s) being targeted, and becomes inserted in the locus of the functional endogenous gene. The use of a selection marker gene has the advantage of introducing a means of selecting for successful transformants. However, it is also possible to select for successful transformants based on the resulting functional characteristics. For instance, depending on the genes deleted and introduced it may be possible to screen on reduced or eliminated ability to grow on specific building blocks, to produce lactic acid at high concentrations or on their reduced ability to produce specific metabolites such as ethanol.

Accordingly, a further aspect of the present invention provides methods of obtaining high yield lactic acid producing micro-organisms, which methods comprise:

a) obtaining a micro-organism of the genus of *Monascus* having a high tolerance to the lactic acid at low pH;

b) transforming the micro-organism with one or more recombinant nucleic acid sequences which ensure an increased production of the lactic acid and/or a reduction of endogenous production of metabolites; and c) selecting a micro-organism capable of high yield lactic acid production.

The step of identifying a micro-organism having a high tolerance to lactic acid at low pH can be obtained by selecting the micro-organism on a medium containing high concentrations of the lactic acid. More particularly selection is performed by selection on a medium containing the lactic acid at a pH which is one unit more than its pKa value. In further particular embodiments the pH is less than its pKa value. In particular embodiments, the pH is less than 3.8, more particularly less than 3.

In particular embodiments, the micro-organisms are selected on a medium containing the lactic acid at 50 g/L, most particularly 100 g/L, and in particular embodiments the micro-organism are selected on a medium containing the lactic acid of up to 150 to 175 g/L.

It has surprisingly been found by the present inventors that micro-organisms of the order of *Monascus* can be identified which are tolerant to high lactic acid concentrations at a low pH, more particularly at a pH which is less than the pKa of lactic acid. More particularly it has been found that micro-organisms of the order of *Monascus* can be identified which are tolerant to increased lactic acid concentrations at a pH of less than 3.0.

The step of transforming the micro-organism is described in detail hereinabove. As detailed above, different genetic modifications are envisaged which increase the yield of lactic acid production.

The step of selecting a micro-organism capable of high yield lactic acid production is a selection step known to the skilled person and includes but is not limited to measuring activity of enzymes involved in the production of the lactic acid of interest by methods such as those described for LDH in the Examples herein. Additionally or alternatively in the methods according to the invention, the selection step can be based on reduced production of ethanol, reduced lactic acid consumption, etc. . . .

In a further aspect, the present invention provides processes for producing lactic acid, more particularly at high yield. Indeed, high yield production of lactic acids is of interest in view of its numerous industrial applications. The methods of the present invention are of interest for the production for lactic acid for polylactic acid production.

In particular embodiments, the methods of the present invention comprise the steps of obtaining a micro-organism of the order of *Monascus* which is tolerant to high concentrations of lactic acid at low pH, genetically modifying it to increase yield of the lactic acid and culturing the thus obtained micro-organism in the presence of specific substrates or chemical building blocks at a pH of less than 5, more particularly less than 4, more particularly at a pH which is less than 1.5 units above the pKa of the organic acid.

In particular embodiments, the methods of the present invention comprise the steps of (i) obtaining a strain of the order of *Monascus*, which is tolerant to the lactic acid at low pH, more particularly at a pH which is less than 1.5 units above the pKa of the lactic acid;

(ii) modifying said strain such that it is capable of producing the lactic acid of interest at high yield from hexose or pentose sugars or combinations of hexose and pentose sugars; and (ii) culturing said strain in the presence of a suitable substrate, more particularly at a pH which is less than 1.5 units above the pKa of the organic acid, most particularly at a pH of less than 5, most particularly less than 4. Most particularly, the produced lactic acid is L-lactic acid. Methods for obtaining a micro-organism tolerant to lactic acid of the order of *Monascus* and methods of modifying said organism to increase lactic acid production yield are described hereinabove and illustrated in the Examples section.

In particular embodiments of the process of the invention, the micro-organism or strain of the order of *Monascus* can be cultivated in a medium that includes a sugar that is fermentable by the transformed strain. The sugar may be a hexose sugar such as glucose, glycan or other polymers of glucose, glucose oligomers such as maltose, maltotriose and isomaltotriose, panose, fructose, and fructose oligomers. In particular embodiments, the micro-organism is modified to have the ability to ferment pentose sugars, and the medium includes a pentose sugar such as xylose, xylan or other oligomer of xylose. In particular embodiments, the organisms are cultivated on combinations of hexose and pentose sugars.

The sugars can be hydrolysates of a hemicellulose or cellulose-containing biomass. In particular embodiments, the micro-organism is modified to ensure degradation of the biomass to monomers (e.g. expression of cellulase genes). Accordingly, in particular embodiments, the substrate comprises a sugar oligomer or polymer such as cellulose, hemicellulose or pectin.

Additionally or alternatively, enzymes can be added to the cultivation medium to ensure degradation of the substrate into fermentable monomers.

In particular embodiments of the invention, the medium contains at least (the equivalent of) 5 g/L, at least 10 g/L, at least 20 g/L, at least 30 g/L, more particularly at least 40 g/L, and even more particularly at least 50 g/L glucose. In further particular embodiments, the medium comprises at least 100 g/L, more particularly at least 200 g/L. Glucose may be added to the medium during the course of fermentation.

The medium may optionally contain further nutrients as required by the particular *Monascus* strain, including inorganic nitrogen sources such as ammonia or ammonium salts, and the like, and minerals and the like. However, in more particular embodiments, the medium is a complete mineral medium comprising a pentose or hexose sugar as the only carbon source. The ability of the strains of the present invention to grow on this simple medium greatly reduces cost of cultivation and simplifies purification of the lactic acid produced.

A preferred fermentation medium is S.C. medium which comprises $(NH_4)_2SO_4$ (at for example, 4-6 g/l, preferably 5 g/l), $KH_2PO_4$ (at for example, 2-4 g/l, preferably 3 g/l), $MgSO_4.7H_2O$ (at for example, 0.3 to 0.7 g/l, preferably 0.5 g/l), $ZnSO_4.7H_2O$ (at for example, 3.5 to 5.5 mg/l, preferably 4.5 mg/l), $MnCl_2.2H_2O$ (at for example, 0.6 to 1 mg/l, preferably 0.84 mg/l), $CoCl_2.6H_2O$ (at for example, 0.2 to 0.4 mg/l, preferably 0.3 mg/l), $CuSO_4.5H_2O$ (at for example, 0.2 to 0.4 mg/l, preferably 0.3 mg/l), $Na_2MoO_4.2H_2O$ (at for example, 0.2 to 0.4 mg/l, preferably 0.4 mg/l), $CaCl_2.2H_2O$ (at for example, 10 to 14 mg/l, preferably 12.25 mg/l), $FeSO_4.7H_2O$ (at for example, 2 to 4 mg/l, preferably 3 mg/l), $H_3BO_3$ (at for example, 0.5 to 1.5 mg/l, preferably 1 mg/l), KI (at for example, 0.05 to 0.15 mg/l, preferably 0.1 mg/l), $Glucose.H_2O$ (at for example, 40 to 70 g/l, preferably 55 g/l). Antifoam agent such as Sigma 204 antifoam may be employed.

Other growth conditions, such as total fermentation time, temperature, cell density, and the like are generally selected to provide an economical process. Temperatures during each of the growth phase and the production phase may range from above the freezing temperature of the medium to about 50° C. A preferred temperature, particularly during the production phase, is from about 30-45° C. Fermentation time may be equal to or greater than 10, 20, 40, 60, 80, 100, 120, 140, 160 hours, or a value in the range between any two of the aforementioned values, preferably between 100 and 140 hours. The pH may optionally be adjusted during fermentation to maintain a steady pH conductive to optimal growth. In particular embodiments, the pH is maintained at less than 4, more particularly less than 3.8, even more particularly less than 3, most preferably at 2.8.

The culturing step of the methods of the invention may be conducted aerobically, microaerobically or anaerobically. Quasi-anaerobic conditions or oxygen limited conditions, in which no oxygen is added during the process but dissolved oxygen is present in the medium at the start of the production process, can also be used.

In particular embodiments, the methods of the present invention comprise cultivation of micro-organisms (strains) of the order of *Monascus* which exhibit the ability to convert sugars to lactic acid under anaerobic or oxygen-limited conditions.

The cultivation step of the methods according to this aspect of the invention can be conducted continuously, batch-wise, or some combination thereof.

The yield of lactic acid obtained by the tools and methods according to the present invention will depend on the cultivation conditions used.

In certain embodiments, the methods of producing a lactic acid according to the present invention result in a yield of lactic acid that is at least 0.5 g/L, particularly at least 2 g/L, more particularly at least 3 g/L. Yields as high as 50 g/L, and more particularly between 50-100 g/L are envisaged. In further particular embodiments the production yield of about 2-3 g/L/hour.

In particular embodiments the micro-organisms of the present invention are capable of converting at least 50%, more particularly at least 60%, even more particularly 75%, most particularly at least 95%, and up to 100% of the glucose consumed. In practice, the yield obtained in particular embodiments of the methods of the present invention is at least 0.5 g/g sugar, more particularly at least 0.6 g/g sugar, but may be up to 0.95 g/g sugar.

A cultivation medium comprising about 4 to 100 g/liter total lactic acid material is typically provided for further processing. The cultivation medium is clarified to remove coarse impurities and other insolubles, for example by centrifugation or by passage through a filter or through flocculation, centrifugation or a combination of those various techniques. This filter may be a dead-end filter or a cross-flow filter using micro- or ultrafiltration membranes. In some instances, pretreatment with activated carbon may also be conducted to purify the mixture. The clarified medium may have a pH of 5 or less, preferably of 3.85 or less, more preferably of 3 or less, more preferably between 2 and 3. The pH may optionally be lowered using an acid such as sulphuric acid. Compounds secreted by the micro-organisms during the course of fermentation, notably lactic acid, lower the pH of the medium, hence adjustment of the pH may not be necessary.

Lactic present in the cultivation medium is converted into lactide, which lactide is a substrate for polymerisation into PLA. Conversion to lactide is greatly simplified in view of the fact that the organisms can be grown on a mineral medium containing only sugars as a carbon source.

Lactic acid may be first recovered from the cultivation medium prior to a subsequent conversion to lactide. Alternatively lactic acid may be converted in the cultivation medium into lactide, optionally with steps to remove impurities from the cultivation medium prior to conversion.

Depending on the solvent present with the lactic acid, conversion to lactide may proceed via polycondensation of lactic acid into oligomeric lactic acid, which oligomers are depolymerised into lactide. Typically lactic acid present in a non-aqueous solvent facilitates such depolymerisation or 'back-biting' reactions. Oligomeric lactic acid may have an average molecular weight of between 600 and 800.

When lactic acid is present in a substantially aqueous solvent, conversion may, alternatively, avoid formation of oligomeric lactic acid i.e. there is direct conversion of lactic acid into lactide, facilitating conversion directly using an aqueous feed from a lactic acid fermentor.

Prior to conversion into lactide, the lactic acid may first be recovered from the cultivation medium as mentioned earlier.

Typically lactic acid is extracted into an extracting solvent that forms a phase with the clarified medium, into which extracting solvent the lactic acid partitions. The partition containing lactic acid is removed.

Prior to extraction, the clarified broth may optionally be treated with an alcohol to precipitate impurities. The precipitation of contaminants may proceed using any technique known in the art, for example, as described in US2009/0093034. Precipitation preferably uses an alcohol (e.g. a $C_1$ to $C_4$ straight chain or branched alcohol), namely methanol, ethanol, propanol or butanol or a mixture of one or more of these. While lactic acid has a good solubility in methanol, ethanol, propanol, and butanol, the medium components contained in the lactic acid fermentation liquor and the agents for use in neutralization or acidification may have a poor solubility in these solvents. The propanol may be either one of 1-propanol (n-propanol) and 2-propanol (isopropanol). The butanol may be any one of 1-butanol (n-butanol), 2-methyl-1-propanol (isobutanol), 2-butanol (sec-butanol), and 2-methyl-2-propanol (tertbutanol).

Here, all of the medium components are soluble in water, but only few components among the medium components may be soluble in a lower alcohol.

By adding to the lactic acid fermentation liquor containing the medium components an alcohol such as methanol, ethanol, propanol, or butanol, which functions as a poor solvent, preferably with agitation, contaminants such as the medium components and the like can become insoluble therein and be precipitated, and the lactic acid component can be collected in the form of liquid supernatant using the subsequent extraction. The precipitate may be removed by centrifugation.

The extraction of lactic acid from the fermentation medium, optionally removed of impurities, may be performed by techniques known in the art, as described, for example, in US 98/15517, WO 99/19290, U.S. Pat. No. 5,831,122, WO 97/35489, US 2002/0102672 which are incorporated herein by reference. Most preferably extraction is performed using two-phase extraction.

According to one aspect of the invention, lactic acid is recovered from clarified medium by a method comprising the following steps:

(A) extracting lactic acid from said clarified medium by contacting said medium with an extracting solvent, to form:
  (i) a lactic acid-containing extract and
  (ii) a lactic acid-depleted aqueous solution; and
(B) separating said lactic acid-containing extract (i) from said aqueous solution (ii), thereby obtaining recovered lactic acid.

The extracts (i) and aqueous solution (ii) are in separate phases. The extracting solvent is at least partially, preferably fully water immiscible. The choice of extracting solvent is important to the overall efficiency and economics of the separation process. A measure of extraction efficiency is the partition coefficient as calculated by the concentration (wt. basis) of lactic acid in the organic phase (extractant) divided by the concentration of the lactic acid in the aqueous phase (phase from which extraction occurs). It is desired to have a partition coefficient greater than 0.1, even more desirable is a partition coefficient greater than 1.0, and even better if the partition coefficient is greater than 3.0. This latter can be accomplished by selecting the appropriate solvent or mixture of solvents from the following preferred solvents. Of course in commercial scale practice, extraction efficiency is the ability to achieve a combination of high yield, low extractant volume, and concentrated product. This can be accomplished with the techniques discussed herein.

Extracting solvent that gives favourable partitioning include: oxygenated solvents, phosphate esters, phosphine oxides, amines, and mixtures of these solvents. Oxygenated solvents that are suitable include alcohols, ketones, ethers, esters, acids or solvents that have a multiple number of these functional groups. Solvents including at least 60% by wt., more preferably at least 80% w/w and most preferably at least 90% w/w (typically 95% or more), component(s) which is (are) generally water immiscible (solubility not more than about 50 grams per liter in water at 25° C.) are preferable.

All percentages herein are by weight (w/w), unless otherwise stated.

Specific usable solvents are 1-butanol, 2-ethyl hexanol, 1-octanol, methyl isobutyl ketone, cyclohexanone, disobutyl ketone, isopropyl ether, ethyl acetate, isobutyl acetate, ethyl lactate, butyl lactate, octyl lactate, N,N-dibutyl lactamide, and hexanoic acid. Suitable phosphate compounds include tributyl phosphate (TBP), triphenyl phosphate, diethylhexylphosphoric acid, and trioctylphosphine oxide. Suitable amines may be chosen from the group consisting of primary, secondary and tertiary amines, with a total number of at least 18 carbon atoms. Mostly preferred are tertiary amines. Suitable amines include triethylamine, dioctylamine, trioctylamine, tridecylamine, methyl didodecylamine and industrial preparations such as Amberlite LA-1 (a dialkyl amine mixture with twelve carbon atoms in each alkyl chain), Alamine 304 (tridodecylamine), Alamine 308 (a trialkyl mixture of branched chains with a total of 8 carbon atoms on each chain), and Alamine 336 (a commercially available mixture of trioctyl; tridecyt; dioctyldecyl. and didecyloctyl amines). The extracting solvent may also preferably contain a hydrocarbon fraction, such as kerosene, typically (if used at all) at 1 to 40% w/w. Such a hydrocarbon fraction favorably modifies the viscosity, phase coalescence, and other physical properties of the system.

According to a preferred aspect of the invention, the extracting solvent comprises a tertiary alkyl amine, an oxygenated solvent that increases the partition coefficient, and a kerosene fraction that modifies the viscosity of the solvent mixture.

The extracting solvent preferably comprises a tertiary alkylamine tricaprylyl amine (e.g. Henkel's Alamine 336). The extracting solvent may further comprise octanol or methyl isobutyl ketone, and kerosene (for example IsoPar K). According to one aspect of the invention, the extracting solvent contains 60 to 80 wt % tertiary alkylamine, such as Alamine 336, 5 to 20% methyl isobutyl ketone, and 10 to 30% kerosene (for example IsoPar K).

According to another aspect of the invention, the extracting solvent comprises 45-55% tricaprylyl amine (Henkel's Alamine 336), 25 to 25% octanol, and the remainder being kerosene. Preferably, the extracting solvent comprises 48% tricaprylyl amine (Henkel's Alamine 336), 30% octanol, and 22% kerosene. One useable, and often preferred, extracting solvent comprises, by wt., 0 to 15% ethanol; 65 to 85% Alamine 336 and 15 to 35% kerosene.

According to another aspect of the invention, the extracting solvent comprises:
- at least one secondary or tertiary alkyl amine, in which the aggregate number of carbon atoms is at least 20, as a primary extractant; and
- a sterically hindered, polar, organic compound, having at least 5 carbon atoms, a basicity weaker than that of said primary extractant, and temperature-sensitive, extraction-modifying properties.

The sterically hindered, polar, organic compound may be selected from the group consisting of alkanols, carboxylic acids, tertiary amines, or trialkylphosphates, having a sterically hindering substituent attached to the carbon carrying said polar group, or to a carbon which is alpha, beta, or gamma to said carbon.

Depending on the desired process and the nature of the acid or salt and the primary extractant, said sterically hindered, polar, organic compound can be an extraction inhibitor, functioning, e.g., as a weak inhibitor at low temperature, and as a stronger inhibitor at higher temperature; or as an extraction enhancer having stronger extraction-enhancing activities at low temperatures than at higher temperatures.

Polar, and particularly protic, organic compounds act as enhancers of acid extraction by amines, due to their ability to solvate the amine acid ion pair formed on such extraction. Organic compounds suitable for use as enhancers in the present invention have at least one such polar or protic group, the solvating properties of which are hindered by the structure of the molecule. The polar group is preferably a hydroxyl, an ester, an aldehyde, a carboxyl, a ketone, or an amine, or said polar group can comprise a halogen, sulfur, nitrogen or phosphate atom. The hindrance can be achieved through substitution of a hydrogen atom in the alkyl chain by an aliphatic group, i.e., branching on the carbon atom carrying the polar group, or on a carbon which is alpha, beta, or gamma to said carbon.

The enhancer should be a weaker base than the amine used as the primary extractant in the extractant composite. On equilibrating it with a 0.1M aqueous HCl solution in a proportion that provides for enhancer to HCl molar ratio of 2, the aqueous phase pH will remain below 2. On a similar equilibration, with the amine acting by itself as the non-enhanced extractant, the pH of the aqueous phase increases to about 2.5 or higher.

The extracting solvent may comprise at least one secondary or tertiary alkylamine, the aggregate number of carbon atoms of which is at least 20, as the primary extractant. Particularly suitable amines are the commercially available trioctyl, tricaprylyl, tridecyl, and tridodecyl amines.

In addition to the primary extractant and the sterically-hindered, polar, organic enhancer compound, the extracting solvent may comprise a water-immiscible, polar or non-polar solvent, for example, aliphatic or aromatic hydrocarbon, hydrocarbons carrying nitro or halo substituents, and alcohols.

In preferred embodiments of the present invention, said sterically hindered, polar, extraction-enhancing compound is selected from the group consisting of secondary or tertiary alkanols, tris-2-ethylhexyl amine, and tris-2-ethylhexyl phosphate.

As indicated, the present improved process is especially applicable to recovering hydroxycarboxylic acids such as citric acid and lactic acid, and can be used to modify and replace the commercially-used process for the preparation of citrus acid, e.g., by replacing 1-octanol in the extractant composition with a sterically hindered, polar, organic compound having at least 5 carbon atoms and a basicity weaker than that of said primary extractant, as taught by the present invention.

The stripping step (step (C)—see below) may be performed at a temperature of at least 20 deg C. higher than the temperature at which said extraction is carried out. Said sterically hindered, polar, organic compound both modifies the extracting power of said primary extractant composition and facilitates said temperature-sensitive stripping operation.

According to one aspect of the invention, the extracting solvent comprises at least one $C_3$-$C_8$ alkanol. In particular, the extracting solvent contains up to 50% of a fatty amine having at least 18 carbon atoms. Preferably, the $C_3$-$C_8$ alkanol is n-propanol, 2-butanol. According to one aspect, the extracting solvent comprises 2-butanol and tridocylamine. According to one aspect, the extracting solvent comprises n-propanol and tridocylamine.

According to one aspect of the invention, the extracting solvent comprises a water insoluble amine. Use of an amine solvent is preferred due to favorable partitioning of lactic acid and selectivity. Preferably, the amine is immiscible in water and contains at least 18 carbon atoms. Most preferably, extraction is conducted with a tertiary amine. See for example U.S. Pat. Nos. 4,771,001; 5,132,456; and 5,510,526; and Shimizu et al, J. of Fermentation and Bioengineering (1996), Vol. 81 pp. 240-246; Yabannavar and Wang, Biotech Bioeng., (1991) Vol. 37, p. 1095-1100; and, Chen and Lee, Appl. Biochem. Biotech, (1997), Vol. 63-65, pp. 435-447. Suitable amines include aliphatic, araliphatic or aromatic amines, or mixed aliphatic-araliphatic or aliphatic-aromatic amines, or mixtures of such amines. Examples of amines include triethylamine, dioctylamine, trioctylamine, tridecylamine, methyl didodecylamine and industrial preparations such as Amberlite LA-1 (a dialkyl amine mixture with twelve carbon atoms in each alkyl chain, available from Rohm and Haas, Philadelphia, Pa.), Alamine 304 (tridodecylamine, available from Cognis, Tuscon, Ariz., formerly Henkel Corp.), Alamine 308 (a trialkyl mixture of branched chains with a total of 8 carbon atoms on each chain, available from Cognis, Tucson, Ariz.), and Alamine 336 (a mixture of trioctyl-; tridecyl-; dioctyldecyl- and didecyloctyl amines, available from Cognis, Tucson, Ariz.).

The extracting solvent may also preferably contain a hydrocarbon fraction to modify the viscosity, phase coalescence, and other physical properties of the system. An example of a suitable hydrocarbon is kerosene. For example, the IsoPar family of products from Exxon are suitable kerosene products. IsoPar K is particularly preferred. The hydrocarbon is typically (if used at all) included in the extraction solvent at about 1 wt % to about 70 wt %. A preferred solvent system comprises, by wt., 30 wt % to 70 wt % Alamine 304, 0 wt % to 20 wt % polar organic enhancer such as octanol or tributyl phosphate, and 30 wt % to 70 wt % kerosene. In solvent compositions with low enhancer concentration, a second organic phase may form during the extraction of lactic acid. Generally, the second organic phase includes a high concentration of lactic acid. However, the presence of a second organic phase could cause some operational difficulty.

The extraction solvent may also include an enhancer to increase the partition coefficient of the lactic acid. Enhancers are especially useful when the free lactic acid concentration in the aqueous phase is low, i.e., less than 15 wt %. Generally, lactic acid partitions more strongly into the organic phase in the presence of an enhancer and more strongly into the aqueous phase in the absence of an enhancer. The enhancer is typically selected based on its enhancement strength, volatility, reactivity, or any other property required for extraction efficiency or operating ease. Typical enhancers are polar organic compounds including alcohols, ketones, esters, amides, and other polar organic liquids. A volatile enhancer is preferred because it can be distilled from the loaded solvent prior to aqueous back extraction.

It has been found that sulfuric acid also acts as an enhancer and tends to increase the partitioning of lactic acid into an organic solvent, particularly an amine based solvent, more particularly a tertiary amine based solvent, at low lactic acid concentrations. Such sulfuric acid loaded amine based solvents are also referred to as sulfuric acid or sulfate containing solvents or sulfuric acid or sulfate enhanced solvents.

The temperature at which the extraction using the extracting solvent is performed can vary, depending on a number of parameters, including the extraction efficiency and viscosity. Typically, the extraction is performed at a temperature between about 0° C. and 95° C., preferably 20° C. and about 70° C., more preferably between about 30° C. and 60° C.

The aqueous lactic acid solution and extracting solvent may be contacted in a countercurrent fashion, for instance, in a mechanically-agitated column; a packed column; a perforated plate column; a pulsed column; a raining bucket contactor; a centrifugal contactor; or, mixer/settler equipment. The choice of equipment may depend upon the tendency for emulsion formation, and other operating parameters such as temperature and pressure. The exiting streams from the extraction process are a lactic acid depleted aqueous solution and a lactic acid-containing extract.

The ratio of extracting solvent to lactic acid-containing extract may be 5:1, 4:1, 3:1, 2:1, 1:1, 0.5:1, preferably 3:1.

The lactic acid-containing extract (i) may be converted into lactide in a subsequent step. The extracting solvent is typically non-aqueous, allowing conversion into lactide to proceed via a lactic acid oligomer. Techniques for conversion into lactide via lactic acid oligomers is described later on herein.

Alternatively, lactic acid-containing extract (i) may be subject to a stripping step, i.e. the lactic acid is back-extracted into a stripping solvent in increase purity, prior to conversion to lactide.

The use of a stripping step may be determined in part by the extracting solvent, for example, when the extracting solvent is a hydrophobic extracting solvent, a stripping step might be unnecessary. An example of a suitable hydrophobic extracting solvent is one with a high proportion of long-chain alkylamines, and optionally at least 1 to 35% kerosene by weight. Specific examples include Alamine-334, toluene, xylene, mesylene, ethylbenzene and mineral spirit.

Prior to conversion to lactide, the lactic acid-containing extract (i) may optionally be subject to a stripping step as mentioned elsewhere herein. The stripping may be performed according to techniques known in the art, as described for instance in US 98/15517 and WO 99/19290.

Thus, after steps (A) and (B) above, the method may further comprise the step:

(C) stripping the extracted lactic acid from said extract (i) using a stripping solvent to form:
  iii) a solution of lactic acid in the stripping solution, and
  iv) a lactic acid-depleted extracting solvent.

In a subsequent step (D), the stripping solution containing lactic acid (iii) is separated from said lactic acid-depleted extracting solvent (iv), thereby obtaining recovered lactic acid.

The solution of lactic acid (iii), and the (iv) lactic acid-depleted extracting solvent are formed in separate phases. Stripping (step C) may be performed by back-extracting the lactic acid in the extract (i) into a stripping solvent that is party or fully immiscible with the extracting solvent. The stripping solvent used to form the immiscible phase may be an aqueous solvent (e.g. water), polar organic solvent, or mixtures of these solvent. It has been found that some polar organic solvents are immiscible with the preferred extracting solvent described above. As the weight fraction of the trialkyl amine and kerosene increases, the probability that a polar organic compound is immiscible with the extracting solvent increases. Polar organic solvents of interest include: methanol; ethanol; lactide; lactic acid oligomers; dimenthyl sulfoxide (DMSO); N,N-dimethyl foramide (DMF); N-methylpyrrolidinone (NMP); 1,4-dioxane; 1,3-dioxane; tetramethylene sulfone (TMSF) and sulfolane. In general the polar organic solvents of interest are ones which have a solubility in water greater than 1 g per 10 g of water. When water is used as the stripping solvent, it can also include a basic compound to increase the distribution of lactic acid in the aqueous phase, such as sodium hydroxide, ammonium hydroxide or calcium hydroxide.

The back extraction will preferably be performed at a temperature higher than the initial extraction of lactic acid into the extracting solvent (typically 30° C. to 160° C. or higher, usually at 90° C. to 160° C.). There are exceptions to this and when using an extracting solvent comprising a large proportion alcohol such as hexanol or octanol, it can be favourable to perform the back extraction at a lower temperature than the initial extraction. As the temperature is increased above 100° C. in the case of an aqueous solvent, the back extraction is typically performed under pressure typically using nitrogen. The composition of the extracting solvent can be changed between the forward extraction of lactic acid and the back extraction.

The stripping solvent may also contain a basic compound to increase the distribution of the lactic acid back into the second immiscible phase. It has been found that the ternary system of triethylamine-lactic acid-trioctylamine at room temperature has two phases. This is somewhat surprising because triethylamine and trioctylamine are miscible. The trioctylamine phase contains little lactic acid if the amount of triethylamine added is slightly more than stoichiometric. The triethylamine-rich phase is nearly a 1:1 molar ratio of lactic acid to triethylamine, which gives a weight percent of lactic acid of 47%. Thus, this system is capable of concentrating the lactic acid during the back extraction. The triethylamine is substantially more volatile than lactic acid and can be distilled to obtain a crude lactic acid product. It is expected that trimethylamine, ammonia, and other amines with a molecular weight of less than 200 would show similar behaviour as the triethylamine. Bailey et al. disclose the use of trialkyl tertiary amines in an organic solvent with back extraction into an aqueous phase (with a relatively strong base such as ammonia) in U.S. Pat. No. 4,771,001 incorporated herein by reference.

Back extraction into a mixture of triethylamine in polar solvent with relatively low volatility is an efficient process since the solvent to triethylamine ratio can be carefully controlled. The presence of the solvent allows the viscosity to remain low during the distillation of the amine from the lactic acid and would provide a medium for further reactions of the lactic acid to lactic acid products.

This last recited option of back extracting the lactic acid has been generally described as having a non-polar solvent with a basic extractant, such as a long-chain (18 carbon atoms or more) alkylamine, and using a polar organic solvent as the back extracting phase. Of course, the opposite can be true. The initial extracting solvent can be relatively polar, but still immiscible with water, and the back extraction liquid can be a non-polar solvent with a basic extractant. The fundamental concept is the ability to extract lactic acid from an aqueous solution with an extracting solvent and back extracting the lactic acid into a second liquid. In some cases that liquid will be water, but it can also be an organic liquid that is appropriate for efficient separation of the lactic acid or to make and separate lactic acid products.

When back extracting the lactic acid into a second polar liquid phase, there will be a residual amount of the extracting solvent components in the lactic acid rich back extraction phase. If desired, the residual extracting solvent can be decreased by contacting the back extraction phase with a non-polar solvent such as IsoPar K.

The stripping solvent and lactic-acid containing extract may be contacted during back extraction in a countercurrent fashion in either: an agitated column; a packed column; a perforated plate column; a raining bucket contactor; a centrifugal contactor; or, mixer/settler equipment. The exiting streams from the extraction process are a lactic acid depleted extracting solvent and a lactic acid-containing stripping solvent.

The ratio of stripping solvent to extracting solvent may be 5:1, 4:1, 3:1, 2:1, 1:1, preferably 3:1.

The recovered lactic acid is subsequently converted to lactide. The stripping solvent may be removed from the lactic acid solution by evaporation where appropriate, and the residue resuspended in a hydrophobic solvent for direct conversion into lactide via lactic acid oligomers. Where the stripping solvent is aqueous, the lactic acid-containing solution may be converted directly into lactide using processes discussed elsewhere herein.

As mentioned above, lactide may be prepared essentially from the clarified fermentation medium. The clarified fermentation medium may optionally be treated to remove impurities. Examples of suitable treatment include a precipitation of contaminants using a technique known in the art for example, in US2009/0093034 which is incorporated here by reference. Precipitation uses an alcohol (e.g. a $C_1$ to $C_4$ straight chain or branched alcohol), namely methanol, ethanol, propanol or butanol or a mixture of one or more of these. While lactic acid has a good solubility in methanol, ethanol, propanol, and butanol, the medium components contained in the lactic acid fermentation liquor and the agents for use in neutralization or acidification may have a poor solubility in these solvents. The propanol may be either one of 1-propanol (n-propanol) and 2-propanol (isopropanol).

The butanol may be any one of 1-butanol (n-butanol), 2-methyl-1-propanol (isobutanol), 2-butanol (sec-butanol), and 2-methyl-2-propanol (tertbutanol).

Here, all of the medium components are soluble in water, but only few components among the medium components may be soluble in a lower alcohol.

By adding to the lactic acid fermentation liquor containing the medium components an alcohol such as methanol, ethanol, propanol, or butanol, which functions as a poor solvent, preferably with agitation, contaminants such as the medium components and the like can become insoluble therein and be precipitated, and the lactic acid component can be collected in the form of liquid supernatant, thereby obtaining recovered lactic acid. The precipitate may be removed by centrifugation.

When the content rate of water in the fermentation liquor is reduced by dehydration in advance, the effect of the alcohol functioning as a poor solvent is increased. Therefore, the increased amount of contaminants is precipitated, and thus the increased extent of solutes other than lactic acid is removed from the fermentation liquor to yield lactic acid with a lower amount of impurities.

The resulting supernatant may be further processed as such to form lactide. Alternatively, the supernatant can be distilled to obtain LA in concentrate form and resuspended in aqueous or an organic solvent. It will be appreciated that performing distillation separation and the like after the extraction using an alcohol with 5 or more carbon atoms presents difficulties since it has a high boiling point. For example, while methanol has a boiling point of 65° C., ethanol has a boiling point of 78° C., n-propanol has a boiling point of 97° C., isopropanol has a boiling point of 82° C., isobutanol has a boiling point of 108° C., tertbutanol has a boiling point of 82.5° C., 2-butanol has a boiling point of 100° C., and 1-butanol has a boiling point of 118° C., the boiling points of isomers of pentanol are 112 to 137° C., except that 2-methyl-2-butanol has a boiling point of 102° C. Furthermore, the cost of these alcohols is higher than that of a low molecular weight alcohol. The temperature at the extraction can be a temperature ranging from room temperature to the boiling point of each solvent. For example, in the case of ethanol, extraction can be performed at a temperature ranging from room temperature to 78° C. Furthermore, in a case where the solvents are used in combination, it is desirable that the temperature is set in consideration of the azeotropic point of the combined solvents and water. Accordingly, when the supernatant containing lactic acid is heated at least to the azeotropic point of the solvent and water, water can be evaporated out of the reaction system to dehydrate the supernatant. The heating is performed preferably with agitation. The dehydration of the supernatant as described above may be performed also by heating under reduced pressure.

The lactic acid may be suspended in a suitable solvent, for example e.g. Alamine 336, DMSO, toluene, mesitylene, ethylbenzene and mineral spirit preferably in a hydrophobic solvent. The recovered lactic acid solution is converted into lactide in a subsequent step.

The lactic acid, obtained by extraction (steps (A) and (B)), by stripping (step (C) and (D)) or present in the clarified fermentation medium, is converted into lactide using known methods of the art.

Generally, known methods comprise conversion via polycondensation of lactic acid to form lactic acid oligomers which subsequently form lactide; oligomerisation occurs particularly when the lactic acid is present in a non-aqueous or organic solvent. Such methods are described, for example, in WO 99/19290, U.S. Pat. No. 5,332,839, WO 92/05167, WO 95/09142 which are incorporated herein by reference.

Alternatively, known methods comprise the conversion of lactic acid directly into lactide without the formation of intermediate lactic acid oligomers. Direct conversion is facilitated particularly when the lactic acid is present in an essentially aqueous solvent. Such methods are described, for example, in WO 92/05167, U.S. Pat. No. 5,274,127, WO 95/09142, U.S. Pat. No. 5,319,107, U.S. Pat. No. 5,332,839 and U.S. Pat. No. 5,420,304 which are incorporated herein by reference.

Other techniques are described in DE 1234703, DE 267826, U.S. Pat. No. 5,053,522, WO95/09879, U.S. Pat. No. 1,995,870 and U.S. Pat. No. 4,797,468 are also incorporated herein by reference.

Where the recovered lactic acid from a step is present in an organic solvent (e.g. DMSO, Alamine 336, toluene, mesitylene, ethylbenzene and mineral spirit), particularly in a hydrophobic solvent, the mixture is heated to a temperature to drive the condensation of lactic acid to lactic acid oligomers. Depending on the solvent, this heating step may be performed at 160° C. at 50 mm Hg in the case of Alamine 336, or at 180° C. at atmospheric pressure in the case of DMSO. The heating may also serve to further evaporate water, in addition to driving the condensation to lactic acid oligomers. Optionally, the heating may be preceded by an initial water removal step e.g. by evaporation through heating. The average molecular weight of the oligomers is typically about 600 to 800. The reaction mixture is subsequently cooled. The cooling is typically in the range 60° C. to 120° C. When the solvent is Alamine 336, the mixture is cooled to 60° C., when it is DMSO, to 117° C. With certain solvents (e.g. Alamine 336), the mixture may split into two phases; one which is nearly pure extracting solvent, and another containing lactic acid oligomer. These phases are physically separated. The solution containing lactic acid oligomer is heated so that lactide is obtained in the vapour phase which can be condensed out. Heating is in the range 140 to 180° C., and a pressure of 5 to 10 mm Hg. When the solvent is Alamine 336, heating may be to 180° C. at 5 mmHg; when it is DMSO heating may be to 145° C. at 10 mmHg. A catalyst such as may be added to lactic acid oligomer solution. Examples of suitable catalysts include a tin catalyst, for instance, tin (II) octanoate, and FASCAT 9102 (a butyltin tris-2-ethylhexanoate). The catalyst may be added at about 0.1 to 0.5 wt %. The condensed lactide is collected. This process may be performed on the lactic acid-containing extract (i), particularly where Alamine 336 was used as the extracting solvent. It is also suitable for use directly on the lactic acid-containing extract (i) without a stripping step.

Alternatively, where the recovered lactic acid has been from a previous step is present in an aqueous phase, for instance, from the purified fermentation medium or after stripping (step (C)), it may be converted into lactide by vaporization of the recovered lactic acid. Such techniques are well known in the art, as described for example in U.S. Pat. No. 5,332,839 which is incorporated here by reference. The vapour is passed through a reactor maintained at elevated temperature, and in which optionally is disposed an alumina catalyst. Withdrawn from the reactor is product lactide, water, and unreacted aqueous lactic acid feed which are subjected to separation for recovery of the lactide product. The separated unreacted lactic acid feed is eligible for readmission to the process for making additional lactide. This cyclic process comprises the steps of passing make-up aqueous lactic acid feed into a vaporization zone along with unreacted aqueous lactic acid filtrate from another step of the process and therein forming aqueous lactic acid feed vapours. The thus-generated vapours then are passed through a vapour phase reaction zone held at elevated temperature for forming lactide therein. Lactide as a solid is separated from unreacted aqueous lactic acid filtrate; and the filtrate is recycled into the vaporization zone in the initial step of the process. The aqueous solution of lactic acid may be enriched primarily in monomeric lactic acid (L1A), and dimeric lactic acid (L2A), and some trimeric lactic acid (L3A), and depleted in higher oligomers (LnA). The aqueous solution of lactic acid may be provided as a feed.

The aqueous solution of lactic acid may be converted to lactide by: (a) converting aqueous lactic acid to its vapor phase; (b) passing the vapours through a vapour phase reaction zone maintained at elevated temperature; and (c) withdrawing from said reaction zone lactide, water, and unreacted aqueous lactic acid feed. The elevated temperature preferably ranges from about 150° C. to 225° C. The vapours are preferably passed through said vapour phase reaction zone with the aid of a carrier gas. The carrier gas preferably comprises nitrogen. The vapour phase reaction zone preferably contains an alumina catalyst. The method may comprise a further step (d) of passing said withdrawn lactide, water, and unreacted aqueous lactic acid feed through a cold cyclone for separation. Any oligomeric lactic acid in the aqueous solution of lactic acid (feed) may be converted to one or more of L1A, L2A, or L3A with water for its conversion to its vapor phase. The aqueous solution of lactic acid (feed) may be monomeric lactic acid (L1A).

The aqueous solution of lactic acid may be converted to lactide by: (a) passing make-up aqueous lactic acid (e.g. from a feed) into a vaporization zone along with unreacted aqueous lactic acid filtrate from another step of the process and therein forming aqueous lactic acid feed vapours; (b) passing said vapours through a vapour phase reaction zone held at elevated temperature for forming lactide therein; (c) separating lactide as a solid from unreacted aqueous lactic acid filtrate; and (d) passing said filtrate into said vaporization zone in step (a) of the process. The elevated temperature preferably ranges from about 150° C. to 225° C. The feed vapors are preferably passed through said vapour phase reaction zone with the aid of a carrier gas. The carrier gas preferably comprises nitrogen. The vapour phase reaction zone preferably contains an alumina catalyst. Any oligomeric lactic acid in the aqueous solution of lactic acid (feed) may be converted to one or more of L1A, L2A, or L3A with water for its conversion to its vapour phase. The aqueous solution of lactic acid (feed) may be monomeric lactic acid (L1A). The lactide may be separated as a solid from unreacted aqueous lactic acid filtrate by filtration by cold centrifuging. The filtrate may be subjected to distillation to concentrate the lactic acid content thereof prior to being passed into said vaporization zone. The filtrate may be dehydrated by distillation to a degree of polymerization (DP) of not substantially above about 2.

Where the lactic acid is present from the previous process in an aqueous solution, lactide may be formed by removing water from the aqueous solution of lactic acid. The lactide so formed may be separated from the crude product. Such technique is well known the art for example in WO 92/05167 which is incorporated here by reference. Water removal may be performed by any technique, for example by heating, by osmosis or by the addition of a water getter which preferentially reacts with water for forming a compound that is innocuous to the formation of lactide. Where heating is employed, water may be removed by distillation at an elevated temperature (e.g. 150° C. to 225° C.), which leads to oligomerisation of lactic acid; distillation proceeds until the degree of polymerization is not substantially above 2. Distillation is preferably conducted under vacuum. Where a water getter is used, it may include a compound such as an anhydride (e.g. acetic anhydride), an acetal (e.g. diethyl acetal of acetaldehyde), a carbodiimide and ketal (e.g. dimethyl ketal of acetone). Separation may be performed by cold water washing, fractional distillation, solvent extraction or solvent re-crystallisation. A co-distillation solvent may be employed, such as an alkyl benzene. An alkyl benzene may be selected from the group consisting of dodecyl benzene, tridecyl benzene and mixtures thereof.

Another suitable technique for lactide formation from an aqueous solution of lactic acid by water removal can be as described in U.S. Pat. No. 5,319,107. Water may be removed by a variety of methods, including, but not limited to, removing water as an azeotrope in which the reactive components are diluted in an azeotropic solvent, heating at an elevated temperature below the vaporisation temperature of lactic acid at an appropriate pressure either in the absence or presence of a nonazeotropic organic solvent, adding a water-getter which preferentially reacts with water, using molecular sieves or partitioning (e.g., osmotic) membranes, using anhydrous salts that form hydrated crystals with water, contacting the feedstream with water and absorptive materials, such as polysaccharides (e.g., Ficoll) or silica.

Examples of azeotropic solvents including water immiscible aromatic solvents, water immiscible aliphatic or cyclic hydrocarbon solvents and homogeneous solvents. Particular examples are discussed below. Examples of nonazeotropic solvents include aromatic compounds, such as halogenated aromatics, such as chlorinated aromatics and fluorinated aromatics, naphthalene, and aniline. Examples of water-getters include anhydrides, such as acetic anhydride; ketals, such as dimethyl ketal of acetone; acetals, such as diethyl acetal of acetaldehyde; and carbodiimides. Examples of molecular sieves include zeolites. Examples of anhydrous salts include anhydrous sodium sulfate and anhydrous magnesium sulfate.

Preferred methods for water removal include removing water as an azeotrope with an organic solvent and heating the feedstream under reduced pressure.

A more preferred method is removing water as an azeotrope from a lactic acid feedstream, which discussed as follows. Treatment of a lactic acid-containing feedstream to form cyclic esters can be influenced by several parameters including temperature, pressure, reaction time, presence of a catalyst, and presence of blocking agents. The temperature of the feedstream treatment controls both the rate of free water removal and the rate of esterification. The temperature of feedstream treatment for cyclisation and water removal is a temperature, for a given set of other treatment parameters, that is high enough for effective cyclic ester formation and not so high as to convert lactic acid components into aldehydes, carbon monoxide or other degradation products. Preferably, the lactide production temperature ranges from about 55° C. to about 250° C. More preferably the temperature is from about 60° C. to about 225° C. When used, the choice of solvent influences the temperature of the reaction, particularly when the reaction is being conducted at the boiling point of the solvent.

The pressure of the feedstream treatment may also influence the formation of lactide. For example, at higher pressures, higher reaction temperatures can be used for a given solvent which results in faster reaction rates, particularly in a vapour phase treatment. The pressure, however, can be either atmospheric, greater than atmospheric or less than atmospheric. A preferred pressure of the present invention is atmospheric pressure.

The feedstream treatment can be conducted for varying times and typically is conducted until cyclic ester formation is substantially maximised as determined by appropriate analytical techniques. The reaction time will of course vary according to other parameters such as temperature and the presence of catalyst. For example, the formation of lactide from lactic acid diluted in toluene by removing water as an azeotrope with toluene by heating from room temperature is substantially maximized within about 2 to about 5 hours. Shorter times may be preferred so as to minimize lactide degradation and racemisation.

A catalyst can be used to increase the rate of cyclisation. Although catalysts are not required, the use of stable catalysts that do not degrade in the reaction is preferred. For liquid phase production methods, there are many, which include ring closing esterification catalysts, which can be used including, but not limited to ion exchange acidic catalysts, such as Nafion and Dowex 50; soluble acidic catalysts, such as sulfuric acid, methanesulfonic acid, trifluoromethane sulfonic acid, and toluene sulfonic acid; silica-based catalysts, such as alumina-silicate; other solid heterogeneous acidic catalysts, such as alumina, eta, theta, delta and gamma alumina, silica, aluminium sulfate, lead oxide, antimony trioxide, boron trifluoride, beryllia, yttria; metal ester catalysts, such as stannous octoate and titanium tetra(isopropoxide); enzymes, such as hydrolases; zeolites; so-called template catalysts, such as di-n-butyltin oxide; micellar catalysts, including polar catalysts such as sulfosuccinate salts such as sodium di(2-ethylhexyl) sulfosuccinate sold as Aerosol OT by Pfizer, non-polar catalysts such as polyoxyethylene nonyl phenol, and phosphates. Preferred catalysts include zeolites and acidic catalysts, such as Dowex 50, gamma alumina, and toluene sulfonic acid.

The amount of catalyst used will vary depending on treatment parameters, such as temperature and pressure, reactivity of the catalyst and the desired rate of reaction increase. Thus, depending on reaction kinetics and treatment of a feedstream, optimum amounts of catalyst for production of cyclic ester may exist. At higher or lower amounts of catalyst, conversion rates can decrease.

Use of certain catalysts and other reaction parameters can be controlled to achieve a desired meso-cyclic ester product. For example, lactide has two asymmetric carbon atoms so it may be obtained in three stereoisomeric forms: L-lactide in which both asymmetric carbon atoms possess the L (or S) configuration; D-lactide in which both asymmetric carbon atoms possess the D (or R) configuration; and meso-lactide in which one asymmetric carbon atom has the L-configuration and the other has the D-configuration. L-lactide and D-lactide are enantiomers while meso-lactide is a diastereomer of L-lactide and D-lactide in which the methyl groups are trans to each other in the dioxanedione ring. Maintenance of the chirality in L-lactic acid will lead exclusively to the formation of L-lactide which has utility in the production of degradable polymers. However, racemisation of the chirality originally in L-lactic acid will lead to the production of meso-lactide which also has a key utility as a co-monomer with L-lactide in the production of degradable polymers. By variation of the conditions and catalysts used in each of the embodiments described for this invention, the lactide obtained from L-lactic acid feedstock, or feedstream, may be either nearly exclusive L-lactide or it may contain controlled quantities of meso-lactide in addition to L-lactide. For example, use of an acidic catalyst in the production of lactide has been found to result in increased production of meso-lactide.

In another embodiment of the present invention, blocking or end group agents can be employed to block the formation of hydroxy carboxylic acid oligomers larger in size than dimeric lactic acid. Blocking agents, such as anhydrides, ketones, and aldehydes are useful. In particular, such blocking agents are believed to block alcohol groups on the hydroxy acid, thereby preventing ester formation. Preferably with the use of blocking agents, the feedstream can be enriched for formation of lactic acid dimers from lactic acid without significant formation of lactic acid trimers or higher oligomers. Subsequently, the blocking agents can be removed to permit the formation of lactide from lactic acid dimer.

Where lactic acid from a previous step is in aqueous solution, lactide may be formed by the distillation of lactic acid at reduced pressure, for example, optionally in the presence of catalyst as disclosed in DE 1234703, DE 267826, U.S. Pat. No. 5,053,522, WO95/09879, U.S. Pat. No. 1,995,870 and U.S. Pat. No. 4,797,468, which are incorporated herein by reference. The lactide is present in the distillate. The distillation may be performed at a temperature in the range between 130° C. to 230° C. The pressure may be between 13 and 25 torr. The catalyst may be tin dust, a tin halide or an organic tin compound derived from a carboxylic acid having up to 20 carbon atoms.

The lactide obtained may be polymerised into PLA by known methods per se, for instance by ring opening polymerisation in the presence of a metal catalyst, such as a tin or a tin-free catalyst. Examples of techniques are described, for example, in U.S. Pat. No. 2,758,987, BE1008099, WO2004014889, U.S. Pat. No. 7,488,788, and U.S. Pat. No. 6,166,169 which are incorporated herein by reference in their entirety.

The polymerization method generally produces PLA of high molecular weight number average (Mn) between 75 000 and 100 000 Dalton. The PLA may have a polydispersity between 1.4 and 1.9. The term polydispersity, known in the art, is the ratio of weight average molecular weight (Mw) and number average molecular weight (Mn). The polymerization of lactide into PLA may proceed at a temperature between 160° C. and 195° C. The lactide is preferably contacted with a metal catalyst. Suitable catalysts can be catalyst of general formula $M(Y^1, Y^2, \ldots Y^m)_n$, in which M is a metal selected from the group comprising the elements of columns 3 to 12 of the periodic table of the elements, as well as the elements Al, Ga, In, Tl, Ge, Sn, Pb, Sb, Ca, Mg and Bi; whereas $Y^1, Y^2, \ldots Y^m$ are each substituents selected from the group comprising alkyl radicals with 1 to 20 carbon atoms, aryl radicals having from 6 to 30 carbon atoms, alkoxy radicals having from 1 to 20 carbon atoms, aryloxy radicals having from 6 to 30 carbon atoms, and other oxide, carboxylate, and halide groups as well as elements of group 15 and/or 16 of the periodic table; m and n are integers between 1 and 6. As examples of suitable catalysts, we may notably mention the compounds of Sn, Ti, Zr, Zn, and Bi; preferably an alkoxide or a carboxylate and more preferably $Sn(Oct)_2$, $Ti(OiPr)_4$, $Ti(2-ethylhexanoate)_4$, $Ti(2-ethylhexyloxide)4$, $Zr(OiPr)_4$, $Bi(neodecanoate)_3$ or $Zn(lactate)_2$. Other suitable catalysts can be catalyst of general formula (I):

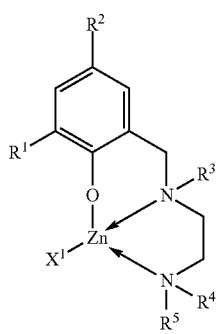

wherein
$R^1$ and $R^2$ are each independently $C_{1-10}$alkyl,
$R^3$, $R^4$ and $R^5$ are each independently $C_{1-10}$alkyl, or
$R^3$ and $R^4$ are covalently bound to each other and are each a methylene and
$R^5$ is $C_{1-10}$alkyl,
$X^1$ is selected from $C_{1-10}$alkyl, —$OR^6$, or —$N(SiR^7_3)_2$, $R^6$ is $C_{1-10}$alkyl, and $R^7$ is $C_{1-6}$alkyl.

The term "$C_{1-10}$alkyl", as a group or part of a group, refers to a hydrocarbyl radical of Formula $C_nH_{2n+1}$ wherein n is a number ranging from 1 to 10. Generally, the alkyl groups comprise from 1 to 10 carbon atoms, preferably from 3 to 10 carbon atoms, more preferably 3, 4, 5, 6, 7, 8, 9, or 10 carbon atoms. Alkyl groups may be linear, branched or cyclic and may be substituted as indicated herein. When a subscript is used herein following a carbon atom, the subscript refers to the number of carbon atoms that the named group may contain. Thus, for example, $C_{1-10}$alkyl includes all linear, or branched or cyclic alkyl groups with between 1 and 10 carbon atoms, and thus includes for example methyl, ethyl, n-propyl, i-propyl, 2-methyl-ethyl, butyl and its isomers (e.g. n-butyl, i-butyl and t-butyl); pentyl and its isomers, hexyl and its isomers, heptyl and its isomers, octyl and its isomers, nonyl and its isomers, decyl and its isomers and the like. For example, $C_{1-6}$alkyl includes all linear, or branched or cyclic alkyl groups with between 1 and 6 carbon atoms, and thus includes for example methyl, ethyl, n-propyl, i-propyl, 2-methyl-ethyl, butyl and its isomers (e.g. n-butyl, i-butyl and t-butyl); pentyl and its isomers, hexyl and its isomers.

The term "$C_{6-30}$aryl", as a group or part of a group, refers to a polyunsaturated, aromatic hydrocarbyl group having a single ring (i.e. phenyl) or multiple aromatic rings fused together (e.g. naphthalene), or linked covalently, typically containing 6 to 30 atoms; wherein at least one ring is aromatic. Non-limiting examples of $C_{6-30}$aryl comprise phenyl, biphenylyl, biphenylenyl, or 1- or 2-naphthanelyl.

$R^1$ and $R^2$ are each independently $C_{1-10}$alkyl; preferably, $R^1$ and $R^2$ are each independently $C_{1-6}$alkyl; preferably, $R^1$ and $R^2$ are each independently $C_{1-4}$alkyl; for example, $R^1$ and $R^2$ can be each independently selected from the group consisting of methyl, ethyl, n-propyl, i-propyl, 2-methyl-ethyl, n-butyl, i-butyl and t-butyl; preferably, $R^1$ and $R^2$ can be each independently selected from the group consisting of methyl, ethyl, i-propyl and t-butyl; for example $R^1$ and $R^2$ can be each independently selected from i-propyl or t-butyl; preferably, $R^1$ and $R^2$ are t-butyl, $R^3$, $R^4$ and $R^5$ are each independently $C_{1-10}$alkyl, preferably, $R^3$, $R^4$ and $R^5$ are each independently $C_{1-6}$alkyl, preferably $R^3$, $R^4$ and $R^5$ are each independently $C_{1-4}$alkyl, for example, $R^3$, $R^4$ and $R^5$ can be each independently selected from the group consisting of methyl, ethyl, n-propyl, i-propyl, 2-methyl-ethyl, n-butyl, i-butyl and t-butyl; for example, $R^3$, $R^4$ and $R^5$ can be each independently selected from the group consisting of methyl, ethyl, i-propyl and t-butyl; for example, $R^3$, $R^4$ and $R^5$ are each independently selected from methyl or ethyl; preferably, $R^3$, $R^4$ and $R^5$ are each independently methyl, or $R^3$ and $R^4$ are covalently bound to each other and are each a methylene and $R^5$ is $C_{1-10}$alkyl; preferably $R^5$ is $C_{1-6}$alkyl; preferably, $R^5$ is $C_{1-4}$alkyl; for example $R^5$ can be selected from the group consisting of methyl, ethyl, n-propyl, i-propyl, 2-methyl-ethyl, n-butyl, i-butyl and t-butyl; for example $R^5$ can be selected from the group consisting of methyl, ethyl, i-propyl and t-butyl; for example $R^5$ can be selected from methyl or ethyl; for example $R^5$ can be methyl;

$X^1$ is selected from $C_{1-10}$alkyl, —$OR^6$, or —$N(SiR^7_3)_2$, $R^6$ is $C_{1-10}$alkyl, and $R^7$ is $C_{1-6}$alkyl; preferably, $X^1$ is selected from $C_{1-6}$alkyl, —$OR^6$, or —$N(SiR^7_3)_2$, $R^6$ is $C_{1-6}$alkyl, and $R^7$ is $C_{1-6}$alkyl; preferably, $X^1$ is selected from $C_{1-4}$alkyl, —$OR^6$, or —$N(SiR^7_3)_2$, $R^6$ is $C_{1-4}$alkyl, and $R^7$ is $C_{1-4}$alkyl; for example $X^1$ can be selected from the group consisting of methyl, ethyl, n-propyl, i-propyl, 2-methyl-ethyl, n-butyl, i-butyl and t-butyl, or —$OR^6$, or —$N(SiR^7_3)_2$, $R^6$ can be selected from the group consisting of methyl, ethyl, n-propyl, i-propyl, 2-methyl-ethyl, n-butyl, i-butyl and t-butyl, and $R^7$ can be selected from the group consisting of methyl, ethyl, n-propyl, i-propyl, 2-methyl-ethyl, n-butyl, i-butyl and t-butyl; preferably, $X^1$ can be selected from the group consisting of methyl, ethyl, i-propyl and n-butyl, or —$OR^6$, $R^6$ can be selected from the group consisting of methyl, ethyl, i-propyl and t-butyl; preferably, $X^1$ can be selected from —$OR^6$, $R^6$ can be selected from the group consisting of methyl, ethyl, i-propyl and t-butyl; preferably, $X^1$ can be —$OR^6$, and $R^6$ is ethyl.

In an embodiment, $R^1$ and $R^2$ are each independently $C_{1-6}$alkyl. Preferably, $R^1$ and $R^2$ can be each independently selected from the group consisting of methyl, ethyl, i-propyl and t-butyl; for example $R^1$ and $R^2$ can be each independently selected from i-propyl or t-butyl; preferably, $R^1$ and $R^2$ are t-butyl.

In an embodiment, $R^3$, $R^4$ and $R^5$ are each independently $C_{1-6}$alkyl. For example, $R^3$, $R^4$ and $R^5$ can be each independently selected from the group consisting of methyl, ethyl, i-propyl and t-butyl; preferably, $R^3$, $R^4$ and $R^5$ can be each independently selected from methyl or ethyl; more preferably, $R^3$, $R^4$ and $R^5$ can be methyl.

For example, the process can be performed with a catalyst of Formula (I) wherein, $R^1$ and $R^2$ are each independently $C_{1-6}$alkyl; $R^3$, $R^4$ and $R^5$ are each independently $C_{1-6}$alkyl; and $X^1$ is selected from $C_{1-6}$alkyl, —$OR^6$, or —$N(SiR^7{}_3)_2$, $R^6$ is $C_{1-6}$alkyl, and $R^7$ is $C_{1-6}$alkyl.

For example, the process can be performed with a catalyst of Formula (I) wherein, $R^1$ and $R^2$ are each independently $C_{1-6}$alkyl; $R^3$ and $R^4$ are covalently bound to each other and are each a methylene and $R^5$ is $C_{1-6}$alkyl; and $X^1$ is selected from $C_{1-6}$alkyl, —$OR^6$, or —$N(SiR^7{}_3)_2$, $R^6$ is $C_{1-6}$alkyl, and $R^7$ is $C_{1-6}$alkyl.

For example, the polymerization of lactide into PLA can be performed with a catalyst of Formula (I) wherein, $R^1$ and $R^2$ are each independently $C_{1-4}$alkyl; $R^3$, $R^4$ and $R^5$ are each independently $C_{1-4}$alkyl, $X^1$ is selected from $C_{1-4}$alkyl, —$OR^6$, or —$N(SiR^7{}_3)_2$, $R^6$ is $C_{1-4}$alkyl, and $R^7$ is $C_{1-4}$alkyl.

For example, the polymerization of lactide into PLA can be performed with a catalyst of Formula (I) wherein, $R^1$ and $R^2$ are each independently $C_{1-4}$alkyl; $R^3$ and $R^4$ are covalently bound to each other and are each a methylene and $R^5$ is $C_{1-14}$alkyl; and $X^1$ is selected from $C_{1-4}$alkyl, —$OR^6$, or —$N(SiR^7{}_3)_2$, $R^6$ is $C_{1-4}$alkyl, and $R^7$ is $C_{1-4}$alkyl.

In a preferred embodiment, $R^1$ and $R^2$ are each independently $C_{1-4}$alkyl, preferably t-butyl or isopropyl; $R^3$, $R^4$ and $R^5$ are each independently $C_{1-2}$alkyl, $X^1$ is —$OR^6$, and $R^6$ is $C_{1-2}$alkyl.

In a preferred embodiment, $R^1$ and $R^2$ are each independently $C_{1-4}$alkyl, preferably t-butyl or isopropyl; $R^3$ and $R^4$ are covalently bound to each other and are each a methylene and $R^5$ is $C_{1-2}$alkyl; $X^1$ is —$OR^6$, $R^6$ is $C_{1-2}$alkyl.

In an embodiment, the catalyst is Formula (Ia), (Ib), (Ic) or (Id),

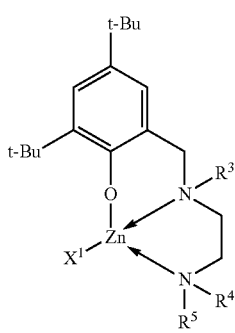
(Ia)

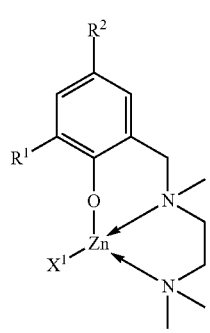
(Ib)

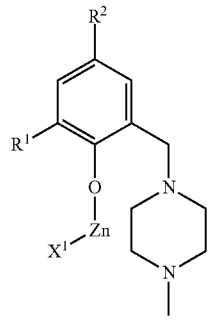
(Ic)

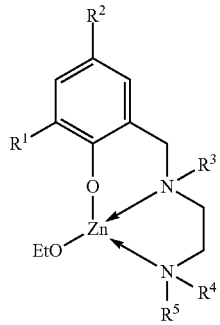
(Id)

wherein $R^1$, $R^2$, $R^3$, $R^4$, $R^5$ and $X^1$ have the same meaning as that defined above.

In an embodiment, said catalyst of Formula (I) is (2,4-di-tert-butyl-6-(((2-(dimethylamino)ethyl)(methyl)amino)methyl)phenoxy)(ethoxy)zinc, also referred to as "DDTBP-Zn(OEt)" represented by Formula (III).

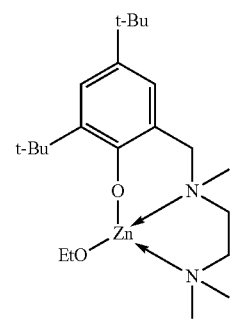
(III)

(2,4-di-tert-butyl-6-(((2-(dimethylamino)ethyl)(methyl)amino)methyl)phenoxy)(ethoxy)zinc can be prepared as described in Williams et al. (J. Am. Chem. Soc., 2003, 125, 11350-59) hereby incorporated by reference.

In general, the polymerization of lactide is performed in the presence of this type of catalyst, which is used in an amount such that the molar ratio of lactide/catalyst is between 1000/1 and 10 000/1, preferably between 2000/1 and 8000/1 and more preferably between 4000/1 and 6000/1.

The polymerization process of this invention to polymerize lactide in the D or L configuration is done in bulk, by contacting the lactide with the catalyst in a reactor preferably equipped with an agitator for high viscosity or extrusion in a extruder (or horizontal reactor) in single, double or multiple screws in an inert atmosphere in the presence of argon or nitrogen. However, it can also take place under ambient atmosphere.

The polymerization process can be usually done at a temperature between 160° C. and 195° C., preferably between 165° C. and 190° C.

The polymerization of lactide into PLA can also be done in the presence of stabilizers and/or antioxidants well known by those skilled in the art. Among the stabilizing agents commonly used include the (2,4-diterbutylphenyl)pentaerythritol diphosphite also known Ultranox 626. The polymerisation can be carried out continuously or intermittently.

Preferably, the lactide used in the process of the invention is the configuration of L-lactide (LL lactide) or lactide configuration D (DD lactide), more preferably lactide configuration L.

In a particular embodiment of the invention, the method may also include the use of an initiator. The initiator may be residual water contained in the lactide, an alcohol or an amine. Preferably, the initiator of the polymerization of lactide is an alcohol or amine.

The alcohol or amine may be aliphatic or aromatic of the formula $R-(A)_p$ where p is 1 or 2, A is OH or $NH_2$ and R is an alkyl radical containing 1 to 20 carbon atoms or aryl having 6 to 30 carbon atoms ($C_{6-30}$aryl). Preferably, R is an alkyl radical having 3 to 12 carbon atoms or aryl having 6 to 10 carbon atoms. The alkyl or aryl may be substituted or not. The alkyl may be linear, cyclic, saturated or unsaturated. Among the amines include isopropylamine, 1,4-butanediamine, 1,6-hexanediamine, 1,4 cyclohexanediamine. Among the alcohols include isopropanol, 1-octanol, 1,3-propanediol, 1,3-butanediol, 1,4-butanediol, 1,6-hexanediol, 1,7-heptanediol, xylene glycol.

The molar ratio of lactide and the initiator, when it is an alcohol or amine can be between 50/1 and 1500/1, preferably between 100/1 and 750/1, more preferably between 300/1 and 600/1.

The use of tin-free catalyst, as described above, allows the bulk polymerization of lactide at a temperature between 160° C. and 195° C. with a high conversion rate of lactide in polylactide while obtaining a colourless polylactide, directly after polymerization, and high number average molecular weight and low polydispersity, this phenomenon of avoiding degradation of the catalyst during polymerization. This result was quite unexpected because it could not be obtained with other species of zinc-based catalysts generally used so successfully for the solution polymerization of lactide.

The present invention will now be further illustrated by means of the following non-limiting examples.

EXAMPLES

Example 1

Isolation of Three *Monascus ruber* Strains LF4, LF5 and LF6 as Highly Lactic Acid Tolerant Strains The strains were isolated from soil and corn-and-wheat silage by incubation in medium at low pH, increasing lactic acid concentration and varying concentrations of glucose and xylose concentrations.

One strain (LF4) was isolated by incubation in DSMZ402 medium with 50 g/l glucose, 50 g/l xylose and 100 g/l lactic acid at pH 2.8 at 40 C.

Another strain (LF5), was isolated as described for LF4, but at pH 2.4

A third strain (LF6), was isolated by incubation in DSMZ402 medium with 25 g/l xylose and 150 g/l lactic acid at pH 2.8 and 32 C.

These three strains of the order of *Monascus*, more particularly *Monascus ruber* were found to be able to grow at low pH (2-3) in the presence of high lactic acid concentrations (up to 150 g/L). Lactic acid tolerant strains LF4, LF5 and LF6 were deposited as deposit under the Budapest Treaty by the Food & Biobased Research department of the Stichting Dienst Landbouwkundig Onderzoek, Bornseweilanden 9, 6708 WG Wageningen, Nederland on Jul. 21, 2010 and were attributed deposit numbers CBS 127564, CBS 127565 and CBS 127566, respectively.

Example 2

Stable Transformation with a Selectable Marker Gene

I. Materials and Methods
a) Transformation

Most protocols for genetic modification of *Monascus ruber* involve the transformation of protoplasts using electroporation or by combination of $CaCl_2$ and polyethylene glycol. However these methods often had low transformation efficiency and low mitotic stability. A transformation method using *Agrobacterium tumefaciens*-mediated integration of DNA with high efficiency has been reported in *M. ruber* (Yang 2008).

We have used this *Agrobacterium tumefaciens*-mediated transformation system for our *M. ruber* strains LF4, LF5 and LF6 and two selected CBS strains CBS 135.60 and CBS 503.70.

*Agrobacterium* strains containing the binary vector pUR 5750, described by de Groot et. al, 1998, were obtained from Plant Research International, WUR. These were grown at 30° C. for 48 h in minimal medium supplemented with kanamycin (100 µg/ml). The cells ($OD_{600}$~1.0) were washed with induction medium without Acetosyringone (AS) and grown with and without AS for 6 h at 28° C. AS was used for induction of virulence and T-DNA transfer. Conidiaspores of *Monascus ruber* ($10^7$ spores/ml) were collected from PDA plates after 10 days of culture. When conidia were transformed, an equal volume of conidia was mixed with an equal volume of *A. tumefaciens* and plated out on nylon filters placed on induction medium with and without AS. The plates were incubated at 25° C. for 4 days. The filters were then transferred to YM-medium containing 200 µg/ml cefotaxime to kill the *Agrobacterium* cells and 100 µg/ml hygromycin to select for transformants.

After 10-14 days fast growing fungal colonies were transferred to fresh YM plates+hygromycin and cefotaxime. After 5 days of growth the edge of the colony was transferred again to a fresh YM plates+hygromycin and cefotaxime.

Applying this procedure results in hygromycin resistant transformants for each of the selected *Monascus* strains (see Table 1).

TABLE 1

| Number of transformants per *M. ruber* strain | |
|---|---|
| *M. ruber* strain | No. of transformants |
| LF4 | 14 |
| LF5 | 3 |
| LF6 | 2 |
| CBS 503.70 | 4 | b) Stability of the Transformants

The first property of the transformants we have addressed is the genetic stability. With respect to this, two features of genetically modified strains are important:
   (i) the target gene has to be integrated into the genome, and
   (ii) the gene has to stay in place and active even without the selection pressure of the antibiotic Presence of the vector DNA in the transformants was first shown by means of PCR.

DNA was isolated from 7 transformants (5 LF4 transformants and 2 CBS 503.70 transformants) and from three wild type strains (LF4, CBS 503.70 and CBS 135.60) and subjected to a PCR with DNA primers able to show the hygromycin gene.

The DNA of the transformants clearly yield a PCR fragment of the same size as from the control vector DNA while the wild type strain do not show this PCR fragment. This shows the presence of the hygromycin gene in the transformants.

In order to establish integration of the vector DNA in the genomic DNA from the *M. ruber* transformants a Southern blot analysis was performed. Genomic DNA was blotted before and after digestion with a restriction enzyme. The blot was hybridized with a probe showing the presence of the hygromycin gene.

In the lanes with the genomic DNA the signals on the blot coincide with the position of the genomic DNA meaning integration of the hygromycin gene in the genome. In the lanes with the digested DNA the signals are visible on different positions (=different DNA fragments) meaning random integration of the hygromycin gene. In conclusion, we have established random genomic integration of the vector DNA in the *M. ruber* strains.

In order to test the stability of the transformants without the selective pressure of the antibiotic the strains were grown on PDA (potato dextrose agar) plates. After growth for approx. 14 days a part of the outer edge of the culture was transferred to a fresh PDA plate again without hygromycin. This process was repeated 3 times.

Finally a part of the outer edge of the culture was transferred to a fresh PDA plate with hygromycin to see whether the strain was still able to grow in the presence of this antibiotic.

The number of transformants still able to grow on selective plates after this procedure was scored (Table 2).

TABLE 2

*M. ruber* transformants screened for the stability of the hygromycin resistance.

| M. ruber strain | No. of transformants tested | No. of transformants growing on Hyg. after 3 transfers |
| --- | --- | --- |
| LF4 | 14 | 14 |
| LF5 | 3 | 3 |
| CBS 503.70 | 4 | 4 |

A second approach was to collect spores from the plate after 3 transfers without antibiotic selection and compare the number of colonies appearing after spreading the spores on PDA plates with and without hygromycin (selective plates). The spores were filtered through glass wool to minimize contamination with mycelial fragments. If the hygromycin gene is lost or inactivated the number of colonies on selective plates is reduced.

A test with all strains showed no reduction in the number of colonies on selective and non-selective plates. In conclusion, there is no evidence for instability or inactivation of the introduced gene in the *M. ruber* transformants.

As a final test the Southern blot experiment described before has been repeated with 27 transgenic strains after the sequential transfer on non-selective plates and subsequently growth in medium without selective pressure.

This Southern blot confirmed the presence of the hygromycin gene in the genome of the *M. ruber* transformants after growth in non selective medium.

c) Construction of Transformation Vectors

In order to be able to perform sequential transformations on *M. ruber* strains for instance to introduce multiple genes and/or to combine introduction of genes with knock out events, we set on to construct transformation vectors with other selectable markers.

The vector that has been used in the transformation described in the previous paragraph is the pUR5750 plasmid. FIG. 1 shows a map of this plasmid ("RB"=right border; "LB"=left border; "Hpt"=hygromycin phosphotransferase gene).

Figure 2:
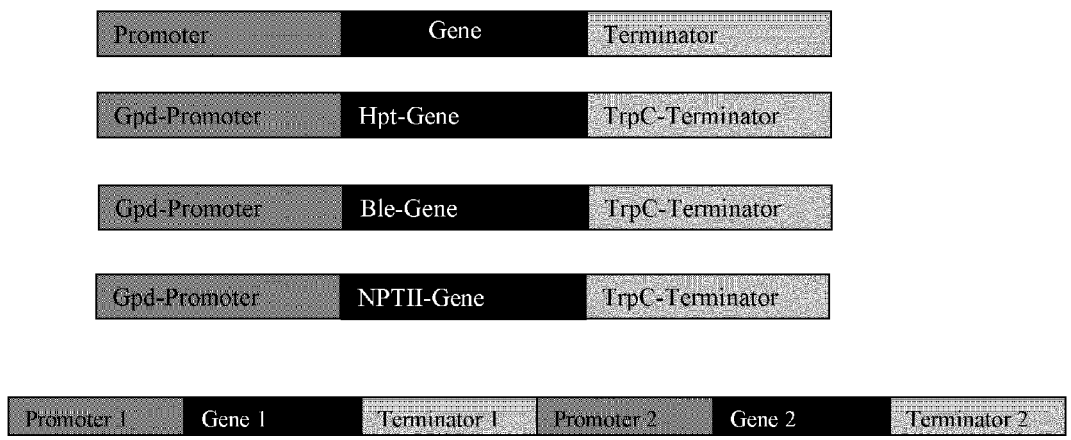
FIG. 2 illustrates an example of a cassette-model for vector construction according to a particular embodiment of the invention.

During transformation the DNA part between the RB (right border) and the LB (left border) is transferred into the fungal genome. On this part the Hpt gene is located. The activity of this gene, under regulation of the gpd-promoter and trpC-terminator, results in hygromycin resistance in transformants. In order to facilitate cloning and exchange of promoters, genes and terminators in this vector we designed a cassette model. As shown in FIG. 2, this cloning strategy enables us to exchange promoters, terminators and genes in the vector but also to combine 2 gene cassettes in a row.

Hpt is the hygromycin phosphotransferase gene giving hygromycin resistance which we already have used. Ble is the bleomycin gene giving phleomycin or zeocin resistance. NptII is the neomycin phosphotransferase gene giving neomycin (G418) resistance.

Since the pUR5750 transformation vector is a large vector, which will become even larger when additional genes are inserted (see FIG. 2), we decided to use also a shorter version of this vector for the transformation of *M. ruber*. In general it is assumed that smaller vectors can be handled more easily during construction and transformation experiments.

Figure 3:
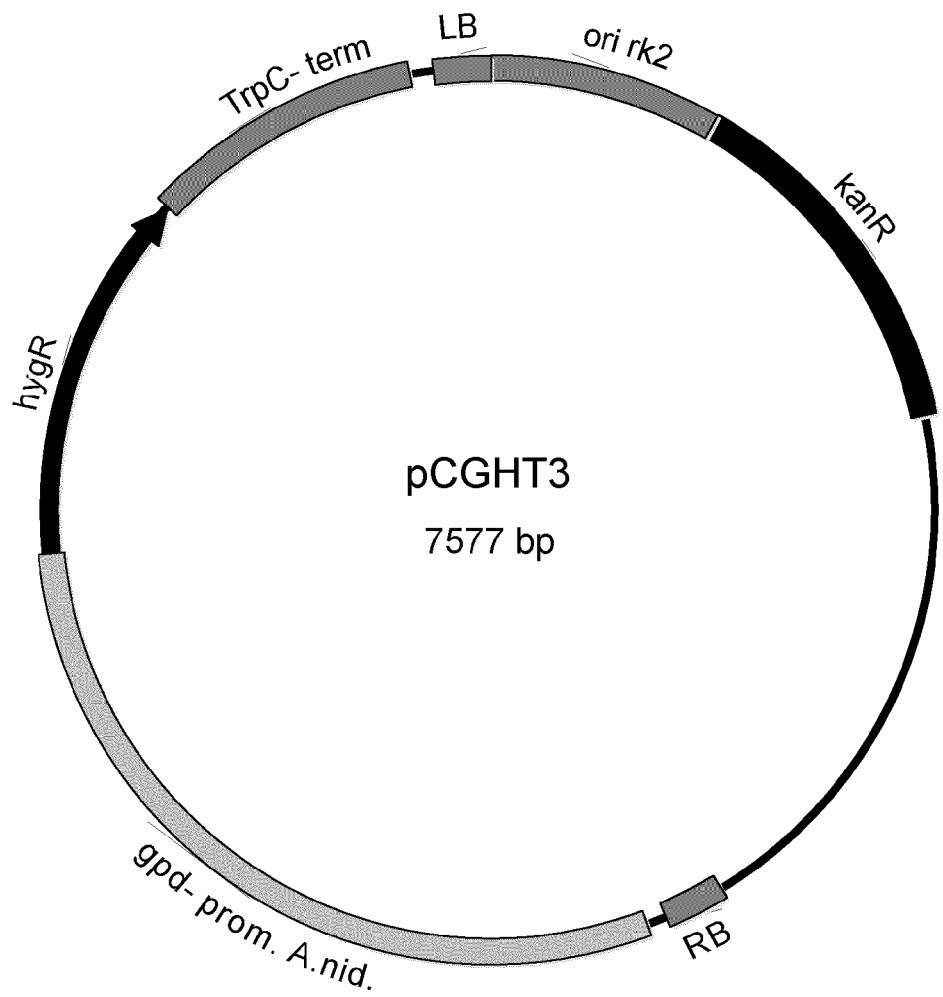
FIG. 3 illustrates the pCGHT3 transformation vector, for use in the transformation of Monascus strains according to particular embodiments of the invention.

This smaller vector is a derivative of the pUR5750 and is coded pCB301 (Xiang et al. 1999). Typical DNA elements necessary for plant transformation, the original function of the basic sequence of pUR5750, have been removed from this plasmid leaving a 3574 bp vector. FIG. 3 shows the pCB301 containing the Hpt cassette called pCGHT3 ("RB"=right border; "LB"=left border; "Hpt"=hygromycin phosphotransferase gene). This vector is half the size of the original Hpt vector.

In order to be able to use a selectable marker like the Ble or the NptII gene we first confirmed inability of *Monascus ruber* to grow in media containing concentrations of Zeocin or G418 mostly used in fungal transformation systems. Conidia and spores from *Monascus ruber* strain LF4 and LF6 were not able to grow on PDA plates containing 600 µg/ml Zeocin or 200 µg/ml G418.

Using the two basic vectors and three selectable markers six vectors were made (Table 3).

TABLE 3

The vector constructs made

| Basic vector | Marker gene | Construct |
| --- | --- | --- |
| pUR5750 | Hpt | pURGHT2 |
|  | Ble | pURGBT1 |
|  | NptII | pURNT3 |

TABLE 3-continued

The vector constructs made

| Basic vector | Marker gene | Construct |
|---|---|---|
| pCB301 | Hpt | pCGHT3 |
| | Ble | pCGBT2 |
| | NptII | pCGNT13 | d) Transformation with the Six Newly Constructed Vectors

A mixture of conidia and ascospores from *M. ruber* strain LF5 was transformed with the six vectors as described before. After the cocultivation step the filters with the outgrowing conidia and ascospores were transferred to selective plates.

The selective plates contain YM-medium with 200 µM cefotaxime to kill the *Agrobacterium* cells and either 100 µg/ml Hygromycin, or 200 µg/ml Zeocin, or 200 µg/ml Geneticin to select for transformants.

After approx. 12 days the first growing colonies became visible on the selective plates.

Table 4 shows the score of the transformants.

TABLE 4

Transformants obtained from LF5 conidia.

| Vector | Marker gene | No. of transformants |
|---|---|---|
| pURGHT2 | Hpt | 7 |
| pURGBT1 | Ble | 0* |
| pURGNT3 | NptII | 1 |
| pCGHT3 | Hpt | 18 |
| pCGBT2 | Ble | 0* |
| pCGNT3 | NptII | 9 |

*General disperse growth, no specific colonies visible.

Colonies were transferred to PDA plates with appropriate antibiotics and after sufficient growth used as an inoculum for growth in liquid medium (YPD) containing the antibiotic. Mycelium was harvested after 4 days and DNA was isolated.

In order to establish the integration of the selectable marker gene in the genome from the *M. ruber* LF5 transformants two PCR analysis were performed on a number of transformants. The first analysis which will show the presence of the selectable marker in the isolated DNA is a PCR with primers specific for the marker genes. The second PCR analysis which excluded the presence of contaminating vector DNA, possibly coming from surviving *A. tumefaciens* bacteria, was performed with primers specific for the *A. tumefaciens* GPD (glyceraldehyde phosphate dehydrogenase) gene.

In conclusion it has been shown that Hpt and NptII vectors which have been constructed according to the cassette strategy are effective in transforming *M. ruber*. Using the smaller pCB301 based vector seems to result in more transformants than the pUR5750 based ones. PCR analysis shows integration of the selectable marker genes in the genome of *M. ruber* and also shows that *A. tumefaciens* bacteria have efficiently been killed by the Cefotaxim.

II. Transformation with a LDH Gene a) Vector Construction

For the introduction of at least one copy of the Bovine (*Bos taurus*) LDH gene in the genome of the *Monascus ruber* strains, the most straightforward approach is introducing a codon optimized Bovine LDH gene in the cassette as described hereabove. The promoter and terminator sequences driving the expression of the LDH gene will be the same has those driving the selectable marker gene.

For codon optimization we first analyzed the codon usage of *Monascus*. Since only two genes from *M. ruber* are available we compared the codon usage of *M. pilosus* and *M. purpureus* with the codon usage of the *M. ruber* genes. The three species are closely related and a great deal of similarity between the codon preference of the three *Monascus* species was found.

Figure 5:
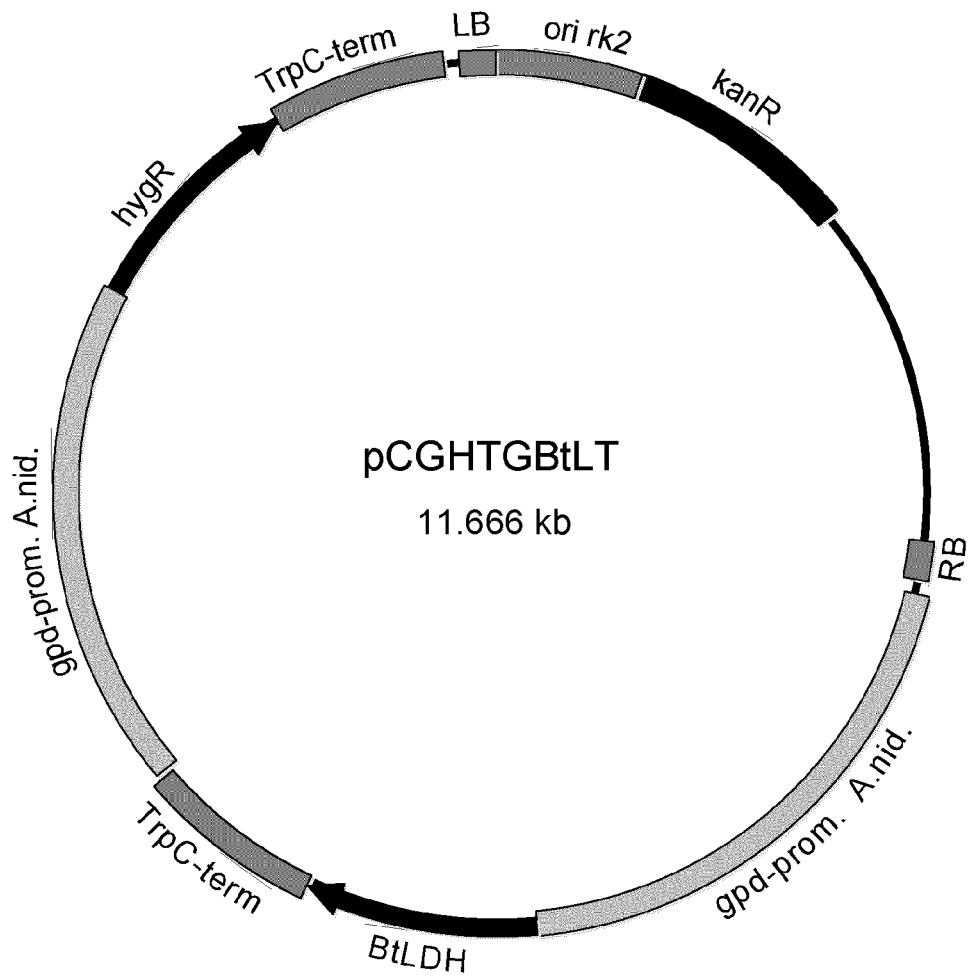
FIG. 5 illustrates transformation vector pCGHTGBtLT with the codon optimized (Bos taurus Bt) LDH gene, according to a particular embodiment of the invention.
Figure 6:
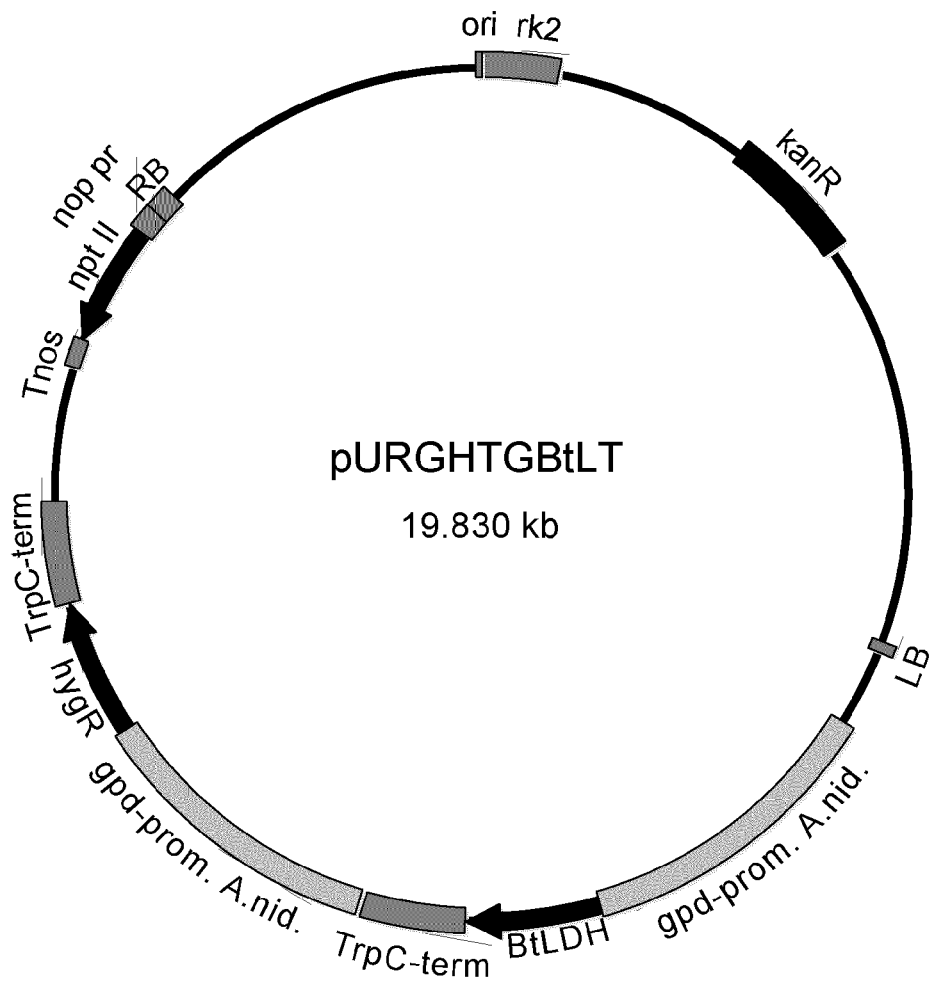
FIG. 6 illustrate transformation vector pURGHTGBtLT with the codon optimized (Bos taurus Bt) LDH gene based on the pUR5750 plasmid according to a particular embodiment of the invention.

Based on the codon usage we were able to design a optimized Bovine LDH gene for expression in the *M. ruber* strains selected (SEQ ID NO:1 and FIG. 4) and had such a gene synthesized by Genscript Corporation. After obtaining this gene it was cloned into both type of Hpt vectors constructed and tested. The cloning was performed according to the cassette strategy shown in FIG. 2 which has the advantage that the original vector is unchanged except for the insertion of the promoter-LDH-terminator cassette. This results in vectors pCGHTGBtLT based on the pCB301 plasmid (FIG. 5) and pURGHTGBtLT based on the pUR5750 plasmid (FIG. 6).

b) Cloning and Expression of the Bt-LDH Gene in *E. coli*.

In order to confirm the correct translation and the activity of the synthetic LDH gene used for transforming *M. ruber*, the gene was cloned in an *E. coli* expression vector. The expression vector used is the InVitrogen pBAD102 vector which will express the protein after Arabinose induction.

LDH was highly expressed in *E. coli* but was found to be partly soluble.

The soluble *E. coli* proteins were used to analyse the LDH enzyme activity.

The reaction catalyzed by the btLDH is:

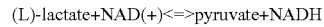

(L)-lactate+NAD(+)<=>pyruvate+NADH

In the activity assay an excess of pyruvate and NADH is added so the activity is reflected by the conversion of NADH to NAD which can spectrofotometrically be measured at 340 nM.

As a positive control LDH enzyme obtained from Sigma-Aldrich was used.

The reaction velocity was determined by a decrease in absorbance at 340 nm resulting from the oxidation of NADH. One unit causes the oxidation of one micromole of NADH per minute at 25° C. and pH 7.3, under the specified conditions.

0.2 M Tris HCl buffer was prepared. The LDH enzyme was diluted prior to use to obtain a rate of 0.02-0.04 ΔA/min. in Tris buffer and kept cold.

A reaction mix of 2.8 mL Tris.HCl, 0.2 M pH 7.3 and 0.1 mL 6.6 mM NADH was prepared.

LDH activity was measured with and without substrate added, in order to monitor background NADH conversion.

Figure 7:
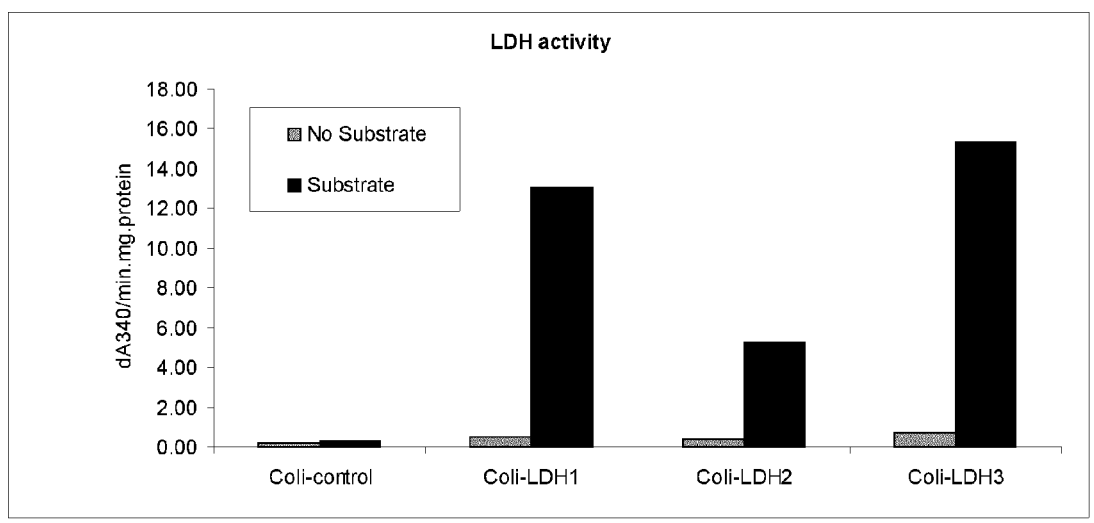
FIG. 7 illustrates LDH activity in E. coli protein extracts after expression of the synthetic LDH gene, according to a particular embodiment of the invention.

The analysis of the expression and activity of the synthetic LDH in *E. coli* shows that the synthetic gene encodes a protein of the correct Mw and with LDH activity. The glucose and lactose production by these *E. coli* strains over time are shown in FIG. 7 ("Coli-LDH 1, 2, and 3" correspond to three independent *E. coli* extracts with the expressed synthetic LDH protein present; "Coli-control" is an *E. coli* extract expressing a different protein).

c) Transformation of *Monascus ruber* with the LDH Vectors.

A mixture of conidia and ascospores from *M. ruber* strains LF4, LF5 or LF6 was used for transformation with the LDH vectors pCGHTGBtLT and pURGHTGBtLT. So in total 6 transformations were performed. After applying the transformation procedure as described before and selection on hygromycin containing plates only three LF5 transformants were obtained.

One transformant resulted from the use of the pCGHTG-BtLT vector (LF5-t1) and two from the pURGHTGBtLT vector (LF512, LF5-t5).

d) Analysis of *M. ruber* LF5-T1 and LF5-T2-LDH Transformants

In a first experiment, two transformants LF5-T1 and LF5-T2 were analysed.

LF5-T1 was transformed with pCGHTGBtLT, and LF5-T2 with pURGHTGBtLT.

In order to analyze the LDH enzyme activity and possible L-lactate production the two transformants and the wt-LF5 strain were grown in S.c. medium+50 g/L glucose pH 6.0.

Medium and biomass samples were taken from individual cultures after 24, 48, and 72 hours of cultivation.

(i) Glucose Consumption and Lactate Production

FIGS. 8a and 8b clearly show glucose consumption in all cultures while in the medium from LF5-T2 lactic acid is detected increasing in concentration with time (the numbers 24, 48 and 72 indicate samples from two separate cultures grown for 24, 48 and 72 hours; "M" corresponds to medium). LF5-T2 consumed approximately 8 g/L glucose and produced approximately 1.5 to 2 g/L of lactic acid, indicating a yield between 0.18 and 0.25 g/g was reached. The maximum theoretical yield is 1.00 g/g.

(ii) Enzymatic Analysis

Since the HPLC analysis does not discriminate between L- and D-lactic acid a number of samples was analyzed by an enzymatic method. A L-lactic acid analysis kit (Megazyme) confirmed the presence of L-lactic acid in the LF5-T2 samples (FIG. 9).

The harvested biomass samples were frozen in liquid nitrogen and ground using a mortar and a pestle. The frozen powder was thawed in buffer (0.2 M Tris.HCl, pH 7.3) and the protein was extracted by vortexing. After centrifugation the supernatant was subjected to protein analysis and to an LDH-enzyme activity analysis as described in the previous paragraph.

Figure 9:
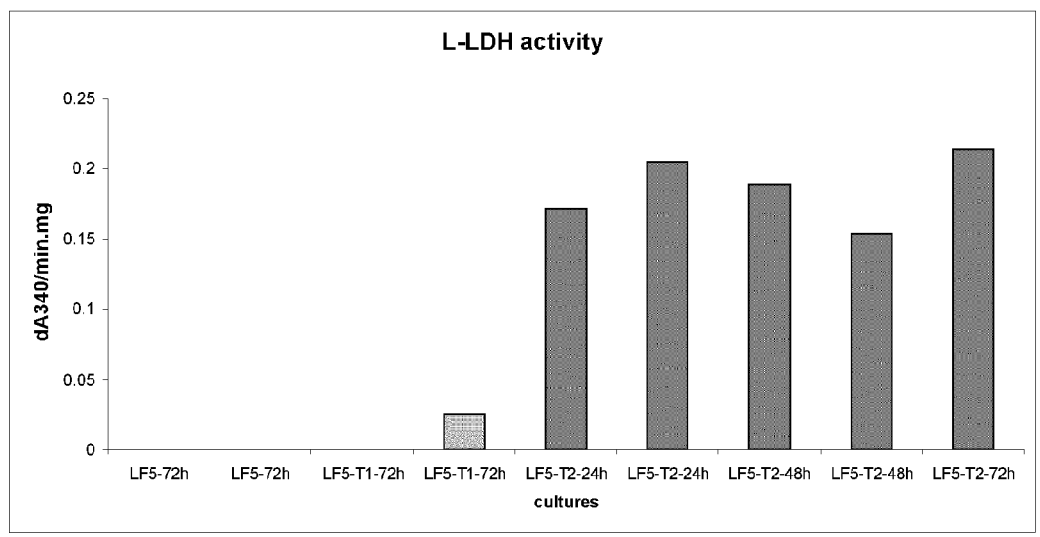
FIG. 9 illustrates the L-LDH enzyme activity in the biomass of the two transformants LF5-T1 and LF5-T2 and the untransformed M. ruber control LF5 according to particular embodiments of the invention.

This analysis clearly showed the presence of L-LDH activity in the LF5-T2 transformant, whereas no activity was found in the control (FIG. 9).

(iii) Southern Blot Analysis

Hybridization was performed using the LDH gene. Southern blot analysis confirms a single integration of the LDH gene in the genome of the *M. ruber* transformant t2, after growth in non selective medium.

Transformant t1 was found not to contain the LDH gene. A second Southern analysis with the hygromycin gene shows integration of the hygromycin gene in both transformants. This indicates that in transformant t1, the gene cassettes, LDH and hygromycin between both borders was not completely integrated.

(iv) Conclusion

Using the transformation vectors constructed with a combination of a selectable marker and a synthetic LDH gene 27 *M. ruber* transformants were obtained. One transformant, LF5-T2 shows production of lactic acid when grown on glucose medium.

Lactic acid production, L-LDH activity and southern blots support the conclusion that we have inserted an L-LDH encoding heterologous gene in the genome of this *M. ruber* LF5-T2 transformant in such a way that it is expressed and metabolically active.

e) Analysis of *M. ruber* LF4-, LF5-, and LF6-LDH Transformants

In a next experiment, a total of 35 transformants were analyzed, i.e. 4 of LF4, 16 of LF5 and 15 of LF6. Strains were precultured in 10 ml YEPD medium for 3 days. Biomass was washed in Sc medium with 10 g/L glucose at pH 2.8 and was cultivated in 15 ml of Sc medium with same composition. The glucose consumption by the strains in illustrated in FIG. 10.

Figure 10:
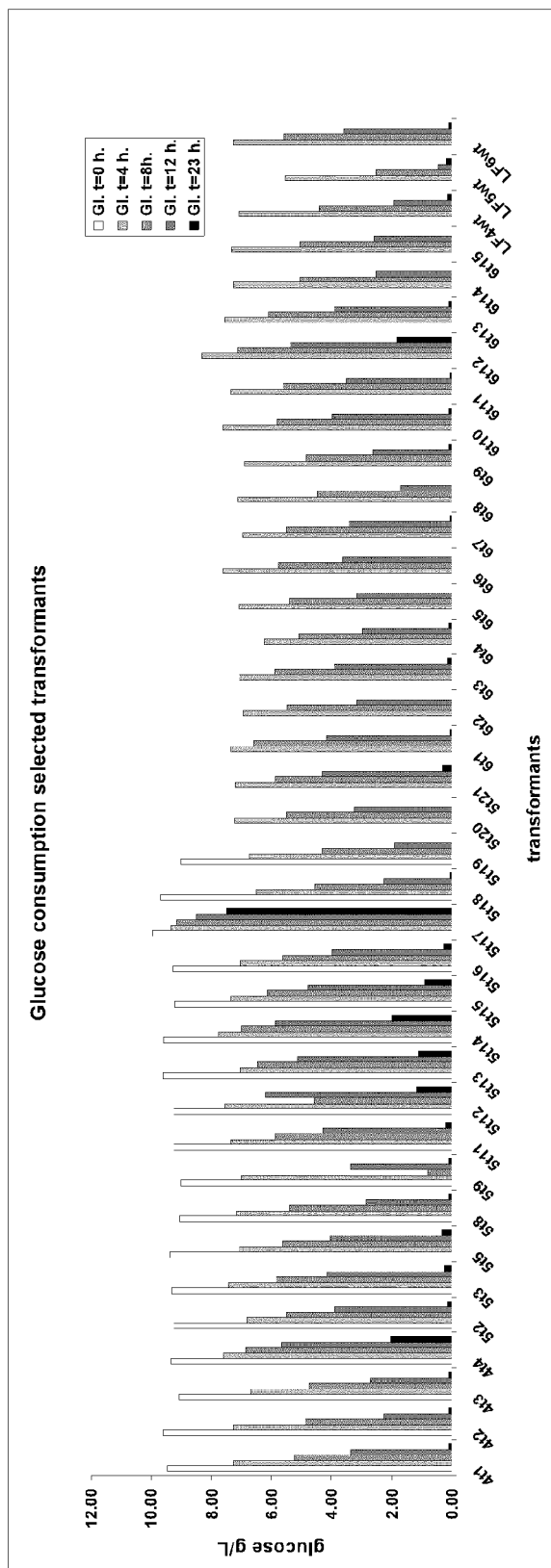
FIG. 10 illustrates the consumption of glucose by transformants and wild types of strains LF4, LF5 and LF6, according to particular embodiments of the invention.
Figure 11:
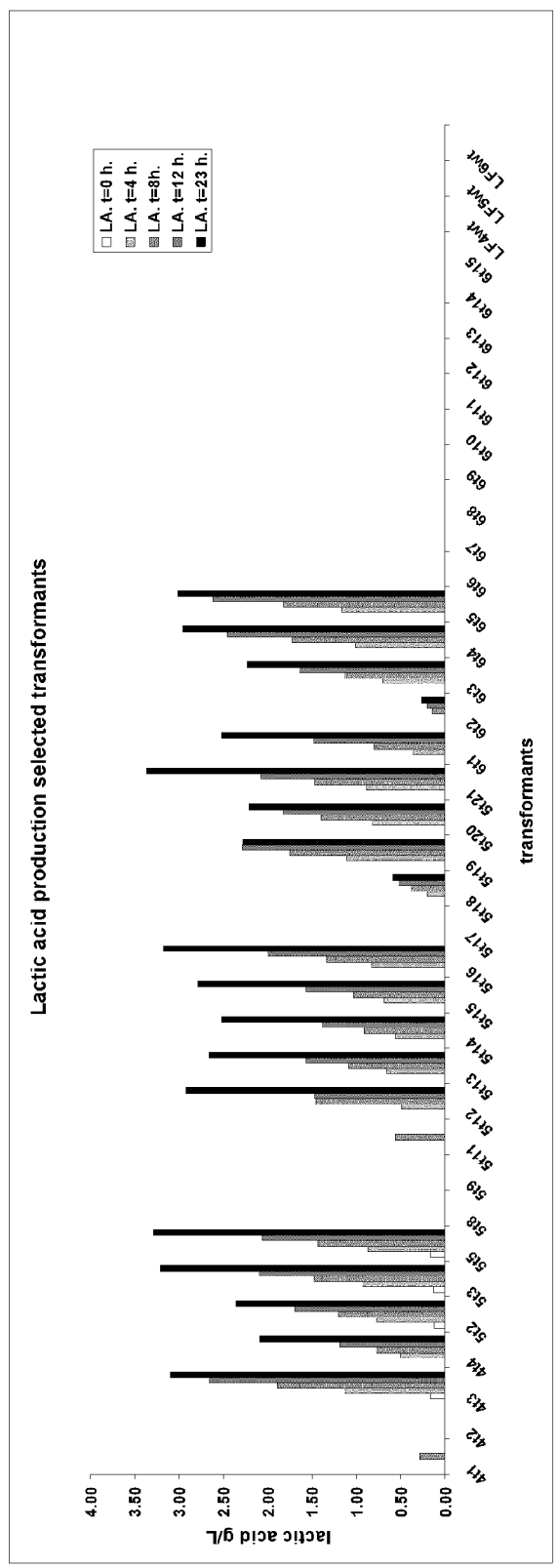
FIG. 11 illustrates the production of lactic acid by transformants and wild types of strains LF4, LF5 and LF6 according to particular embodiments of the invention.
Figure 12:
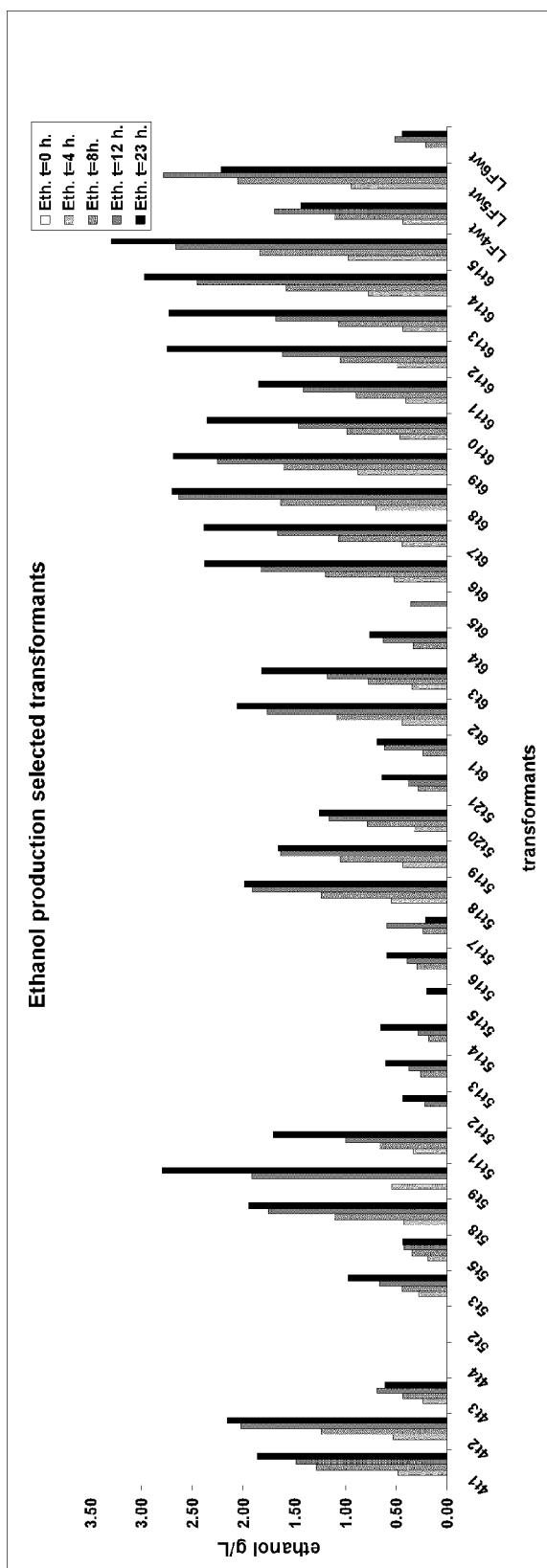
FIG. 12 Production of ethanol by transformants and wild types of strains LF4, LF5 and LF6. Strains were precultured in 10 ml YEPD medium for 3 days.

Nineteen (54%) of these transformants, i.e. two derived from LF4, twelve derived from LF5 and five derived from LF6, produced lactic acid from glucose (FIG. 10). In the positive experiments, varying amounts of lactic acid were found, ranging from 0.5 to 3.3 g/L, corresponding to 5-33% of the maximal theoretical yield (FIG. 11). Ethanol was formed as byproduct, its concentration inversely related to the lactic acid concentration (FIG. 12).

Two transformants of each strain were selected (4t3, 4t4, 5t2, 5t21, 6t4, 6t5), the one with the highest lactic acid production and one with the lowest ethanol production. The strains were subsequently cultivated in shake flasks (on either glucose or xylose (both 10 g/L)), under two different aeration conditions: aerobic and severely oxygen limited.

Figure 13:
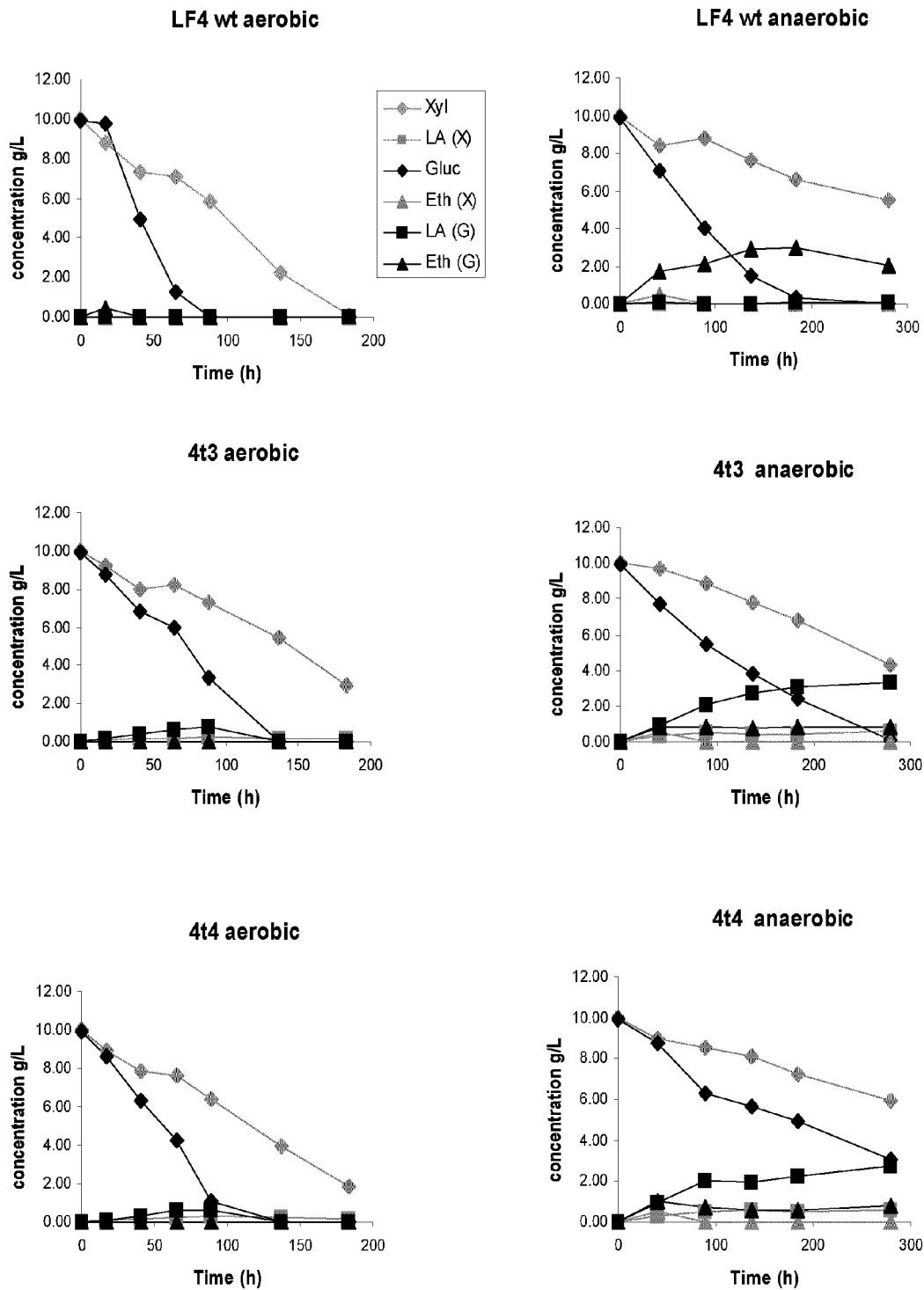
FIG. 13 illustrates the sugar (glucose or xylose) consumption and product (ethanol and lactic acid) formation by transformants and wild type strains of LF4 under aerobic and anaerobic conditions, according to particular embodiments of the invention.
Figure 14:
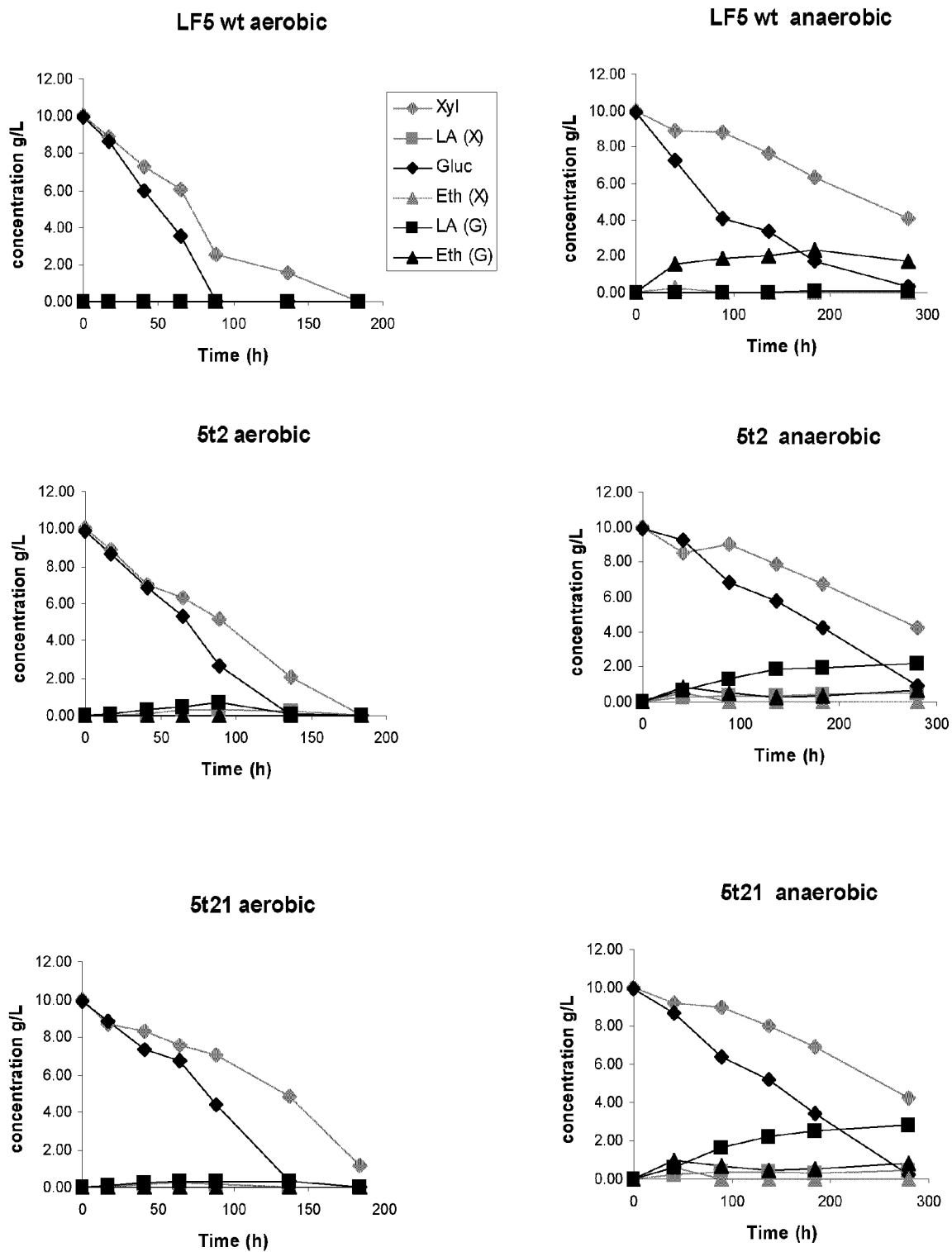
FIG. 14 illustrates the sugar (glucose or xylose) consumption and product (ethanol and lactic acid) formation by transformants and wild type strains of LF5 under severely aerobic and anaerobic conditions, according to particular embodiments of the invention.
Figure 15:
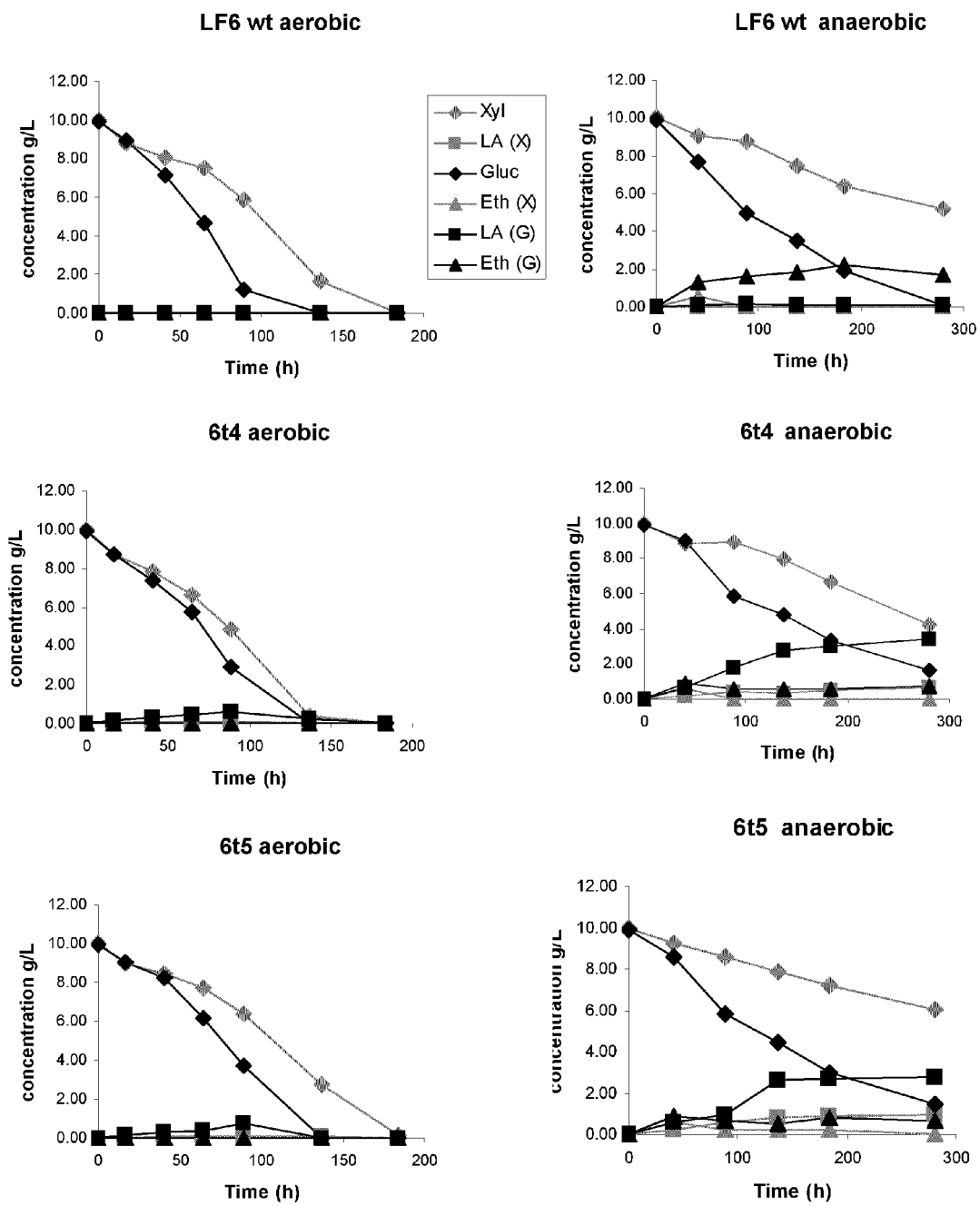
FIG. 15 illustrates the sugar (glucose or xylose) consumption and product (ethanol and lactic acid) formation by transformants and wild type strains of LF6 under severely aerobic and anaerobic conditions, according to particular embodiments of the invention.

Under aerobic conditions, strains were precultured in 100 ml shake flasks on 10 ml YEPD for three days. The cultures were then washed twice with 25 ml Sc medium, at pH 2.8. Biomass was homogenized in 10 ml of the same medium using a triangular magnetic stirring rod. 750 microliters were used to inoculate 15 ml of Sc medium, pH 2.8, containing 10 g/L of glucose or xylose (FIGS. 13-15).

Alternatively, under severely oxygen limited conditions, cultures were performed in bottles closed with an aluminium capped butyl rubber stopper equipped with bicycle tube valves to create severely oxygen limited, almost anaerobic conditions. Precultured in 100 ml shake flasks on 10 ml YEPD during 3 days. The cultures were then washed twice with 25 ml S.c medium, at pH 2.8. Biomass was homogenized in 10 ml of same medium using a triangular magnetic stirring rod. 750 microliters were used to inoculate 15 ml of Sc medium, pH 2.8, containing 10 g/L of glucose or xylose.

In the aerobic cultures (left panels of FIGS. 13-15) some lactic acid was produced (approximately 0.5-1 g/L) from glucose. The lactic acid was consumed after the glucose was fully consumed. No ethanol was formed. Under severely oxygen limited conditions (right panels of FIGS. 13-15) the lactic acid concentration was between 2.0 and 3.3 g/L, and ethanol was produced at concentrations varying between 0.5 and 1.0 g/L.

Example 3

Further Improvement of Lactic Acid Yield by Eliminating Ethanol Production a) Identification of the Pyruvate Decarboxylase Genes Using Sequence Homology In order to further improve lactic acid yield a gene knock-out system was envisaged to reduce the production of products other than lactic acid on the one hand and to reduce the metabolism of lactic acid by *Monascus* on the other hand. More particularly, in order to avoid the production of alcohol, a knock-out system was envisaged based on genes encoding *M. ruber* homologues of the *S. cerevisiae* PDC1 gene encoding pyruvate decarboxylase (EC 4.1.1.1).

*M. ruber* produces ethanol under oxygen-limited conditions. Since both ethanol and lactic acid are produced from pyruvate, the production of ethanol should be prevented since it decreases the yield of lactic acid.

Using BLAST with the *S. cerevisiae* PDC1 gene as the query we found several homologues in the *Aspergillus niger* genome which could represent a PDC encoding gene. *A. niger* was used because of its close relationship to *Monascus*. Based on these sequences we designed degenerated PCR primers in order to be able to clone part of a *M. ruber* PDC.

RT-PCR on RNA from *M. ruber* strain LF6 resulted in two 1.3 kB DNA fragments which were cloned in a plasmid.

Sequencing of these cloned PCR fragments confirmed the presence of two open reading frames with high homology to the *Aspergillus niger* PDC homologues and sufficient homology to the *S. cerevisiae* PDC1 gene to conclude that we have cloned two PDC1 analogues of *Monascus ruber*.

The open reading frame for the *M. ruber* PDC genes PDC1 and PDC2 is provided as SEQ ID NO:3 and 4 (and FIGS. 16 and 17).

b) Construction of a Gene Knock-Out Vector.

i) Knock-Out of PDC Genes

Figure 18:
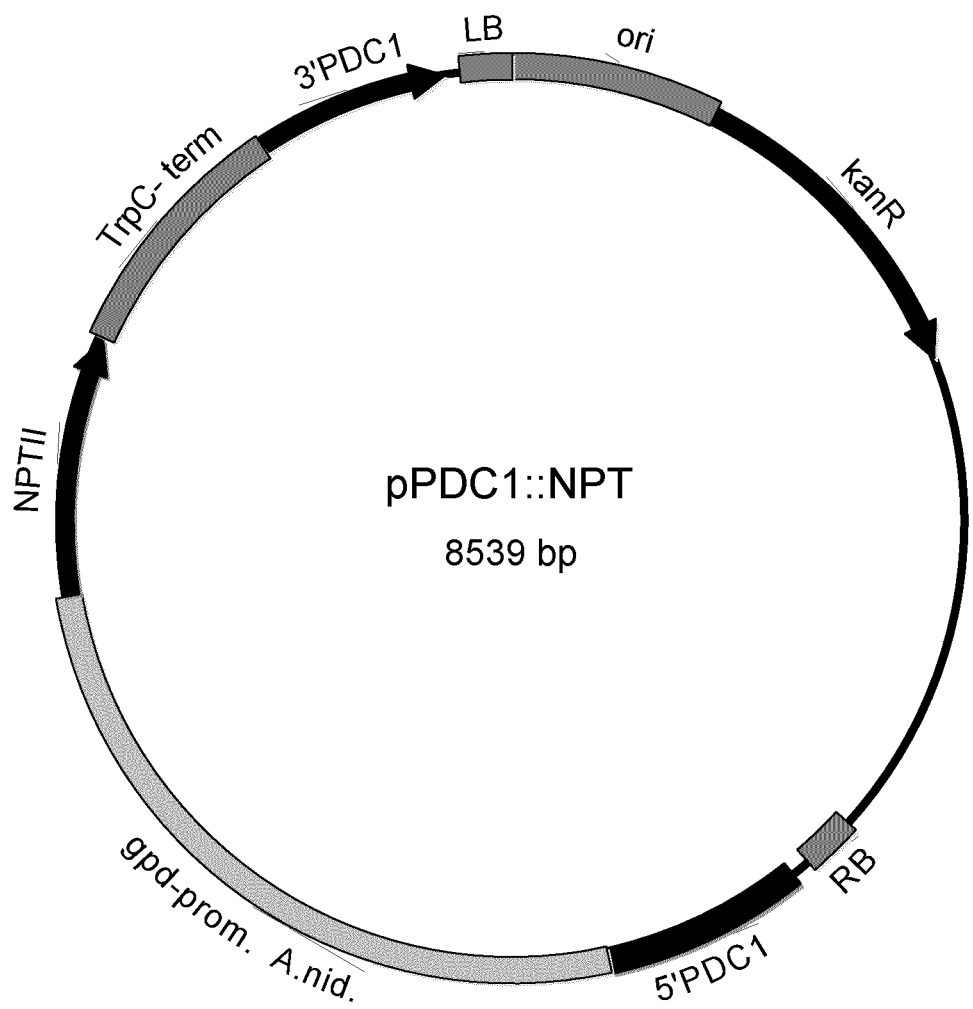
FIG. 18 illustrates an example of a transformation vector which can be used for the disruption of PDC1 of Monascus strains using geneticin selection according to particular embodiments of the invention.
Figure 19:
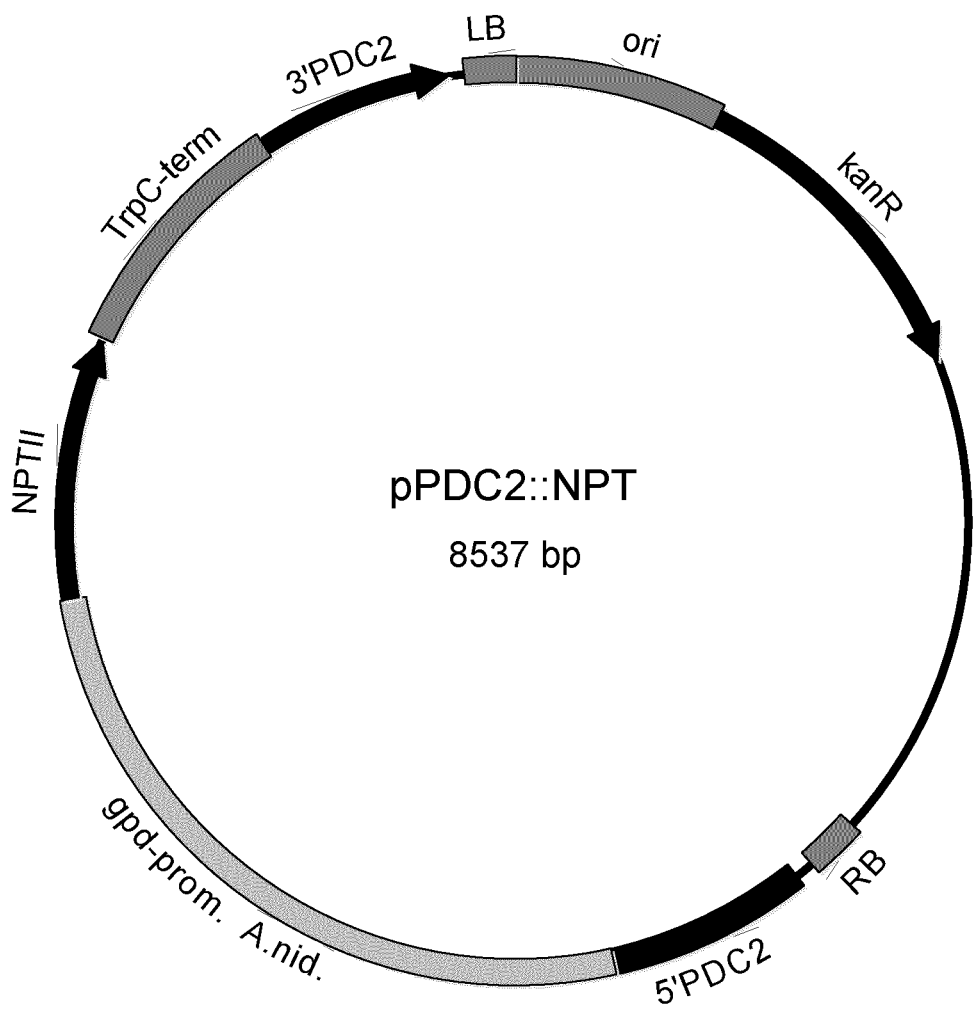
FIG. 19 illustrates an example of a transformation vector which can be used for the disruption of PDC2 of *Monascus* strains using geneticin selection according to particular embodiments of the invention.
Figure 20:
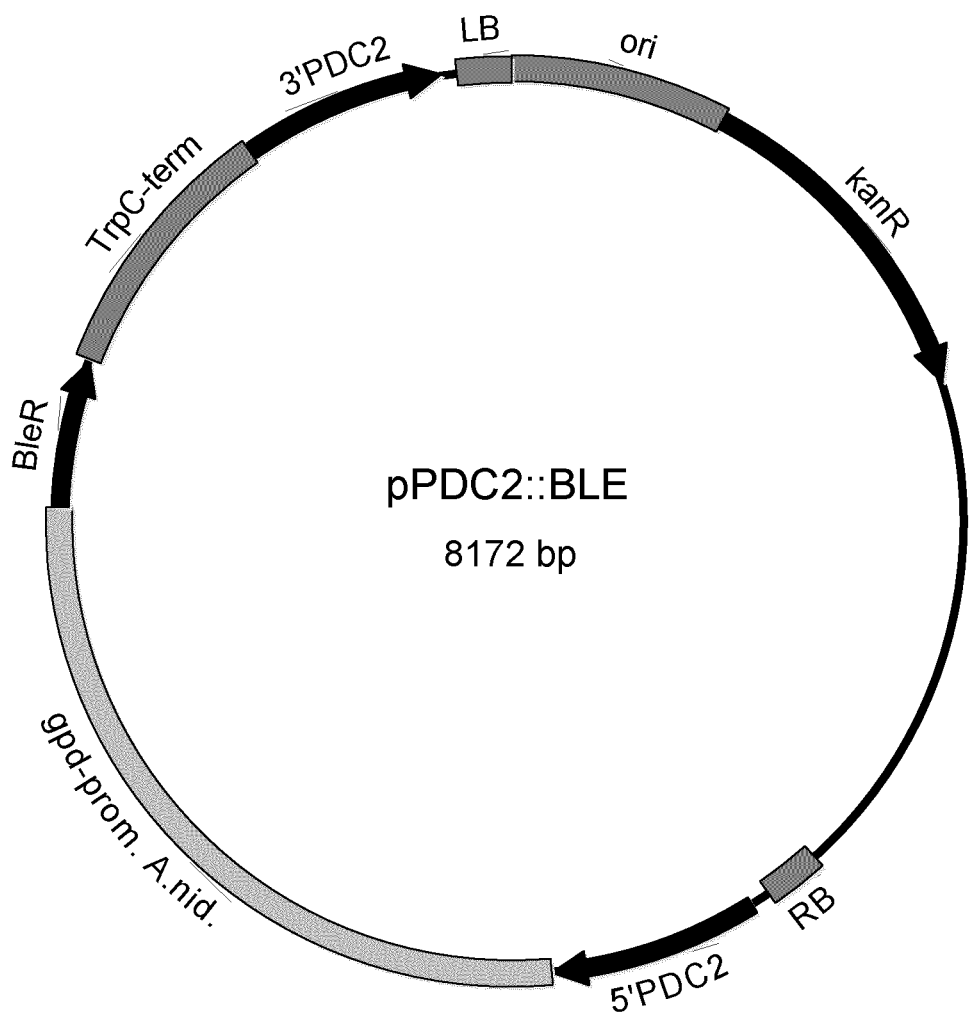
FIG. 20 illustrates an example of a transformation vector which can be used for the disruption of PDC2 of *Monascus* strains using zeocin selection according to particular embodiments of the invention.

Using PCR, the 5' and 3' halves of the PDC1 and PDC2 genes were isolated and suitable restriction sites are added to the ends. The 5' halves are then cloned 5' of the promoter-marker-terminator cassette of vectors pCGNT1 and pCGBT2 (and 3' of the Right Border sequence). These vectors are identical to the previously described vector pCGHT3, except that the NPTII and BLE genes are used as selectable markers instead of the HPT gene. Likewise, the corresponding 3' halves are cloned 3' of the promoter-marker-terminator cassette (and 5' of the Right Border sequence). In this manner, three vectors are generated:

1. pPDC1::NPT for disruption of PDC1 using geneticin selection (FIG. 18)
2. pPDC2::NPT for disruption of PDC2 using geneticin selection (FIG. 19)
3. pPDC2::BLE for disruption of PDC2 using zeocin selection (FIG. 20)

Figure 21:
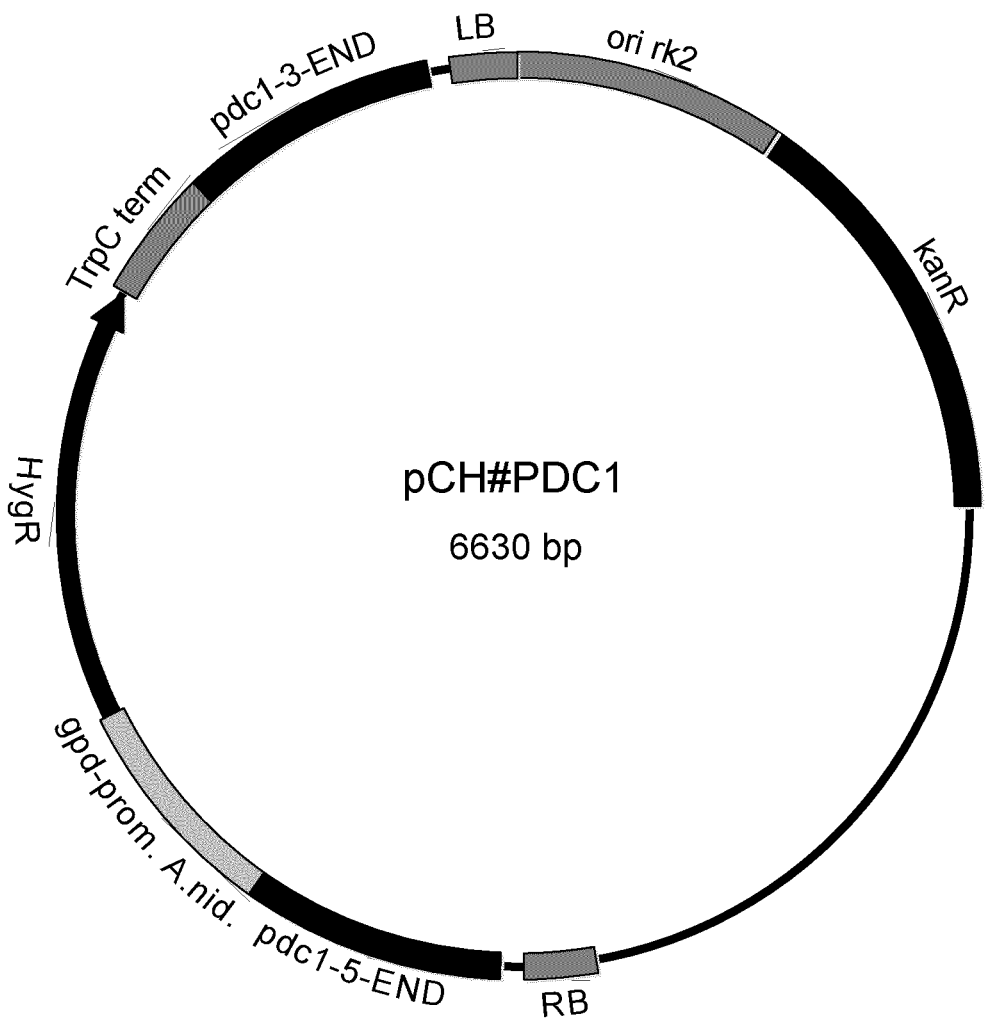
FIG. 21 provides a schematic representation of vector pCH#PDC1 used to disrupt the PDC1 gene.
Figure 22:
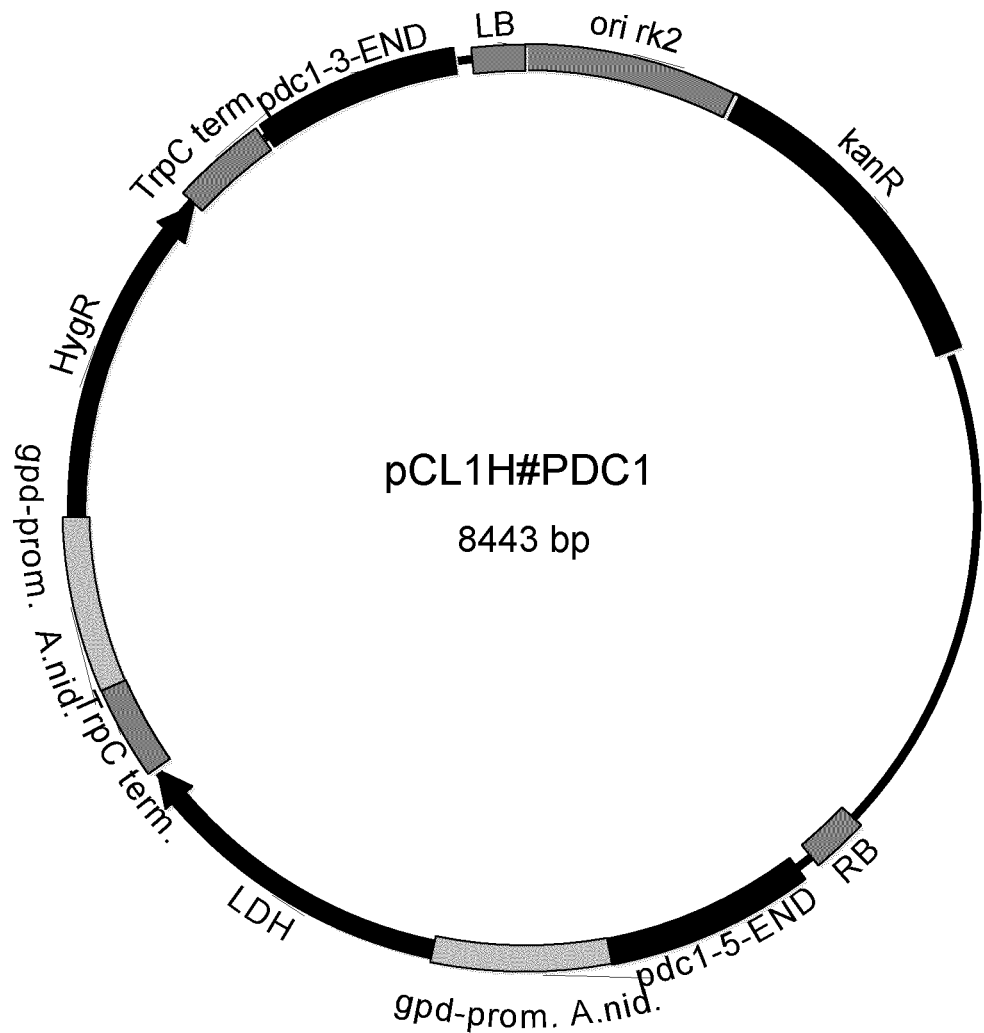
FIG. 22 provides a schematic representation of vector pCL1H#PDC1 used to disrupt the PDC1 gene and insert the LDH gene simultaneously.
Figure 23:
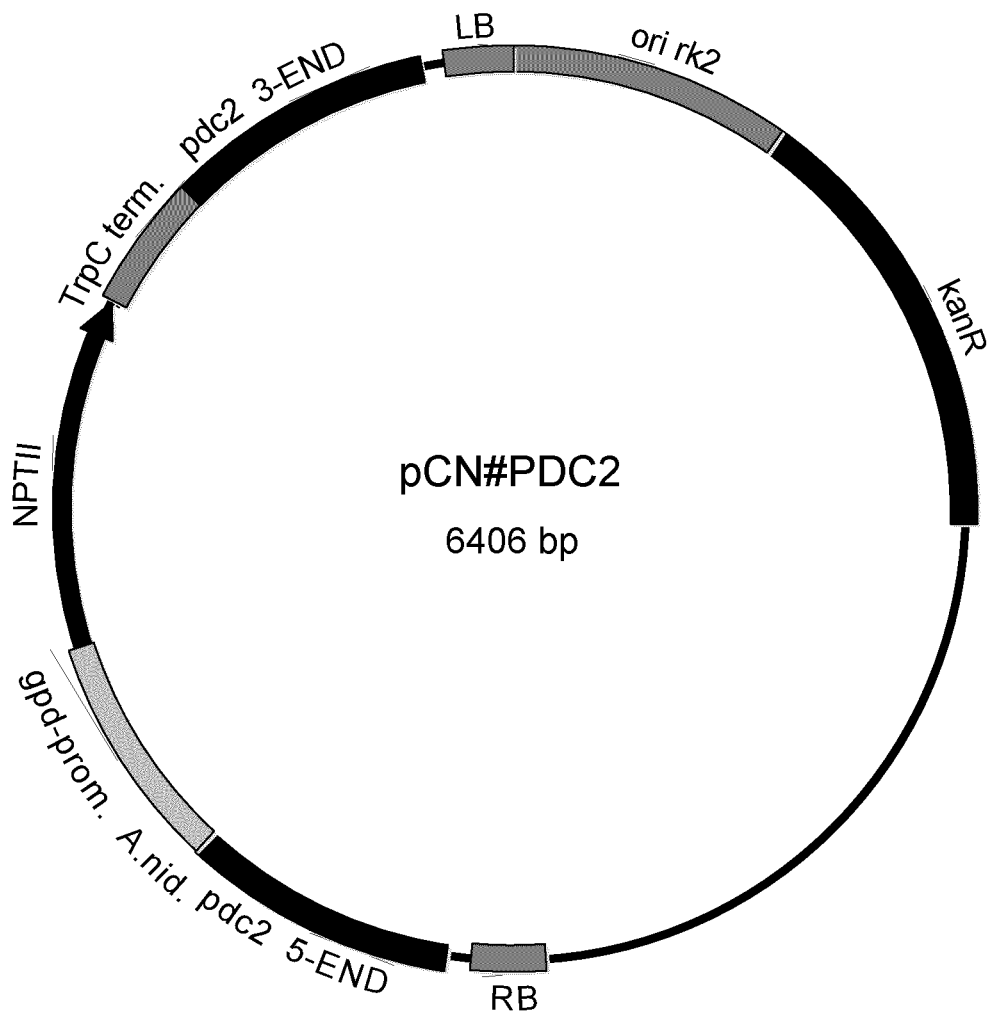
FIG. 23 provides a schematic representation of vector pCN#PDC2 used to disrupt the PDC2 gene in a PDC1-LDH+ transformant.

These vectors are used in a previously constructed PDC1::NPT disruptant ii) Combined Knock Out and Gene Insertion Vectors were constructed to enable simultaneous disruption of a target gene and introduction of another gene. In order to minimize unwanted recombination in a second round of transformation due to the presence of long stretches of DNA in the vector and in order to increase the cloning efficiency during vector construction the size of the promoter and terminator sequences were reduced in the new vectors. Using PCR the size of the GPD promoter was reduced from 2208 bp to 538 bp and the TrpC terminator was reduced from 763 bp to 278 bp. These are vector pCH#PDC1 and vector pCL1H#PDC1 (see FIGS. 21 and 22). The pCH#PDC1 vector is used for the disruption of PDC1 using hygromycin selection. The pCL1H#PDC1 vector is used for the disruption of PDC1 and introduction of LDH using hygromycin selection. Transformants resulting from these vectors have a disrupted PDC1 gene and a disrupted PDC1 gene+an inserted LDH gene respectively. The vector pCN#PDC2 was constructed to disrupt the PDC2 gene using geneticin selection (FIG. 23).

c) Generating Knock-Out Transformants i) Knock-Out of PDC Genes

Spores obtained from LF6 LDH transformant t4 and t5 are used in transformation experiments with the knock out vectors pPDC1::NPT or pPDC2::NPT. After selection on G418 (geneticin) each combination of strain and vector results in 50-80 geneticin resistant colonies. By means of PCR with gene specific primers the DNA of 40 transformants (20 LF6t4+pPDC2::NPT transformants and 20 LF6t5+pPDC2::NPT transformants) are tested for the presence of the NPTII gene and for the disruption of the PDC2 gene. Disruption of the PDC2 gene with the knock out vector is observed.

ii) Combined Knock Out and Gene Insertion

The vectors pCH#PDC1 and pCL1H#PDC1 were used to transform the spores, collected from the wild type strain LF6 at 40° C., according to our standard procedure. After 10 days of growth on selective plates containing hygromycin growing colonies were observed and 20 of them were transferred to new hygromycin containing plates and tested by PCR for PDC1 gene knock out.

PCR analysis shows that in 1 out the 20 transformants from pCH#PDC1 and in 3 out of 20 transformants from pCL1#PDC1 the PDC1 gene has been disrupted (Table 6).

TABLE 5

| construct | Number of transformant per construct | | |
|---|---|---|---|
| | Colonies total | Colonies transferred | PDC1 knockout |
| pCH#PDC1 | 53 | 20 | 1 |
| pCL1H#PDC1 | 97 | 20 | 3 |

The vector pCN#PDC2 was used to transform spores from a PDC1 knock out strain from transformation round 1. After 10 days of growth on selective plates containing geneticin growing several colonies were observed and 40 of them were transferred to new geneticin containing plates and tested by PCR for PDC2 gene knock out.

Strain LF6KL19 was confirmed to be a double knockout of PDC1 and PDC2 and contains the recombinant LDH gene.

c) Analysis of Transformants

Strain LF6KL19 was precultivated in 300 ml Sc medium containing 50 g/l glucose and 1 g/l Junlon in a 2 L Erlenmeyer at pH 2.8. The initial spore concentration was 1×105 spores/ml. The incubation temperature was 30 or 35° C. and agitation speed was set at 75 rpm. At 30° C. 16.1 g/l glucose was consumed and 14.4 g/l lactic acid was produced, at 35 18.8 g/l of glucose was consumed and 18.6 g/l lactic acid was produced, indicating the actual yield was between 0.9 and 1.0 g/g. Under these conditions also the highest productivities were obtained: 0.15 g/l/h.

d) Genome and Transcriptome Analysis

The genome of *M. ruber* LF6 and the transcriptomes of *M. ruber* LF6 and *M. ruber* LF6KL19 (double PDC knock-out, introduced copy of bovine LDH), growing on different growth substrates, were sequenced and the relevant genes involved in alcohol production were identified on the genome by an automated annotation procedure. The RNA sequence data were used to improve the architecture of these genes. Many putative genes that are involved in the formation of ethanol were identified on the genome: 7 for pyruvate decarboxylases (PDCs) and 12 for alcohol dehydrogenases. 3 putative PDC genes were adjacent to each other in the genome, Analysis of the RNA sequence data showed that these 3 putative PDC genes belong to one single gene. The PDC2 product (SEQ ID NO:2) was identical to part of the translated sequence of this gene.

The PDC1 product was identical to part of the putative PDC gene product of Mona10180. Both genes encoding PDC1 and PDC2 were highly expressed under all circumstances. Besides these, also another PDC gene (Mona07809 or PDC4, SEQ ID NO: 5, FIG. 24) was transcribed under all circumstances and can be eliminated from the genome of *M. ruber* to reduce the production of ethanol.

Example 4

Further Improvement of Lactic Acid Yield by Eliminating of Endogenous Lactic Acid Metabolism a) Cyt-LDH Activity Analysis in *M. Ruber*

From literature it is known that in fungi and yeasts lactic acid is metabolized by a (cytochrome)L-lactate dehydrogenase. Therefore we first analyzed *M. ruber* strains grown on lactic acid for this enzyme activity. *M. ruber* strains were grown on 2% yeast extract, 1% peptone medium supplemented with 5% glucose or with 2% lactic acid as carbon source. As a control *S. cerevisiae* was grown under the same conditions (Lodi and Guiard, 1991). Biomass was harvested after 24 h of growth. The harvested biomass samples were frozen in liquid nitrogen and ground using a mortar and a pestle. The frozen powder was thawed in buffer (0.067 M sodium phosphate, pH 7.4 with 0.001 M EDTA) and the protein extracted by vortexing. After centrifugation the supernatant was subjected to protein analysis and to cyt-LDH-enzyme activity analysis. The rate of reduction of potassium ferricyanide is determined spectrophotometrically at 420 nm. Prior to assay, the enzyme was dissolved in 0.067 M phosphate buffer, pH 7.4 with 0.001 M EDTA to obtain a rate of 0.02-0.04 AA/minute. A mix of 2.0 ml of 0.1 M sodium pyrophosphate, 0.5 ml of 0.5 M DL sodium lactate, 0.3 ml of 0.01 M EDTA, and 0.1 ml of potassium ferricyanide was prepared and pipetted into a micro-titer plate. 10-20 µl of appropriately diluted sample was added and the $\Delta A420/min$ was recorded.

Figure 25:
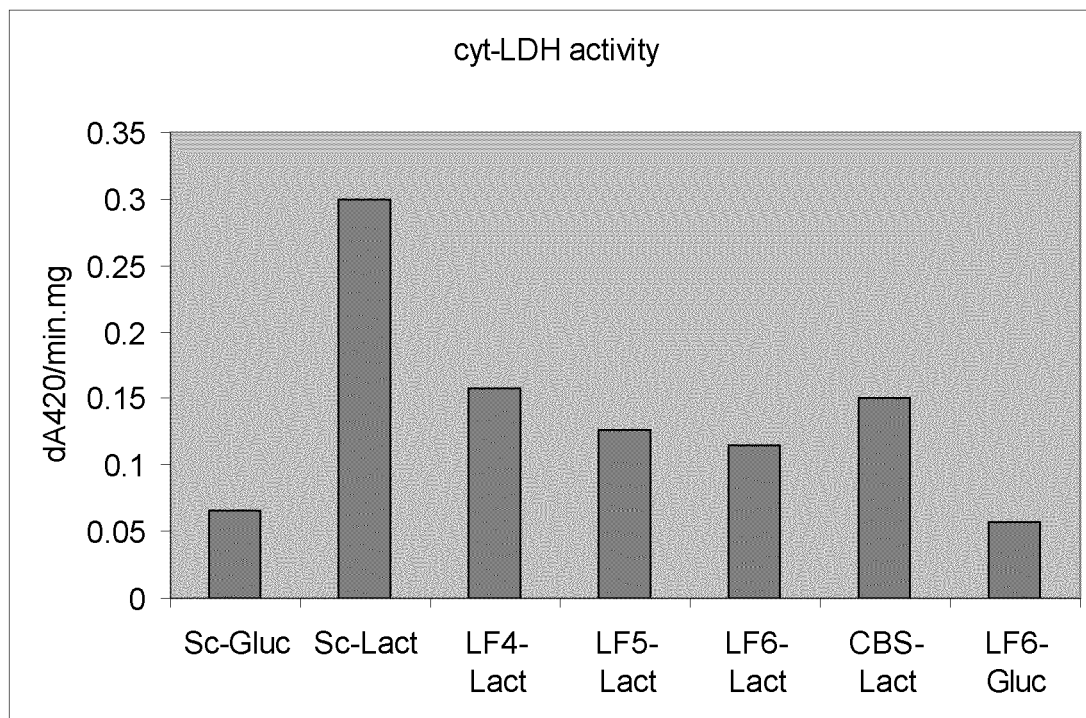
FIG. 25 illustrates Cyt-LDH activity in protein extracts from *S. cerevisiae* (Sc) and *Monascus* strains LF4, LF5, LF6, and the CBS strain, according to particular embodiments of the invention.

FIG. 25 shows the cyt-LDH activity in the protein samples. "Gluc" means grown in medium with glucose and "Lact" means grown in medium with L-lactic acid as a carbon source. Cyt-LDH activity is present in all tested *M. ruber* strains and is induced by growth on L-lactic acid as a carbon source.

b) Isolation of *M. Ruber* Homologues of the CYB2 Gene Based on Sequence Homology Using BLAST with the *S. cerevisiae* CYB2 gene as the query we found several homologues in the *Aspergillus niger* genome which could represent a cyt-LDH encoding gene. *A. niger* was used because of its close relationship to *Monascus*. Based on these sequences we designed degenerated PCR primers in order to be able to clone part of a *M. ruber* cyt-LDH.

PCR on genomic DNA from *M. ruber* strain LF6 resulted in a 1 kB DNA fragment which was cloned in a plasmid. Sequencing of this cloned PCR fragment confirmed the presence of an open reading frame with high homology to the *Aspergillus niger* CYB2 homologues and sufficient homology to the *S. cerevisiae* CYB2 gene to conclude that we have cloned a CYB2 analogue of *Monascus ruber*. The open reading frame for *M. ruber* CYB2 gene is provided as SEQ ID NO:2 and FIG. 26; a putative intron in the genomic sequence is indicated by small letters.

c) Genome and Transcriptome Analysis of Lactic Acid Metabolism

The genome of *M. ruber* LF6 and the transcriptomes of *M. ruber* LF6 and *M. ruber* KL19 (double PDC knock-out, introduced copy of bovine LDH), growing on different growth substrates, were sequenced and the relevant genes involved in lactic acid metabolism were identified on the genome by an automated annotation procedure. The RNA sequence data were used to improve the architecture of these genes. Several genes encoding lactic acid dehydrogenases were predicted for both isomers of lactic acid. For L-lactic acid, 4 cytochrome dependent LDH's were predicted, i.e. Mona 02475 (partly corresponding to SEQ ID NO:2), Mona 00569, Mona05565 en Mona06119. As Mona00569 was found to be the most active and was highly up regulated in the presence of lactic acid, this is the most obvious candidate for elimination. The sequence of this gene is given in SEQ ID No: 6 (FIG. 27). *M. ruber* was also found to contain several putative genes for cytochrome dependent LDH's that use D-lactic acid as a substrate. Again, one gene (Mona05697) was the most active gene. Since expression of Mona05697 will only lead to consumption of the undesired D-isomer of lactic acid, it may be desirable but it is probably not necessary to eliminate this gene.

Example 5

Growth of Lactic Acid Producing Strain of *M. Ruber* in a Fermentor

The fermentation was carried out in a 20-L bioreactor having a 11.3 liter total work volume. The strain used was *M. ruber*, LDH transformant of wild type LF6 with PDC1 knock out. 10 liters of S.c. medium having a composition shown in Table 6 was added. This was inoculated with 1.3 liters of inoculate obtained by two pre-culture steps. The first pre-culture was done in 4×100 ml shake flasks with 25 ml YPD medium each (composition see Table 6). Each flask was inoculated with 0.12 ml KL78 spore solution. The spore solution contains $2.11 \times 10^7$ sp/ml (66% asco-spores, 34% conidio-spores) and $2.97 \times 10^5$ cleistothesia/ml. These were incubated at 30° C. at 150 rpm for 24 h. The 2nd pre-culture was carried out in 4×2-L baffled shake flasks with 300 ml YPD medium each and inoculated with the 25-ml of the 1st pre-culture. Total volume of each flask was 325 ml. These were grown at 30° C. at 75 rpm for 52 h. The bioreactor was inoculated with 4×325 ml pre-culture. The bioreactor was maintained at 30° C. The initial pH was 3.96, and was decreased to 2.8, and kept constant at 2.8 by addition of 4M KOH. The initial stirrer speed was 250 rpm, and was during the fermentation manually increased to 450 rpm. Aeration rate was 3.0l/min. Overpressure in the reactor was 0.2 bar.

TABLE 6

Composition of media

| | Concentration |
|---|---|
| YPD medium: Component | |
| Yeast extract | 10 g/l |
| Peptone | 20 g/l |
| Dextrose | 20 g/l |
| S.c. medium: Component | |
| $(NH_4)_2SO_4$ | 5 g/l |
| $KH_2PO_4$ | 3 g/l |
| $MgSO_4 \cdot 7H_2O$ | 0.5 g/l |
| $ZnSO_4 \cdot 7H_2O$ | 4.5 mg/l |
| $MnCl_2 \cdot 2H_2O$ | 0.84 mg/l |
| $CoCl_2 \cdot 6H_2O$ | 0.3 mg/l |
| $CuSO_4 \cdot 5H_2O$ | 0.3 mg/l |
| $Na_2MoO_4 \cdot 2H_2O$ | 0.4 mg/l |
| $CaCl_2 \cdot 2H_2O$ | 12.25 mg/l |
| $FeSO_4 \cdot 7H_2O$ | 3 mg/l |
| $H_3BO_3$ | 1 mg/l |
| KI | 0.1 mg/l |
| Glucose$\cdot H_2O$ | 55 g/l |

Sigma 204 antifoam was used for foam control; totally dosed: 2 ml 4M KOH was used for pH control; totally dosed 230 ml
Extra addition of glucose$\cdot H_2O$ during fermentation; totally 1235 g The fermentation was started under aerobic conditions to produce biomass. Glucose was added during the course of fermentation. Fermentation proceeded for 137 h. Approximately 10-L fermentation broth was removed from the bioreactor. The broth was pre-filtered with a kitchen-sieve to remove the biomass, followed by additional filtration steps through finer filters. The filtrate was sterilised by gamma radiation treatment. Analysis of the filtrate after gamma radiation treatment revealed glucose (15.5 g/l), lactic acid (3.4 g/l), ethanol (23.6 g/l), glycerol (0.8 g/l).

Example 6

Extraction of Lactic Acid from an Aqueous Solution into an Extracting Solvent Comprising Tricaprylyl Amine, Octanol and Kerosene An extracting solvent containing 48 wt % tricaprylyl amine (Henkel's Alamine 336), 30 wt % octanol and 22 wt % kerosene is prepared by mixing the components at the desired ratio. A starting aqueous solution is prepared by mixing solutions of sodium lactate and lactic acid so that their final concentrations were 2.9 and 1.5 mol/kg respectively (lactic acid to sodium lactate molar ratio of 1:1.9). The aqueous solution is equilibrated at ambient temperature with three successive portions of the organic phase. Each equilibration was at aqueous to organic wt ratio of 2:1. The phases were then separated and analyzed for their lactic acid content. The results show that 83% of the lactic acid in the aqueous phase is extracted.

Example 7

Extraction of Lactic Acid from an Aqueous Solution into an Alternative Extracting Solvent Comprising Tricaprylyl Amine, Octanol and Kerosene An extracting solvent containing 48 wt % tricaprylyl amine (Henkel's Alamine 336), 20 wt % octanol and 32 wt % kerosene is prepared by mixing the components at the desired ratio. A starting aqueous solution is prepared by mixing solutions of sodium lactate and lactic acid so that their final concentrations are 0.32 mol/kg sodium lactate and 0.71 mol/kg lactic acid. The aqueous solution is equilibrated at ambient temperature with a portion of the organic phase. The phases are then separated and analyzed for their lactic acid content. The resulting aqueous phase is equilibrated with another portion of the organic phase, separated and analyzed. These operations are repeated several times. The equilibrium lactic acid concentrations (mol/kg) in the successive contacts in the aqueous and organic phases, respectively, are: 1) 0.37 and 1.16; 2) 0.14 and 0.33; and 3) 0.009 and 0.1.

Example 8

Extraction of Lactic Acid from an Aqueous Solution into an Extracting Solvent Comprising Hexanol An aqueous feed solution containing 4 mol/kg lactic acid is countercurrently extracted with hexanol at 80° C. The aqueous to organic phase ratio is 1:2.3 w/w and the number of stages was 6. The concentrations of lactic acid in the extract and in the raffinate is 1.8 mol/kg and 0.2 mol/kg respectively. The extract is back-extracted counter-currently with water at 30° C. The aqueous to organic phase ratio was 1:1.5 w/w and the number of stages was 7. The concentration of lactic acid in the regenerated extractant is less than 0.1 mol/kg and that in the resulting aqueous product solution is about 2.7 mol/kg. This example shows the recovery of lactic acid from an aqueous solution with an alcohol solvent.

Example 9

Extraction of Lactic Acid from an Aqueous Solution into an Extracting Solvent Comprising Hexanol An aqueous feed solution containing 4.5 mol/kg lactic acid is countercurrently extracted with tri-butyl-phosphate (TBP) at 25° C. The aqueous to organic phase ratio is 1:2.3 w/w and the number of stages is 6. The concentrations of lactic acid in the extract and in the raffinate are 2.0 mol/kg and 0.2 mol/kg respectively. The extract is back-extracted counter-currently with water at 85° C. The aqueous to organic phase ratio is 1:1.7 w/w and the number of stages is 8. The concentration of lactic acid in the regenerated extractant is about 0.03 mol/kg and that in the resulting aqueous product solution is about 3.5 mol/kg. This example shows the recovery of lactic acid from an aqueous solution with an oxygenated phosphorus compound.

Example 10

Extraction of Lactic Acid from Crude Material into an Extracting Solvent Comprising n-Propanol 100 g liquid crude biomass material containing 11% lactic acid is mixed at room temperature with 45 g of n-propanol (nPrOH), whereby the CSL became saturated with this alkanol, as evidenced by the separation of a small organic phase; the treated material, which became quite fluid, is extracted counter-current in four stages, with 25 g of nPrOH. The extract, on drying, left a residue of 15.3 g; 9.5 g thereof is analysed as lactic acid.

Example 11

Extraction of Lactic Acid from Crude Material into an Extracting Solvent Comprising secBuOH 15 g of secBuOH and 100 g of liquid crude biomass material containing 11% lactic acid, are mixed and heated to about 100° C. to ensure complete dissolution of the alkanol. The solids that separated are collected by centrifugation. The clarified liquor is cooled to room temperature, whereupon 19 g of an alkanolic phase separated therefrom, containing 6.1 g solids of 87% concentration in lactic acid.

Example 12

Extraction of Lactic Acid from Crude Material into an Extracting Solvent Comprising nPrOH and Tridodecylamine 100 g of liquid crude biomass material containing 11% lactic acid, are contacted counter-current with an extracting solvent made of 110 g nPrOH and 33 g tridodecylamine, in five stages. The extracted aqueous phase contains less than 1% lactic acid and only traces of phytic acid. In the organic phase, on a solvent-free basis, the phytic acid is 25% and lactic acid is 68.5%.

Example 13

Extraction of Lactic Acid into an Extracting Solvent Rilauryl Amine, (Alamine 304, Henkel) in Low Aromatics Kerosene (Isopar K)

An extracting solvent which includes 54% trilauryl amine, (Alamine 304, Henkel) in low aromatics kerosene (Isopar K, Exxon) is prepared. 3.00 grams of the extractant solution is equilibrated with 20.00 grams of 0.75 mol/kg lactic acid aqueous solution at 50° C. The phases are settled and the lactic acid concentrations in both phases are determined. The results show that the lactic acid partition coefficient is 0.28.

Example 14

Extraction of Lactic Acid into an Extracting Solvent Comprising Alamine 304 and Isopar K and Enhancer 3.051 grams of extracting solvent prepared as described in Example 13 above is contacted with 0.112 grams of an aqueous solution containing 2.95 mol/kg $H_2SO_4$. After being contacted with the extracting solvent, the $H_2SO_4$ concentration in the aqueous phase is below detection level. The $H_2SO_4$ loaded extracting solvent is then equilibrated with 20.00 grams of 0.75 mol/kg lactic acid aqueous solution at 50° C., and the phases are settled. The total proton concentrations in the aqueous and in the organic phases are determined by 0.1N NaOH titration. The lactic acid concentrations are determined by HPLC(OAKC column). The results showed that the lactic acid partition coefficient is 0.55, the concentration of the $H_2SO_4$ in the organic phase is about 0.1 mol/kg and the $H_2SO_4$ concentrations in the aqueous phases is below detection level.

Example 15

Extraction of Lactic Acid into an Extracting Solvent Comprising Alamine 304 and Isopar K and Enhancer The procedure described in the Example 13 above is repeated where the amounts of the extracting solvent and that of the lactic acid solution are 3.01 grams and 20.02 grams, respectively. The amount of the $H_2SO_4$ solution is increased to 0.311 grams. The results showed that the lactic acid partition coefficient is 0.70 and the concentration of the $H_2SO_4$ in the organic phase is about 0.3 mol/kg. Again the $H_2SO_4$ concentration in the aqueous phases is below detection level.

Example 16

Extraction of Lactic Acid into an Extracting Solvent Comprising Alamine 304 and Isopar K and Enhancer The procedure described in the Example 13 is repeated where the amounts of the extracting solvent and that of the lactic acid solution are 3.02 grams and 20.01 grams, respectively. The amount of the $H_2SO_4$ solution is increased to 0.514 grams. The results show that the lactic acid partition coefficient is 0.68 and the $H_2SO_4$ concentration in the organic phase is about 0.5 mol/kg. Again the $H_2SO_4$ concentration in the aqueous phases is below detection level.

Example 17

Stripping Using DMSO as Stripping Solvent and Conversion into Lactide 200 ml of dimethyl sulfoxide (DMSO) and 200 ml of a previously made Alamine 336 and lactic acid solution with 18.4 wt % lactic acid are added to a 500 ml round bottom, 3-neck flask with a stir shaft, temperature control, condenser, and heating mantle. The mixture is stirred and heated to 140° C. and held at 140° C. for 15 minutes. The two phases settled quickly, are separated, and are allowed to cool to room temperature. Samples of the bottom DMSO phase show 11.3 wt % lactic acid by titration and 0.58 wt %. Alamine 336 by gas chromatography. 40 ml of IsoPar K from Exxon are added to the DMSO phase in a separation funnel. The funnel is shaken at room temperature, and the phases are allowed to settle and are separated. Samples of the bottom DMSO phase show 11.4 wt % lactic acid, 2.7 wt % water by Karl Fischer titration, and 0.05 wt % Alamine 336.

230.0 g of this DMSO and lactic acid solution are then placed in a 500 ml round bottom, 4-neck flask with stir shaft, vacuum, condenser, thermocouple, and heating mantle. The material is heated at atmospheric pressure to 180° C., collecting 42.0 g overhead. The material is allowed to cool. The acid concentration in the bottom phase is determined to be 12.4 wt %, showing some condensation by loss of acidity assuming no lactic acid evaporated. The material is then heated from room temperature to 117° C. with about a 60 mm Hg pressure over 60 minutes. Another 34.7 g of material is distilled overhead. This completes the lactic acid oligomer formation step.

146.7 g of DMSO and lactic acid oligomer solution remain for the lactide formation portion. 1.53 g of FASCAT 9102, a butyltin tris-2-ethylhexanoate catalyst, is added. A dry ice cold trap and nitrogen purge is added and the condenser is changed to an ethylene glycol media at 110° C. The mixture is heated from room temperature to 145° C. at 10 mm Hg pressure over 80 minutes. Only 7.8 g of material remained in the bottom of the flask. The receiver contains 116.2 g of material. The boiling point of DMSO is close enough to lactide that it was expected that a significant amount of DMSO would be distilled over. The presence of lactide in the overheads is confirmed by gas chromatography.

Example 18

Stripping into Various Solvents

Two solutions of lactic acid and Alamine 336 are made by contacting the Alamine 336 with various amounts and concentrations of aqueous lactic acid solutions. Alamine 336 mixtures with 4.35 wt % and 18.85 wt % lactic acid are obtained. 2 ml of the Alamine 336 and lactic acid solutions are contacted separately with the following stripping solvents—dimethyl sulfoxide (DMSO); N,N-dimethyl formamide (DMF); 1,4-dioxane; N-methyl pyrrolidinone (NMP); and, 1,3-dioxalane. The samples are held at the specified temperature in an oil bath for about 45 to 60 minutes with regular mixing. The 1,4-dioxane and 1,3-dioxalane samples form a single liquid phase at temperatures between 20° C. and about 80° C. A similar procedure is used for contacting Alamine 336 and lactic acid solutions with lactide and tetramethylene sulfone (TMSF). Phases are allowed to settle at specified temperature and then quickly separate by piping out the bottom phase. Samples are taken for titration with a sodium hydroxide solution with phenolphthalein as an indicator to determine lactic acid concentration, and gas chromatography to determine Alamine 336 concentrations. In all cases, the Alamine 336 phase is the least dense phase or the top phase.

Table 7 reports the lactic acid and Alamine 336 concentrations in the top and bottom phases. The partition coefficient is calculated by dividing the lactic acid concentration in the Alamine 336 top phase by the lactic acid concentration in the bottom polar liquid phase. The results show that significant amounts of lactic acid distributes into the polar liquid phase at these conditions. In some of the solvents, there is a significant amount of Alamine 336 co-extracted into the polar liquid phase. Dimethyl sulfoxide looks like a favourable solvent for this type of process because of the good selectivity for the lactic acid over the Alamine 336. This example shows that lactic acid can be back extracted into a polar liquid from the initial extracting solvent with good efficiency. This example supports the feasibility of a process that uses a back extraction of the lactic acid into a second polar liquid.

TABLE 7

| Solvent | Sample | Temp ° C. | Latic Acid Wt % | Alamine 336 Wt % | Partition Coeff |
|---|---|---|---|---|---|
| DMSO | Top | 140 | 0.18 | 72.4 | 0.19 |
|  | Bottom |  | 0.93 | 0 |  |
|  | Top | 140 | 0.69 | 66.03 | 0.06 |
|  | Bottom |  | 11.78 | 0.98 |  |
| DMF | Top | 110 | 0.16 | 61.09 | 0.14 |
|  | Bottom |  | 1.13 | 1.17 |  |
|  | Top | 110 | 1.49 | 70.17 | 0.13 |
|  | Bottom |  | 11.36 | 19.23 |  |
| NMP | Top | 90 | 0.33 | 65.26 | 0.29 |
|  | Bottom |  | 1.13 | 1.72 |  |
|  | Top | 110 | 2.73 | 67.14 | 0.22 |
|  | Bottom |  | 12.2 | 19.71 |  |
| TMSF | Top | 140 | 0.88 | 71.69 | 0.21 |
|  | Bottom |  | 4.15 | 5.28 |  |
|  | Top | 140 | 1.25 | 73.06 | 0.17 |
|  | Bottom |  | 7.52 | 10.09 |  |
|  | Top | 140 | 1.50 | 78.10 | 0.17 |
|  | Bottom |  | 8.66 | 13.56 |  |
| Lactide | Top | 140 | 2.44 | n.d. | 0.82 |
|  | Bottom |  | 2.98 |  |  | n.d. not determined

Example 19

Stripping into Triethylamine

Alamine 336 and an aqueous lactic acid solution are contacted to obtain a 26.74 wt % lactic acid in the Alamine 336 phase. Ten grams of the lactic acid loaded Alamine 336 phase is contacted with 5 grams of triethylamine (stripping solvent) in a 125 ml separation funnel. The flask is shaken for one minute at 24° C., and the phases are allowed to settle. The top phase contains Alamine 336 excess triethylamine, and virtually no lactic acid while the bottom phase contains 43 wt % lactic acid and triethylamine. Acid concentrations are determined by titration with sodium hydroxide. The back extraction is scaled up to allow the distillation experiment.

Thirty grams of a 43 wt % lactic acid in triethylamine mixture are added to a 500 ml round bottom, 3-neck flask equipped with a dry ice trap, pressure gauge, condenser, thermocouple, and heating mantle. The triethylamine evaporates initially at 23° C. and 10 mm Mg. The temperature is increased to 120° C. and the mixture was held at that temperature for 90 minutes. About 69% of the triethylamine is evaporated out. The chiral purity of the lactic acid is not changed significantly after heating.

The triethylamine removal can be dramatically increased in the presence of a solvent. A 21.5 wt % lactic acid solution in a mixture of triethylamine and N-methyl-2-pyrrolidinone is heated at 55° C. and 10 mm Hg pressure for two hours and 48% of the triethylamine is evaporated from the solution. The remaining mixture is heated to 110° C. where it is held for 80 minutes. At this point, 96% of the triethylamine is evaporated. The chiral purity of the material is not significantly changed. This example shows the back extraction of the lactic acid from the extracting solvent and then the ability to evaporate the back extraction solvent to obtain a concentrated lactic acid product.

Example 20

Conversion of Lactic Acid into Lactide Using Alamine 336 as Extracting Solvent 600 ml of caustic washed Alamine 336, 800 ml of 15 wt % aqueous lactic acid solution, and 100 ml of 50 wt % aqueous lactic acid solution are added to a separation funnel and mixed at room temperature. The phases are allowed to settle overnight. The phases are split and the top organic phase is centrifuged to remove entrained aqueous phase. The lactic acid concentration in the organic phase is determined to be 19.75 wt % by titration with a sodium hydroxide solution with phenolphthalein as an indicator. 304.6 grams of the Alamine 336 and lactic acid solution are added to a round bottom, 4-neck flask with a stir shaft, thermocouple, condenser, heating mantle and nitrogen purge. The solution is heated up to 200° C. and atmospheric pressure over 45 minutes. It is then allowed to cool to about 64° C. Then it is heated to 200° C. at 60 mm Hg pressure over 30 minutes. The flask is held at 200° C. and 70 mm Hg pressure for 45 minutes. The flask is cooled and the bottoms split into two phases upon cooling. The top phase is determined to be virtually all Alamine 336 by gas chromatography. The bottom phase is viscous and consisted of lactic acid oligomers and small amount of Alamine 336.

185.9 grams of Alamine 336 and lactic acid oligomer solution (about 54.8 wt % oligomer at average M.W. of 476) are added to a 500 ml round bottom, 4-neck flask with a stir shaft, high vacuum system, nitrogen purge, condenser, thermocouple, and heating mantle. With the solution at 125° C., 900 μl of FASCAT 9102, a butyltin tris-2-ethylhexanoate catalyst from Atochem is added. The solution is heated to 200° C. over four hours, and the mixture held at 200° C. for 60 minutes. The pressure is held constant at about 1 mm Hg over the entire heating time. The condenser media temperature is held at 110° C. The overhead material crystallizes upon cooling. The flask bottoms after heating are determined by gas chromatography to be virtually all Alamine 336. 139 g of material goes overhead with virtually all the oligomer being transformed to lactide and distilled overhead. Some Alamine 336 may also be distilled overhead due to the high temperature and low pressure; this can be confirmed by gas chromatography. The lactide obtained has a chiral purity of less than 80%. The chiral purity can be improved by using lower temperatures and using high surface area equipment for the lactide reactor to allow for good mass transfer of lactide out of the reactor.

Example 21

Conversion of Lactic Acid in a Aqueous Solvent into Lactide

A three-neck, one-liter round-bottom flask is fitted with a mechanical stirrer, nitrogen sparged, and a straight distillation take-off to a condenser, and the receiver to a vacuum take-off and manometer. The flask is charged with 650 ml (770.4 g) of 88% L-lactic acid feed and heated at 120° C.-130° C. with stirring and nitrogen bubbling. Water was distilled using a water aspirator at 150-200 Torr. Aliquots are removed during the course of the heating and characterized by titration for DP (degree of polymerization). Then, after methylation with diazomethane, the aliquots were characterized by gas chromatography (GC). The results indicate the presence of lactide peaks when the DP is about 2.

Example 22

Conversion of Lactic Acid in a Aqueous Solvent into Lactide

An experimental vapour reactor is provided with catalyst comprising 10-20 mesh silica gel/alumina catalyst (Akzo-L1 A-30-5P catalyst, 87% silica/13% alumina, Akzo Chemicals B.V.). The nitrogen flow rate is adjusted to 1600 ml/min. and it plus a lactic acid feed were passed through reactor at a superficial vapour velocity of 0.12 ft/sec. The space time of the contents is 2.8 seconds. Lactic acid feed comprises commercial "85% lactic acid" (61% L-lactic acid, 20% L-L,lactoylactic acid, 4% L,L,L-lactollactoyllactic acid, and 15% water) which is diluted with an additional 11% by weight of water just prior to the run. Results recorded are set forth in Table 8 below: Table 8: Results

| Catalyst Bed Temp ° C. | Lactic acid feed (g) | All Products (g) | LD product (g) | LD Yield |
|---|---|---|---|---|
| 206 | 128.6 | 115.8 | 22.73 | 25.7 |

Example 23

Conversion of Lactide into PLA

In the examples and comparative examples, the number average molecular weight (Mn) of PLA was determined by size exclusion chromatography in chloroform at 35° C., with calibration at the start of eight polystyrene standards of average molar masses known number of 600 to 1 700 000 Dalton. size Exclusion chromatography used Agilent Technologies 1200 Series equipment. The samples dissolved in chloroform at 0.1% (w/v) were eluted at a rate of 1 ml/min through a PL gel guard column (10 μm) and two PL gel gradient columns (5 μm) mixed-d. The injected volume was 100 μl.

In the examples and comparative examples, the colour of the PLA was determined directly after polymerization and before any recrystallization of the PLA (PLA gross).

1. Synthesis of (2,4-di-tert-butyl-6-(((2-(dimethylamino) ethyl)(methyl)amino)methyl)phenoxy) (ethoxy)zinc, hereinafter known as DDTBP-Zn (OEt)

The synthesis was carried out according to the procedure described by Williams et al. in J. Am. Chem. Soc., 2003, 125, 11350-11359.

2. Experiments 1 and 2

Bulk polymerization of L-lactide was carried out under an inert atmosphere, in the presence of the catalyst DDTBP-Zn (OEt) represented by the following formula:

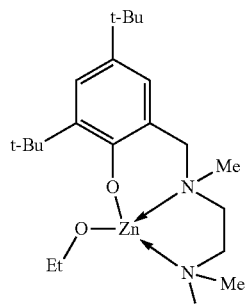

Polymerization took place in the presence of 1-octanol, as initiator in a glass reactor with a capacity of 50 ml under an inert atmosphere, with 5 g of L-lactide, catalyst and the initiator in amounts as described in Table 9. Each time, 1 ml of catalyst solution in toluene was used. The conversion of L-lactide to polylactide was determined after 30 minutes of polymerization using the polymer previously recrystallized from a mixture of chloroform and ethanol and dried under vacuum.

4. Experiments 3-6

The bulk polymerization of L-lactide was carried out under an inert atmosphere in the presence of catalysts other than those mentioned in the method of the invention. Polymerization took place in a glass reactor with a capacity of 50 ml and carried out under an inert atmosphere with 5 g of L-lactide, catalyst and 1-octanol (initiator) in such amounts indicated in Table 9. For each reaction, 1 ml of catalyst solution in toluene was used. The extent of conversion of L-lactide in polylactide was determined in the same way as described for Experiments 1 and 2 above.

The catalysts tested were

Bis[bis(trimethylsilyl)amide]zinc identified below Zn[N (SiMe$_3$)$_2$]$_2$,

Diethylzinc identified below and DEZ

Trifluoromethane sulfonate zinc identified below Zn (OTf)$_2$.

The results are shown in Table 9 below. As for Experiment 7 (negative control), no polymerization reaction took place in the presence of zinc trifluoromethanesulfonate.

TABLE 9

| Experiment | TP | L/O | L/C | Catalyst | Conv | Color | Mn (Dalton) | PD |
|---|---|---|---|---|---|---|---|---|
| 1 (invention) | 185 | 316 | 5028 | DDTBP-Zn(OEt) | 90 | Colourless | 77.000 | 1.8 |
| 2 (invention) | 185 | 307 | 4876 | DDTBP-Zn(OEt) | 88 | Colourless | 88.000 | 1.6 |
| 3 (comparative) | 185 | 340 | 5607 | Zn[N(SiMe$_3$)$_2$]$_2$ | 83 | Yellow | 66.000 | 1.5 |
| 4 (comparative) | 185 | 323 | 5270 | DEZ | 81 | Yellow | 78.000 | 1.5 |
| 5 (comparative) | 185 | 320 | 5221 | DEZ | 83 | slightly yellowish | 66.000 | 1.4 |
| 6 (comparative) | 185 | 362 | 4984 | Zn(OTf)$_2$ | — | — | — | — |

Key:
"TP"—Temperature of polymerisation (° C.);
"L/O"—Lactide/octanol (mol/mol);
"L/C"—Lactide/catalyst (mol/mol);
"Conv"—Conversion of lactide to polylactide (%);
Colour—Color of polylactide (PLA total);
"PD"—Polydispersity (Mw/Mn);
"—" non applicable.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

The invention claimed is:

1. A method for producing polylactic acid (PLA) comprising:
   (A) fermenting in a fermentation vessel a recombinant micro-organism of the genus *Monascus*, that has been genetically modified to produce increased levels of lactic acid and have tolerance to lactic acid at a pH of at less than 5, in a medium at a pH less than or equal to 5 under conditions which produce lactic acid into the medium, such that said medium comprises at least 50 g/L lactic acid,
   (B) converting the lactic acid produced into lactide, and
   (C) polymerizing the lactide to form PLA.

2. The method according to claim 1 wherein the lactic acid is recovered from the fermentation medium prior to conversion into lactide, wherein the recovery comprises:
   (A) extracting free lactic acid from said medium clarified of debris by contacting said medium with an extracting solvent, to form:
      (i) a lactic acid-containing extract and
      (ii) a lactic acid-depleted aqueous solution; and
   (B) separating said lactic acid-containing extract (i) from said aqueous solution (ii),
   thereby obtaining recovered lactic acid.

3. The method according to claim 2 wherein the extracting solvent comprises one or more of 1-butanol, 2-ethyl hexanol, 1-octanol, methyl isobutyl ketone, cyclohexanone, disobutyl ketone, isopropyl ether, ethyl acetate, isobutyl acetate, ethyl lactate, butyl lactate, octyl lactate, N,N-dibutyl lactamide, hexanoic acid, a tertiary alkylamine tricaprylyl amine, or Alamine 336.

4. The method according to claim 2, wherein the recovery further comprises:
   (C) stripping the extracted lactic acid from said separated extract (i) using a stripping solvent to form as immiscible phases:
      iii) the stripping solution containing lactic acid, and
      iv) lactic acid-depleted extracting solvent; and
   (D) separating the stripping solution containing lactic acid
      (iii) from said lactic acid-depleted extracting solvent
      (iv),
   thereby obtaining recovered lactic acid.

5. The method according to claim 4, wherein the stripping solvent is an aqueous solvent, polar organic solvent, or mixtures thereof.

6. The method according to claim 1, wherein the lactic acid is recovered from the fermentation medium prior to conversion into lactide, wherein the recovery comprises:
   (A) precipitating contaminants in the medium, optionally clarified of debris, by use of an alcohol, and
   (B) removing the precipitate to obtain a clarified alcohol solution containing lactic acid, thereby obtaining recovered lactic acid.

7. The method according to claim 6 wherein the alcohol is a $C_1$ to $C_4$ straight chain or branched alcohol.

8. The method according to claim 1, wherein the lactide is converted from lactic acid directly or via polycondensation of lactic acid to form lactic acid oligomers.

9. The method according to claim 1, wherein the recovered lactic acid is converted into lactide by:
   (A) heating the recovered lactic acid to oligomerise the lactic acid, and
   (B) heating the lactic acid oligomer so formed to produce a vapour of lactide.

10. The method according to claim 9, wherein the recovered lactic acid is in a hydrophobic solvent.

11. The method according to claim 9, wherein the step of heating the lactic acid oligomer to produce a vapour of lactide is performed in the presence of a catalyst.

12. The method according to claim 1, wherein the lactic acid is in an aqueous solution, and is converted into lactide by:
   (A) heating the aqueous solution of recovered lactic acid to form a vapour, and
   (B) passing the vapour so formed through a reactor maintained at elevated temperature, in which a catalyst is optionally disposed.

13. The method according to claim 12, wherein the catalyst is alumina.

14. The method according to claim 1, wherein the lactic acid is in an aqueous solution, and is converted into lactide by the removal of water from the aqueous solution.

15. The method according to claim 1, where the lactide is polymerised into PLA by a ring opening in the presence of a metal catalyst.

16. The method according to claim 10, wherein the hydrophobic solvent is Alamine 336.

17. The method according to claim 11, wherein the catalyst is a tin catalyst.

18. The method according to claim 17, wherein the catalyst is tin (II) octanoate.

19. The method according to claim 1, wherein the recombinant micro-organism of the genus *Monascus* is fermented in a medium at a pH less than or equal to 4 under conditions which produce lactic acid into the medium.

20. The method according to claim 1, wherein during the fermentation of the strain the pH of the medium drops to a value below the pKa value of lactic acid (of 3.85).

21. The method according to claim 1, wherein the recombinant micro-organism is *Monascus ruber*.

22. The method according to claim 1, wherein the yield of lactic acid is at least 2 g/L.

23. The method according to claim 1, wherein the lactic acid productivity is at least 1 g/L/hr.

* * * * *

```
                         SEQUENCE LISTING

<160> NUMBER OF SEQ ID NOS: 6

<210> SEQ ID NO 1
<211> LENGTH: 999
<212> TYPE: DNA
<213> ORGANISM: Artificial Sequence
<220> FEATURE:
<223> OTHER INFORMATION: Codon optimized bovine LDH sequence
<220> FEATURE:
<221> NAME/KEY: Intron
<222> LOCATION: (503)..(566)

<400> SEQUENCE: 1
atggcaaccc tgaaggacca gcttatccaa aacctgctca aggaagaaca cgtccccaa      60 aacaagatta ctatcgtcgg agtcggtgcc gttggaatgg cctgcgctat ctccattctg    120
atgaaggacc tcgcagatga ggtggcgctc gtcgacgtta tggaggataa gctcaagggt    180
gaaatgatgg accttcagca tggatcgctt ttcttgcgca cacccaagat cgtcagcggc    240
aaggattaca acgttacagc aaattcccgc cttgtgatca ttactgcagg cgcgcgtcag    300
caagagggtg aatcgagact gaacctcgtc caaaggaacg ttaatatctt caagttcatc    360
atccccaaca ttgtcaagta ctccccaaat tgtaagctgc tcgtcgtttc taatccggtt    420
gacatcctca cttatgtggc ctggaagatt tctggcttcc ctaagaaccg agttatcggc    480
tcgggttgca atcttgatag cgctcgattt cggtatctta tgggagagag attgggcgtc    540
catcccctgt cctgtcacgg ctggatcttg ggagaacacg gcgactcctc tgtgccagtc    600
tggtcgggtg tcaacgtggc cggagtcagc cttaagaatt gcatccgga gttgggcacc     660 gacgccgata aggaacagtg gaaggctgtc cacaagcaag tggtcgactc cgcatacgag    720
gttatcaagc tgaagggata tacctcctgg gcgattggcc tctctgtggc cgatcttgct    780
gaaagcatca tgaagaactt cgccgtgtc catcctatct ccacgatgat taagggtctg    840
tacggaatta aggaagacgt gtttttgtct gtcccctgca tcctgggcca gaatggtatt    900
tcggatgttg tgaaggtcac cctcacgcac gaggaagagg cttgcttgaa gaagtcggcg    960
gacactctct ggggcatcca aaaggaactc caattttaa                           999

<210> SEQ ID NO 2
<211> LENGTH: 1015
<212> TYPE: DNA
<213> ORGANISM: Monascus ruber
<220> FEATURE:
<221> NAME/KEY: Intron
<222> LOCATION: (503)..(566)

<400> SEQUENCE: 2
aagtatgcgg ggcaggatgc cacaaaggcc tattctgaag ttcacactcc gagccttatc      60
aaatggaatt tatccccaga caagctcaag ggcactctcg ccaatccac tattgacgat     120 gaatggatga accaccgcc aaatgagagc gacaaagttg ttttagagaa cgagaaaccg     180
ccgctgcata tgctgataaa ctcgcacgat ttcgaagtcg tagcttccaa gactgcaagt    240
aagaagacct gggccttcta ttccagcgct gcaacggacc tcatcacccg tgatgccaat    300
aagtcatgct ttgaccggat atggttccga ccccgggtac tgaggaatgt gcgtaccgtc    360
```

```
aaaacgcgca cgaagatcct cggggttgac agcagtctcc cacttttcgt gagtccagca    420
gctatggcta agctcattca cccagatggt gagtgtgcca tagcaagggc atgtgcaaat    480
aagggtatca ttcaaggtgt acgttcattg cagattcgaa cacttcccgt tctagttgca    540
accttcttaa catcaatgtc ggataggtgt cgaataactc atcattccca atcgaagagc    600
tccgggaggc ggcaccgtct ggaaatttta ttttccagtt atatgtgaat cgggatcgag    660
agaaatctgc ggaactactc cgcaggtgct cagctaaccc gaacatcaag gccatcttcg    720
tgaccgttga cgcagcctgg cccggtaaac gtgaggcaga cgaacgagtc aaagcggatg    780
agagcctgac agtccccatg tccccatcga acacgcaa cgacaaaaag ggggcgggc    840 tcgggcgcgt tatggctggg ttcatcgacc cggggctcac ctgggaagat ctggcctggg    900
tgcgacaaca tacccatctc cccgtttgtc tgaagggaat tatgtccgca gacgatgcca    960
ttctagccat gaaattggga ctagatggca tcctgctctg caaccacggc ggccg    1015
```

<210> SEQ ID NO 3
<211> LENGTH: 1307
<212> TYPE: DNA
<213> ORGANISM: Monascus ruber

<400> SEQUENCE: 3

```
tgggtgggya aytgyaatga rctgaatgct ggttackccg ccgatggcta cgctcgtatc     60
aagggtatct ctgccctgat caccactttc ggtgtcggtg agctctctgc cgccaacgcc    120
atcgccggtt cctactcgga rcgggtgccc gttgtccaca ttgtcggtga gcccagcacg    180
gcatcccaga caaccgcca gcttctgcac cacaccctcg gaaacggtga cttcgatgtc    240
ttcgagaaga tcttcgccaa gatctctact tccgtcgtta agattagaga ccccgccaat    300
gccgccacca tgatcgacca cgttctccgg gaatgtgtta tccagagccg cccgtctac    360 atcggtctgc cctctgatat ggttaccaag aaggttgagg gagcccgcct gaagacccc    420 atcgacctgt ccctccccga gaaccccaag gagaaggagg actacgtcgt cagcgtcgtt    480
ctcaagtatc tgcacgctgc caagaaccct gtcatcctcg tcgatgccgg tgtcaaccgc    540
cacaatgccc aggctgaggt gcacgagctg atcaagaagt ctggaatccc caccttcatc    600 accccccatgg gcaagggcgg tgttgacgaa accctcccca actacggcgg tgtctacgcc    660
ggtaccggtt ccaacagggg cgtccgcgag cgtgtcgagg aatctgacct catcctgaac    720
atcggacctc tccagtccga cttcaacacc accggcttct cctaccgcac cagccagctc    780
aacaccatcg agttcgaccg cgacagcgtc caggtccgct actcctacta ccccgacatc    840
cagcttaagg gagttctcca gaacctcatc gccaccatgg gcgaactcaa catcgagcct    900
ggcccgaccc cctccaacgc cctccccgcc aacggcgttg accacgaaac tgcagagatc    960
acccacgaat ggctctggcc catggtcggc aactggctcc gcgaaggtga tgttgtcctc    1020
actgaaaccg gtaccgccaa cttcggtatc tgggaaaccc gcttcccaa gaacgttcag    1080 gccatctccc aggtcctctg gggttccatc ggttactccg tcggtgcctg cttgggtgct    1140
gctctcgccg ctcgggaact tggcgacaac cgtgtcctac tcttcgtcgg tgatggtagc    1200
ttycagatga ccgcccagga gatcagcact atgatccgtc agggattgaa gcctattgtc    1260
ttcgtcatct gcaacaacgg ctacacmatc garmgctaca tccacgg    1307
```

<210> SEQ ID NO 4
<211> LENGTH: 1287
<212> TYPE: DNA

<213> ORGANISM: Monascus ruber

<400> SEQUENCE: 4

| | | | | | |
|---|---|---|---|---|---|
| ctgaacgccg | sctacgccgc | cgacggatay | gctcgtgtca | atggaatcgc | tgccttggtt | 60 |
| actactttcg | gtgtaggaga | gctgtcagca | gtgaacgcca | ttgcgggagc | ctactcagag | 120 |
| tatgtaccca | tcgttcacat | tgttggccaa | ccaaatacaa | ggtcacagag | agatggaatg | 180 |
| ctgttgcatc | atacgttggg | caacggcgac | tttgatgtct | ttaccaagat | gagtgcttcc | 240 |
| atttcgtgcg | ctgttgcaaa | gttgaacgac | ccccatgaag | ctgcaacgct | catcgaccac | 300 |
| gccattcggg | aatgctggat | cgcagcaga | ccggtgtaca | tcaccctccc | tacagacatc | 360 |
| gtcacgaaga | aagtcgaagg | tgaaaggctg | aagaccccaa | ttgacctgac | aatgccagag | 420 |
| aatgaagcag | aaagggaaga | ttacgtggtg | gatgttgttt | tgaaataccct | gcaagccgcg | 480 |
| aaaaacccag | tcattctagt | tgacgcatgc | gcaatccgtc | acagggtcct | ggacgaggta | 540 |
| catgaccttg | ttaaggcttc | tggcttgcca | acctttgtga | ccccaatggg | caaaggagca | 600 |
| gtggacgaga | ctcatccaaa | ttatggtggt | gtgtatgctg | gagatgggtc | taataccggc | 660 |
| gtccgtgaag | ttgttgaagc | ttccgaccct | attctgagca | ttggcgccat | taaatccgat | 720 |
| ttcaatactg | ccggcttcac | ataccgcatc | ggccaactta | acacgatcga | cttccatagt | 780 |
| accttcgtgc | gagtgaggta | ttcggagtac | ccgaacacaa | acatgaaggg | tgttctaagg | 840 |
| aagatcatcc | agaaaatggg | cccctcagc | aagacgcca | ttccaaagac | tatcaacaag | 900 |
| gttccagaac | atatcaaagc | ttctggtgac | acgcggatta | ctcatgcttg | gttgtggccg | 960 |
| acagtcggac | agtggctgca | gccggaggat | gttgtcgtca | ctgagactgg | aactgcaaac | 1020 |
| tttggaatct | gggaaaccag | gttcccacac | ggtgtcacgg | ctataagcca | agtcctctgg | 1080 |
| ggaagcattg | ggtacacggt | tggagcatgt | caaggcgccg | cactagctgc | aaaggagata | 1140 |
| ggcaaccgtc | gcactgtact | ttttgttggc | gatggcagtt | tccagcttac | cgcgcaggaa | 1200 |
| gtgagcacca | tgctcagaaa | taagctgaac | ccgatcattt | ttgtgatctg | taacgaaggg | 1260 |
| tayacratcg | agcgctacat | ccatggc | | | | 1287 |

<210> SEQ ID NO 5
<211> LENGTH: 1680
<212> TYPE: DNA
<213> ORGANISM: Monascus ruber

<400> SEQUENCE: 5

| | | | | | |
|---|---|---|---|---|---|
| atgaccactg | tcggaagcta | cctcgcagaa | aggctctccc | aaattggcat | cgagcgccac | 60 |
| ttcgtcgtcc | caggcgacta | caacctcatc | ctcctcgaca | aactccaaca | acaccccaaa | 120 |
| ctcgacgaaa | tcaactgcac | aaatgaacta | aactgctcca | tggccgcaga | aggctacgcc | 180 |
| cgcgcaaaag | gcgtagccgc | ctgcgtcgtg | acgttcagcg | tcggcgcatt | ctccgcattc | 240 |
| aacggcatcg | gcagcgcata | cggtgagaat | ctccctgtca | tcctcatctc | cggttccct | 300 |
| aataccaacg | atcttggctc | gtcgcatttg | ctgcatcata | cgatcggtac | gcataatttt | 360 |
| gactaccagc | ttgagatggc | gaaaaatatc | acctgctgtg | ctgttgcgat | tcgtcgtgcc | 420 |
| tcggatgcgc | cgcggttgat | cgacgaggct | attcgcaccg | cacttcgggc | gcggaaacca | 480 |
| gcgtatattg | agattcctac | gaacctctcg | ggccagccgt | gttccctgcc | cggaccggcg | 540 |
| tcggggattc | tcaagccgga | tacgagtgat | attgatactc | ttgcggaagc | gctgaaggca | 600 |
| gccaacgact | tcctctctac | ccggaacaag | gtgtccttac | tggttggccc | taaggttcgc | 660 |
| gcagcaggcg | ctgaacatgc | cgtgatccat | cttgctcaag | ccctgggatg | cgcggtggcc | 720 |

```
gtgctaccca gtgccaaatc gttcttcccg gagactcatc cgcagttcgt gggtgtatac    780
tggggcgaag tgagcacgaa gggcgcgaat gctatcgtcg actggtccga tacccttatt    840
tgcgtgggga cggtttacac cgactacagc accgttggat ggacgggggct acccgaagca   900 gccagtctga ccattgacct ggaccatgtc agtttccctg gatccgatta caaccagatc    960
catatgctgg agttcgtggc aggactggcg aagctggtga agaagaaccc cctgacactc   1020
gtcgaatata accgtctgca accagaccct ctcgttcaca cgccatctcc gccggatcaa   1080
cgactgagcc ggcgagaaat gcagtaccag atcagccagt cctgacgcg caacacgacg    1140 gtcgttgtgg acacgggcga ctcgtggttc aacgggatgc agatggacct tccggacgga   1200
gtgagatttg aggttgagat gcaatgggga cacatcggat ggtccgttcc agcagcactg   1260
ggtctggccg ccgcaaaccc cgagcgacag atagtcgtca tggtaggcga tgggtcgttc   1320
cagatgacgg gccacgaggt gtcaaatatg actcgattag gctaccgat tatcatcttc    1380 ctgatcaaca atgacgggta cacaatcgaa gtcgagatcc acgatggcat ctacaacaac   1440
atcaagaact gggattacgg cgcgttcgtc gagtcgttca atgccaagga gggacatggg   1500
aaggggtatc gtgttaccac ggcggggaa atgcacaggg ccattgaggc ggcgaagaag    1560
aataaacagg ggccaacact aatcgagtgt gatattgatc gcgatgattg cagtaaggag   1620
ttgatcagtt gggggcatta tgtggctgct gcgaatggca agcctcctgt tgccaggtga   1680
```

<210> SEQ ID NO 6
<211> LENGTH: 1655
<212> TYPE: DNA
<213> ORGANISM: Monascus ruber

<400> SEQUENCE: 6

```
atgtctcaac ctaagcttac cggcgctgat atcgccaaac acaattccaa ggactcgtgc     60
tgggtcattg tccacgggaa agcatacgat gtcacggact tcctgccagg tattgattga    120
cccccctgtc cgggaattcc gagatgctgc ctgcgttcat tgaatactga tttgcatgaa    180
tttgatcaat tatagaacat cccggtggcc agaagattat cctgaagtat gccggcagag    240
atgccacgga agaattcgag cccatccacc ccccggatac cctggacaag tacctcgaca    300
agtcaaagca cttgggcgag gtcgacatgg ccactgtcgc acacgacgag aaggctgtcg    360
atcccgagga cacggctcgc caggaaagaa tcaagctcat gccatcgttg caatcctgct    420
acaatctgat ggactttgaa tccgtggcgc agcaggtcat gaagaagact gcgtgggcat    480
actactcaag tggtgctgat gatgaaatcg tatgaccata tctggatttc tcgttccctt    540
tgcagcacat actgacttgc gtctgttcac agaccctgcg agaaaaccac actgccttcc    600
ataagatctg gttccggccg cgagtcctag tcgacgtgga acatgtcgac tactctacga    660
ccatgctggg aaccaaggtc tccgctccct tctatgtgac ggccacagcc ctgggcaaac    720
tgggacaccc cgagggtgag gtcgttctca cccgttcctc ctaccgtcac aacgtcatcc    780
agatgattcc cacgctcgcc tcgtgctcct ttgacgagat tattgacgcc cgccaaggcg    840
atcaggtcca gtggctgcag ctctacgtca caagaaccg cgatatcacc aagcgcattg    900
tgcaacatgc cgaagcccgc ggctgcaagg gcctcttcat caccgtcgac gccccgcaat    960
taggtcgtcg agagaaagac atgcgctcca gttctccga cgagggctcc aacgtccaga   1020
aagaagaggg tgaggagaac gtcgaccgct tcagggtgc cgcccgtgct atctcctcgt   1080
tcatcgaccc cgccctctcc tggaaggata tccctggtt ccaatccatc acgaagatgc    1140
```

```
ccatcgtcct gaagggtgtg cagtgcgtcg aagacgtttt ccgtgctatc gaagccggag    1200
tccagggtgt tgtgctgtcc aatcacggtg gccgtcagct cgagttcgca ccatcggctg    1260
tcgagcttct ggccgaggtt atgcctgcgc tgcgccagcg cggcttggag aacagcatcg    1320
aggtgtacat cgacggtggc atccgcagag gcactgatat cgtcaaggcg ctctgccttg    1380
gcgcccaggg cgtggggatt ggtcgtcctt tcctgtacgc catgtcggcg tacggccagg    1440
ccggtgtcga caaggccatg cagcttctca aggatgagat ggagatgaac atgagactca    1500
tcggagccac taaggtctcc gagctgagcc ccagcctcgt cgatacccgc ggtcttcttg    1560
gtggtcacca cgctcctgtt ccgtccgaca cgctgggcat gaaggcgtac gatgcgctcc    1620
aggctccgcg gttcaacgaa aagtcgaagt tgtag                              1655
```